United States Patent
Chiu et al.

(10) Patent No.: US 10,429,294 B2
(45) Date of Patent: Oct. 1, 2019

(54) OPTICAL PAINTING AND FLUORESCENCE-ACTIVATED SORTING OF ADHERENT CELLS

(71) Applicant: University of Washington, Seattle, WA (US)

(72) Inventors: Daniel T. Chiu, Seattle, WA (US); Chun-Ting Kuo, Seattle, WA (US); Jiangbo Yu, Bothell, WA (US)

(73) Assignee: University of Washington, Seattle, WA (US)

( * ) Notice: Subject to any disclaimer, the term of this patent is extended or adjusted under 35 U.S.C. 154(b) by 3 days.

(21) Appl. No.: 15/563,121

(22) PCT Filed: Apr. 1, 2016

(86) PCT No.: PCT/US2016/025633
§ 371 (c)(1),
(2) Date: Sep. 29, 2017

(87) PCT Pub. No.: WO2016/161325
PCT Pub. Date: Oct. 6, 2016

(65) Prior Publication Data
US 2018/0080863 A1    Mar. 22, 2018

Related U.S. Application Data

(60) Provisional application No. 62/142,340, filed on Apr. 2, 2015.

(51) Int. Cl.
*G01N 33/58* (2006.01)
*G01N 21/64* (2006.01)
(Continued)

(52) U.S. Cl.
CPC ..... *G01N 15/1475* (2013.01); *A61K 49/0019* (2013.01); *A61K 49/0021* (2013.01);
(Continued)

(58) Field of Classification Search
CPC ............ A61K 49/0019; A61K 49/0021; C12N 13/00; C12Q 1/68; G01N 15/147;
(Continued)

(56) References Cited

U.S. PATENT DOCUMENTS

| 5,656,441 A | 8/1997 | Faller et al. |
| 8,401,263 B2 | 3/2013 | Palsson et al. |

(Continued)

FOREIGN PATENT DOCUMENTS

| CN | 103261087 A | 8/2013 |
| JP | 2017507191 A | 3/2017 |

(Continued)

OTHER PUBLICATIONS

Kuo et al. Nature Communications, vol. 7, article #11468, Apr. 27, 2016, pp. 1-11.*

(Continued)

*Primary Examiner* — Maureen Wallenhorst
(74) *Attorney, Agent, or Firm* — Christensen O'Connor Johnson Kindness PLLC

(57) ABSTRACT

Methods of optically marking and sorting adherent cells are provided. The methods include providing a plurality of adherent cells attached to a substrate, each adherent cell of the plurality of adherent cells having an optical marker. The methods also include selectively applying light energy to a subset of the plurality of adherent cells, and detaching the plurality of adherent cells from the substrate. These methods also provide the sorting of the plurality of adherent cells.

20 Claims, 24 Drawing Sheets adherent cells labeled with fluorophores in culture or tissue slice selective irradiation based on image analysis dissociation and cell sorting

(51) Int. Cl.
*G01N 21/25* (2006.01)
*G01N 15/14* (2006.01)
*A61K 49/00* (2006.01)
*C12Q 1/68* (2018.01)
*C12N 13/00* (2006.01)
*G01N 15/10* (2006.01)

(52) U.S. Cl.
CPC .............. *C12N 13/00* (2013.01); *C12Q 1/68* (2013.01); *G01N 15/147* (2013.01); *G01N 21/25* (2013.01); *G01N 21/64* (2013.01); *G01N 33/582* (2013.01); *G01N 2015/1006* (2013.01); *G01N 2015/149* (2013.01); *G01N 2015/1497* (2013.01)

(58) Field of Classification Search
CPC ....... G01N 15/1475; G01N 2015/1006; G01N 2015/149; G01N 2015/1497; G01N 21/25; G01N 21/64; G01N 21/6486; G01N 33/582
USPC ............ 436/63, 164, 172; 422/92.05, 82.08; 435/4, 29, 325, 395, 288.7, 308.1
See application file for complete search history.

(56) References Cited

U.S. PATENT DOCUMENTS

| | | | |
|---|---|---|---|
| 8,838,394 B2 | 9/2014 | Kartalov et al. | |
| 8,921,102 B2 | 12/2014 | Fuchs et al. | |
| 2006/0127369 A1 | 6/2006 | Christensen et al. | |
| 2007/0238169 A1 | 10/2007 | Abilez et al. | |
| 2008/0166378 A1 | 7/2008 | Schimmer et al. | |
| 2010/0330607 A1 | 12/2010 | Trautman et al. | |
| 2011/0306086 A1 | 12/2011 | Nitta | |
| 2012/0282632 A1* | 11/2012 | Chiu ................ | G01N 33/582 435/7.23 |
| 2012/0295798 A1 | 11/2012 | Archer et al. | |
| 2013/0234067 A1 | 9/2013 | Chiu et al. | |
| 2013/0234068 A1* | 9/2013 | Chiu ................ | B82Y 30/00 252/301.35 |
| 2013/0266957 A1 | 10/2013 | Chiu et al. | |
| 2017/0003293 A1 | 1/2017 | Chiu et al. | |

FOREIGN PATENT DOCUMENTS

| | | |
|---|---|---|
| WO | WO-02096924 A1 | 12/2002 |
| WO | WO-2004028682 A2 | 4/2004 |
| WO | WO-2007118208 A2 | 10/2007 |
| WO | WO-2009107859 A2 | 9/2009 |
| WO | WO-2010104014 A1 | 9/2010 |
| WO | WO-2011057295 A2 | 5/2011 |
| WO | WO-2011057295 A3 | 9/2011 |
| WO | WO-2012054525 A2 | 4/2012 |
| WO | WO-2012071275 A2 | 5/2012 |
| WO | WO-2012071275 A3 | 7/2012 |
| WO | WO-2012054525 A3 | 8/2012 |
| WO | WO-2013101902 A2 | 7/2013 |
| WO | WO-2013116614 A1 | 8/2013 |
| WO | WO-2014058903 A2 | 4/2014 |
| WO | WO-2014058903 A3 | 6/2014 |
| WO | WO-2014138312 A1 | 9/2014 |
| WO | WO-2013101902 A3 | 1/2015 |
| WO | WO-2015081126 A1 | 6/2015 |
| WO | WO-2016161325 A1 | 10/2016 |

OTHER PUBLICATIONS

Abdelrahman, et al. Lanthanide-containing polymer microspheres by multiple-stage dispersion polymerization for highly multiplexed bioassays. J Am Chem Soc. Oct. 28, 2009;131(42):15276-83. doi: 10.1021/ja9052009.

Chen, et al. Preparation of fluorescence tunable polymer nanoparticles by one-step mini-emulsion. Journal of Macromolecular Science, Part A: Pure and Applied Chemistry. 2010; 47(11):1135-1141.

Extended European search report and opinion dated Aug. 25, 2017 for EP Application No. 14865362.9.

International search report and written opinion dated Jan. 29, 2015 for PCT/US2014/067471.

International Search Report and Written Opinion dated Jun. 24, 2016 for International PCT Patent Application No. US-2016025633.

Office action dated May 25, 2017 for U.S. Appl. No. 15/100,056.

Office action dated Jul. 7, 2017 for CN Application No. 201480074042.8.

Wang, et al., A Fluorophore-Doped Polymer Nanomaterial for Referenced Imaging of pH and Temperature with Sub-Micrometer Resolution, Adv. Funct. Mater., 2012, 22, 4202-7.

Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.

Office Action dated Jan. 3, 2018 for U.S. Appl. No. 15/100,056.

Andresen, et al. Structure and mechanism of the reversible photoswitch of a fluorescent protein. Proc Natl Acad Sci U S A. Sep. 13, 2005;102(37):13070-4. Epub Aug. 31, 2005.

Barthes, et al. Cell microenvironment engineering and monitoring for tissue engineering and regenerative medicine: the recent advances. Biomed Res Int. 2014;2014:921905. doi: 10.1155/2014/921905. Epub Jul. 20, 2014.

Bernas, et al. Loss of image quality in photobleaching during microscopic imaging of fluorescent probes bound to chromatin. J Biomed Opt. Nov.-Dec. 2005;10(6):064015.

Chan, et al. Reversible photoswitching of spiropyran-conjugated semiconducting polymer dots. Anal Chem. Nov. 6, 2012;84(21):9431-8. doi: 10.1021/ac302245t. Epub Oct. 22, 2012.

Davis, et al. Ensemble and single-particle fluorescence photomodulation in diarylethene-doped conjugated polymer nanoparticles. J. Phys. Chem. C. 2011; 115:19065-19073.

Dempsey, et al. Photoswitching mechanism of cyanine dyes. J Am Chem Soc. Dec. 30, 2009;131(51):18192-3. doi: 10.1021/ja904588g. With supplmental materials.

Emmert-Buck, et al. Laser capture microdissection. Science. Nov. 8, 1996;274(5289):998-1001.

Espina, et al. Laser-capture microdissection. Nat Protoc. 2006;1(2):586-603.

Feng, et al. Reversible photoswitching conjugated polymer nanoparticles for cell and ex vivo tumor imaging. Nanoscale. Apr. 21, 2014;6(8):4141-7. doi: 10.1039/c3nr06663k.

Feringa, et al. Chiroptical Molecular Switches. Chem Rev. May 10, 2000;100(5):1789-1816.

Gach, et al. Isolation and manipulation of living adherent cells by micromolded magnetic rafts. Biomicrofluidics. Sep. 2011;5(3):32002-3200212. doi: 10.1063/1.3608133. Epub Sep. 20, 2011.

Gunn, et al. Ferromagnetic micropallets for magnetic capture of single adherent cells. Langmuir. Nov. 16, 2010;26(22):17703-11. doi: 10.1021/la101960v. Epub Oct. 22, 2010.

Henderson, et al. Structural basis for reversible photobleaching of a green fluorescent protein homologue. Proc Natl Acad Sci U S A. Apr. 17, 2007;104(16):6672-7. Epub Apr. 9, 2007.

Herzenberg, et al. The history and future of the fluorescence activated cell sorter and flow cytometry: a view from Stanford. Clin Chem. Oct. 2002;48(10):1819-27.

Irie. Diarylethenes for Memories and Switches. Chem Rev. May 10, 2000;100(5):1685-1716.

Jeong, et al. Conjugated polymer/photochromophore binary nanococktails: bistable photoswitching of near-infrared fluorescence for in vivo imaging. Adv Mater. Oct. 18, 2013;25(39):5574-80. doi: 10.1002/adma.201301901. Epub Jul. 12, 2013.

Lee, et al. Analysis of local tissue-specific gene expression in cellular micropatterns. Anal Chem. Dec. 15, 2006;78(24):8305-12.

Lee, et al. Light-mediated spatial control via photolabile fluorescently quenched peptide cassettes. J Am Chem Soc. Feb. 10, 2010;132(5):1446-7. doi: 101021/ja907427p.

(56) References Cited

OTHER PUBLICATIONS

Lippincott-Schwartz, et al. Photobleaching and photoactivation: following protein dynamics in living cells. Nat. Cell Biol. 2003, 5, S7-S14.
Maurel, et al. Photoactivatable and photoconvertible fluorsecent probes for protein labeling. ACS Chem Biol. May 21, 2010;5(5):507-16. doi: 10.1021/cb1000229.
Metallo, et al. Engineering the stem cell microenvironment. Biotechnol Prog. Jan.-Feb. 2007;23(1):18-23.
Osakada, et al. Diarylethene doped biocompatible polymer dots for fluorescence switching. Chem Commun (Camb). Apr. 4, 2012;48(27):3285-7. doi: 10.1039/c2cc18085e. Epub Feb. 1, 2012.
Pai, et al. Efficient division and sampling of cell colonies using microcup arrays. Analyst. Jan. 7, 2013;138(1):220-8. doi: 10.1039/c2an36065a. Epub Oct. 25, 2012.
Patterson, et al. A photoactivatable GFP for selective photolabeling of proteins and cells. Science. Sep. 13, 2002;297(5588):1873-7.
Sauer. Reversible molecular photoswitches: a key technology for nanoscience and fluorescence imaging. Proc Natl Acad Sci U S A. Jul. 5, 2005;102(27):9433-4. Epub Jun. 27, 2005.
Schiro, et al. Sensitive and high-throughput isolation of rare cells from peripheral blood with ensemble-decision aliquot ranking. Angew Chem Int Ed Engl. May 7, 2012;51(19):4618-22. doi: 10.1002/anie.201108695. Epub Feb. 22, 2012.
Shadpour, et al. Sorting and expansion of murine embryonic stem cell colonies using micropallet arrays. Cytometry A. Feb. 2009;75(2):121-9. doi: 10.1002/cyto.a.20672.
Sims, et al. Choosing one from the many: selection and sorting strategies for single adherent cells. Anal Bioanal Chem. Jan. 2007;387(1):5-8.
Szymanski, et al. Reversible photocontrol of biological systems by the incorporation of molecular photoswitches. Chem Rev. Aug. 14, 2013;113(8):6114-78. doi: 10.1021/cr300179f. Epub Apr. 25, 2013.
Tse, et al. Increased asymmetric and multi-daughter cell division in mechanically confined microenvironments. PLoS One. 2012;7(6):e38986. doi: 10.1371/journal.pone.0038986. Epub Jun. 25, 2012.
Wang, et al. Array of Biodegradable Microraftsfor Isolation and Implantation of Living, Adherent Cells. RSC Adv. Jun. 28, 2013;3(24):9264-9272.
Wang, et al. Broadening cell selection criteria with micropallet arrays of adherent cells. Cytometry A. Oct. 2007;71(10):866-74.
Xu, et al. Microcup arrays for the efficient isolation and cloning of cells. Anal Chem. Apr. 15, 2010;82(8):3161-7. doi: 10.1021/ac100434v.
Zhao, et al. Method for the accurate preparation of cell-spiking standards. Anal Chem. Feb. 1, 2009;81(3):1285-90. doi: 10.1021/ac802250d.
Zhao, et al. New generation of ensemble-decision aliquot ranking based on simplified microfluidic components for large-capacity trapping of circulating tumor cells. Anal Chem. Oct. 15, 2013;85(20):9671-7. doi: 10.1021/ac401985r. Epub Oct. 2, 2013.
"CN 201480074042.8 Second Office Action dated Mar. 13, 2018 (w/ English translation)".
EP14865362 Examination Report dated Jun. 6, 2018.
European search report and opinion dated May 14, 2014 for EP Application No. 11843656.7.
European search report with written opinion dated Oct. 18, 2018 for EP Application No. 16774339.
Fernando, et al. Mechanism of cellular uptake of highly fluorescent conjugated polymer nanoparticles. Biomacromolecules. Oct. 11, 2010;11(10):2675-82. doi: 10.1021/bm1007103.
International preliminary report on patentability dated May 22, 2013 for PCT/US2011/061425.
"International Preliminary Report on Patentability written opinion dated Oct. 12, 2017 for PCT Application No. US 2016025633".
International search report and written opinion dated May 31, 2012 for PCT/US2011/061425.
Jin, et al. Near-infrared fluorescent dye-doped semiconducting polymer dots. ACS Nano. Feb. 22, 2011;5(2):1468-75. doi: 10.1021/nn103304m. Epub Jan. 31, 2011.
Office action dated Mar. 22, 2019 for U.S. Appl. No. 15/100,056.
Office action dated Jul. 16, 2018 for U.S. Appl. No. 15/100,056.
Office action dated Oct. 4, 2018 for JP Application No. 2016-534201.
Office action dated Nov. 8, 2018 for U.S. Appl. No. 15/100,056.
Wu, et al. Design of highly emissive polymer dot bioconjugates for in vivo tumor targeting. Angew Chem Int Ed Engl. Apr. 4, 2011;50(15):3430-4. doi: 10.1002/anie.201007461. Epub Mar. 4, 2011.
Wu, et al. Energy Transfer in a Nanoscale Multichromophoric System: Fluorescent Dye-Doped Conjugated Polymer Nanoparticles. Phys Chem C Nanomater Interfaces. Feb. 14, 2008;112(6):1772-1781.
Wu, et al. Preparation and encapsulation of highly fluorescent conjugated polymer nanoparticles. Langmuir. Mar. 28, 2006;22(7):2956-60.
Ye, et al. A compact and highly fluorescent orange-emitting polymer dot for specific subcellular imaging. Chem Commun (Camb). Feb. 7, 2012;48(12):1778-80. doi: 10.1039/c2cc16486h. Epub Jan. 4, 2012.

\* cited by examiner

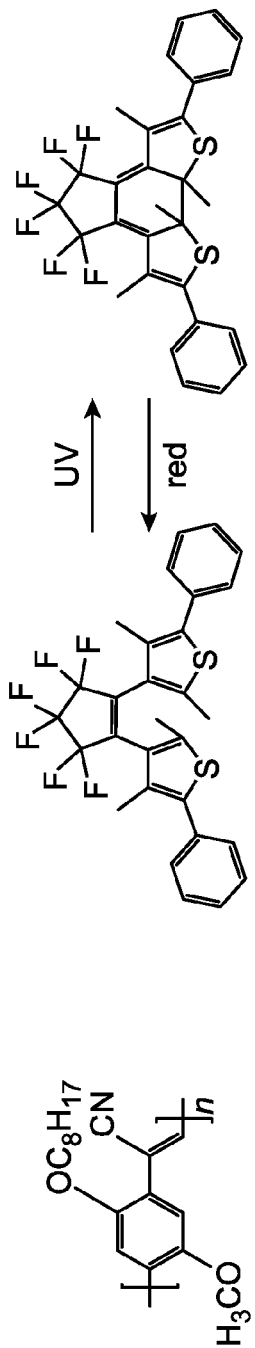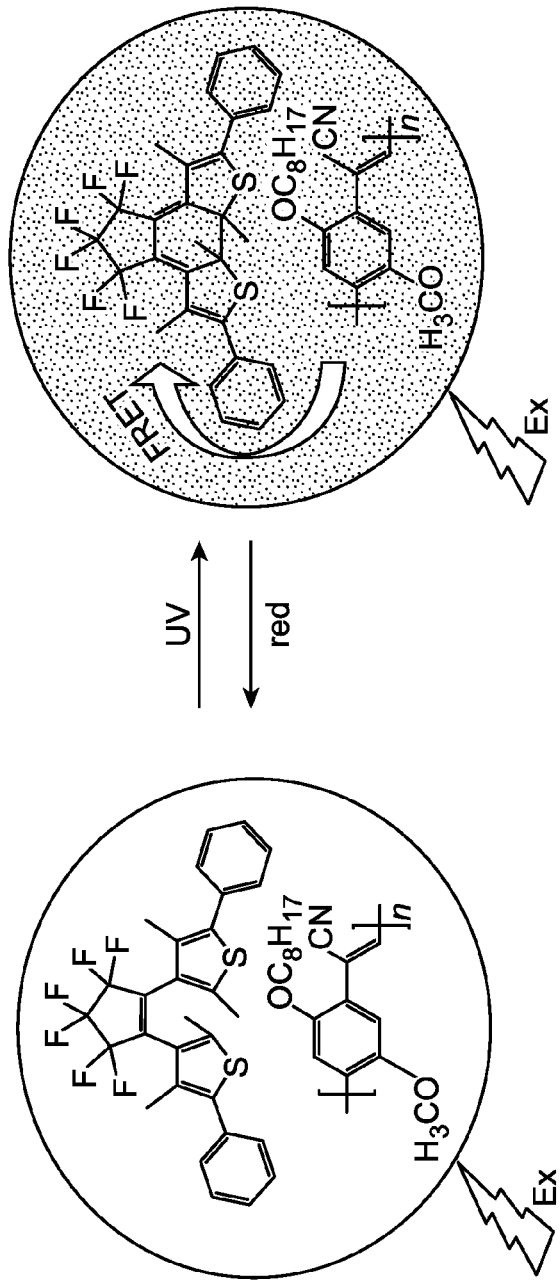
FIG. 2A
FIG. 2B
FIG. 2C

UV turn OFF red LED turn ON all cells focused 633-nm laser turn ON single cell

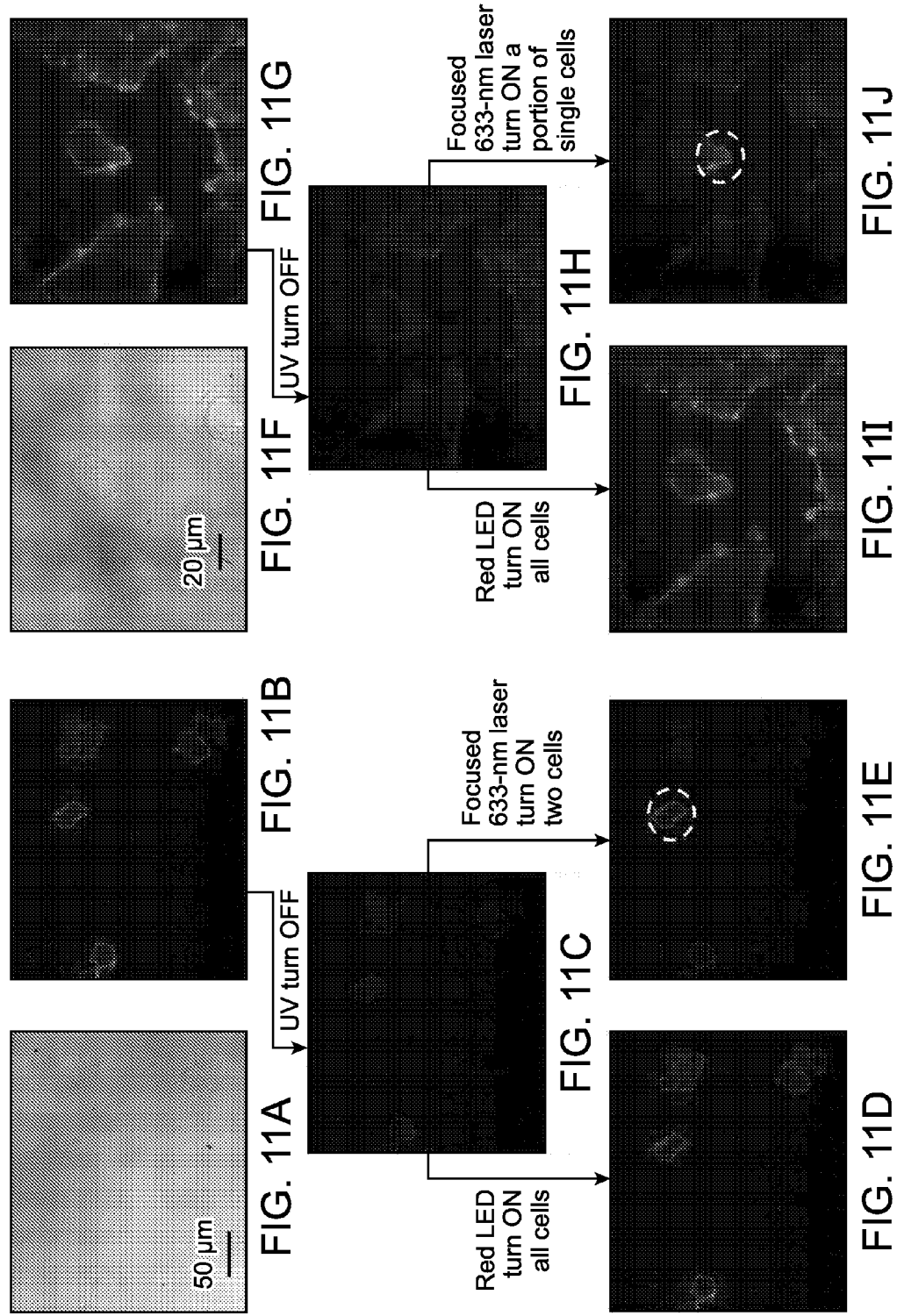

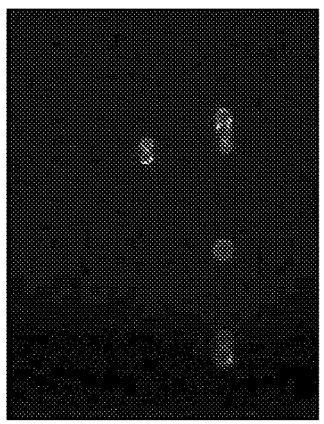
FIG. 12D
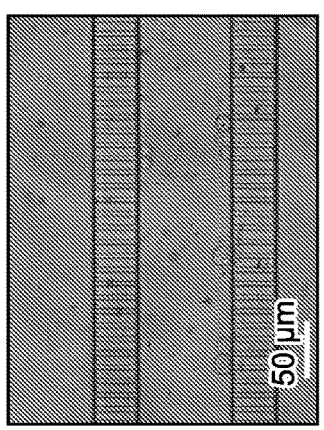
FIG. 12C
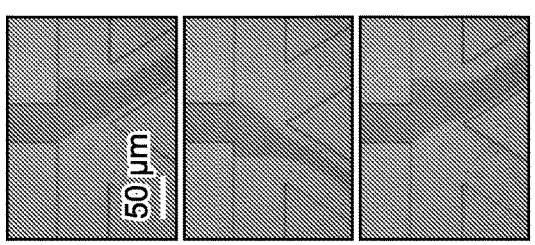
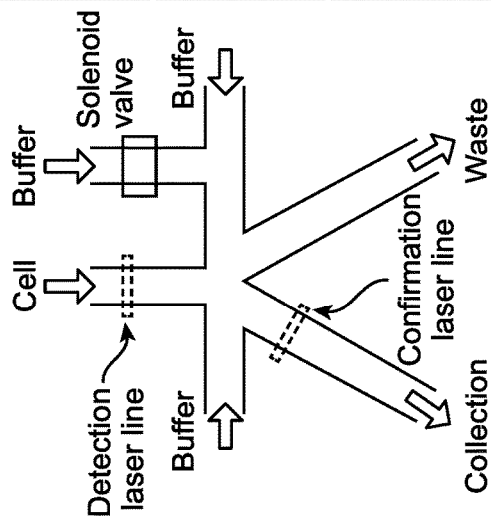
FIG. 12A
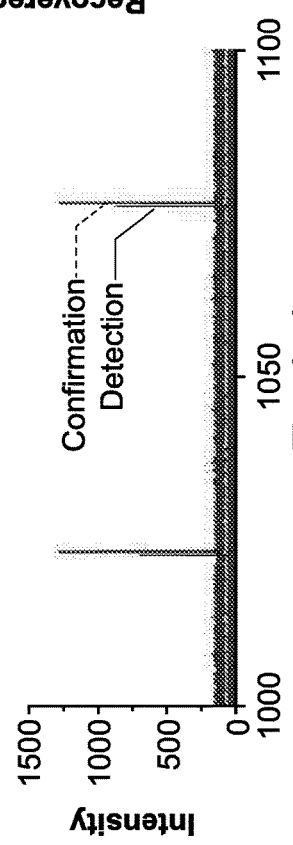
FIG. 12B
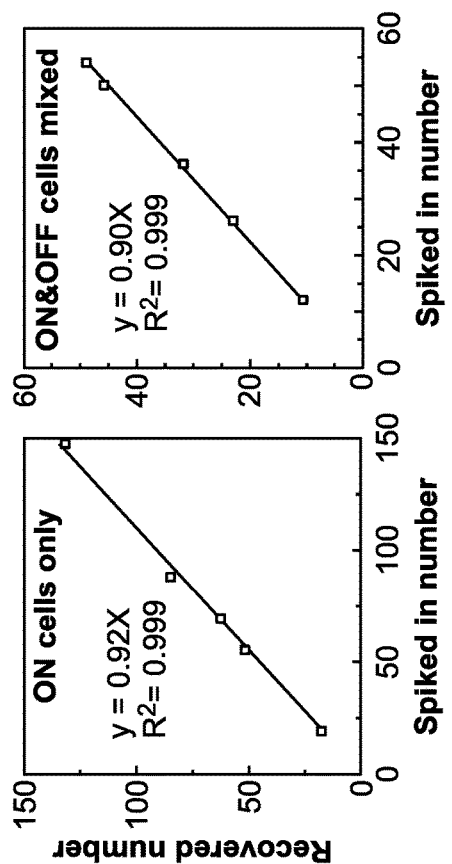
FIG. 12F
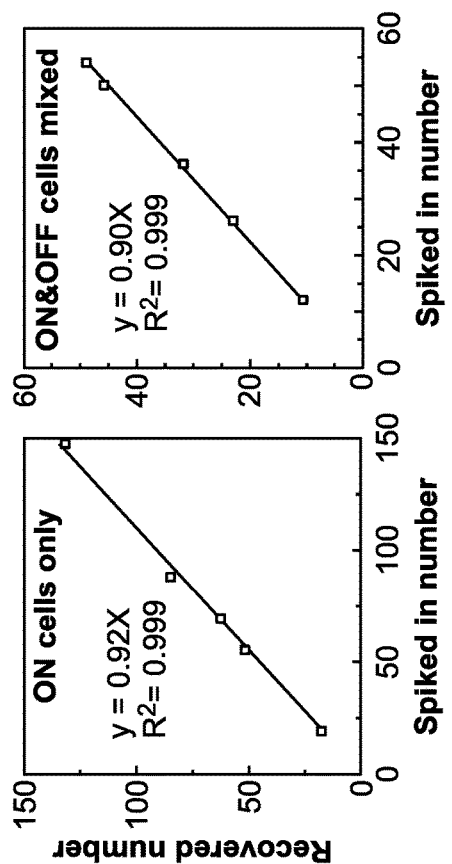
FIG. 12E

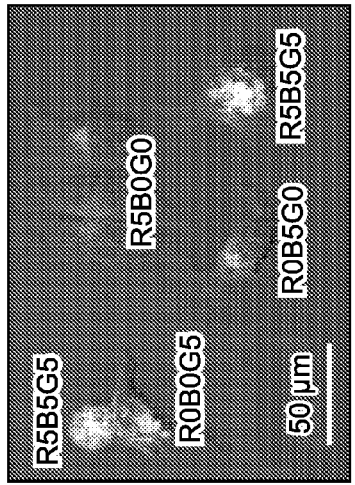
FIG. 18C
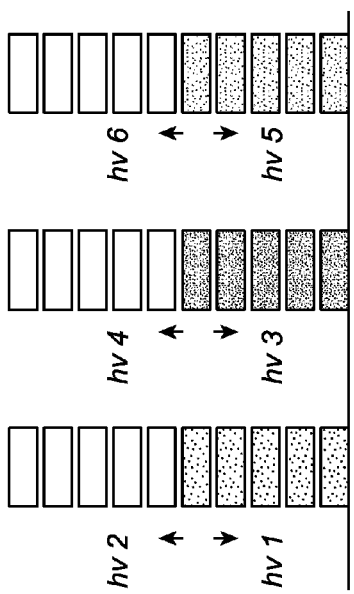
FIG. 18B
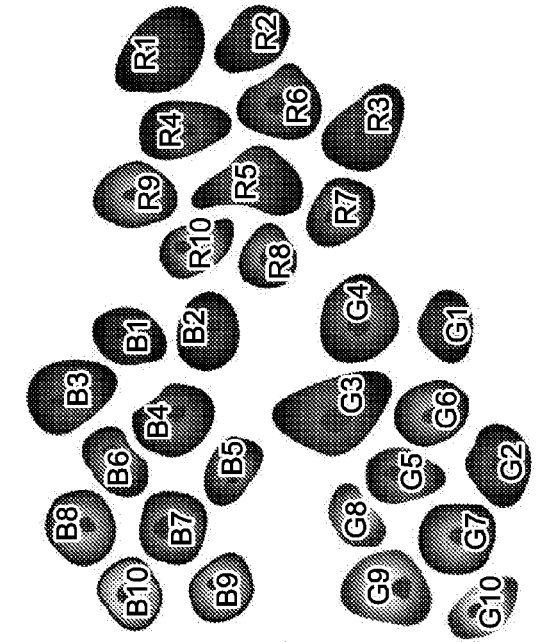
FIG. 18D
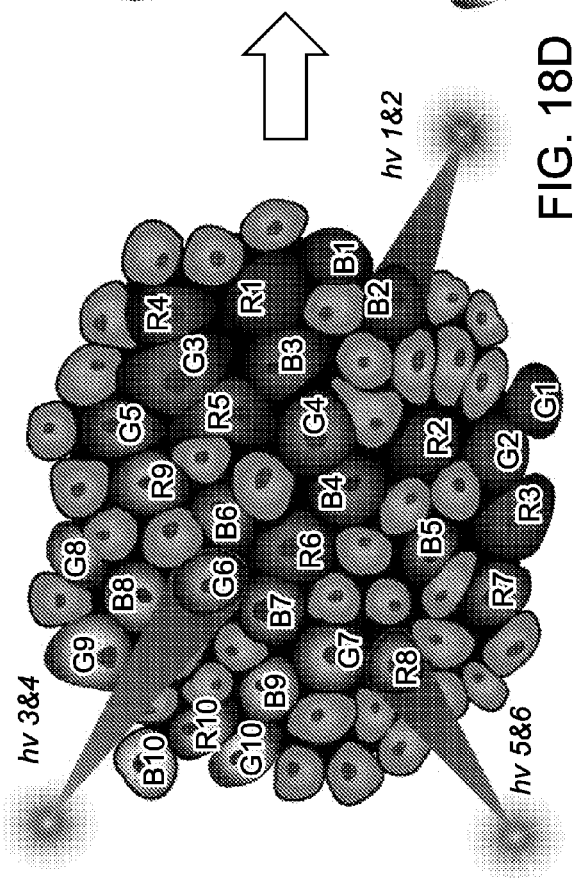

OPTICAL PAINTING AND FLUORESCENCE-ACTIVATED SORTING OF ADHERENT CELLS

CROSS-REFERENCE TO RELATED APPLICATIONS

This application is a U.S National Phase Application under 35 U.S.C. § 371 of International Application No. PCT/US2016/025633, filed Apr. 1, 2016, which claims the benefit of U.S. Provisional Application Nos. 62/142,340, filed Apr. 2, 2015, which application are incorporated herein by reference in their entireties for all purposes.

BACKGROUND

The efficient selection and isolation of cells of interest from a mixed population is important in biomedical research and biotechnology. Selected cells are often subjected to cell expansion, transplantation, and genetic analysis. Expansion of selected cells is used to create various cell lines, such as cancer, stem, and genetically engineered ones. Transplantation of cells facilitates the establishment of tumor models in laboratory animals or the repair of damaged organs. Analysis of specific cells in tissues contributes to the discovery of the biological interactions that drive diseases and aging. All these applications would benefit from the ability to select, isolate, and study individual cells in a high-throughput fashion.

Additionally, most high-throughput single-cell selection and isolation methods, such as fluorescence activated cell sorting (FACS), are designed for cells suspended in solution and cannot be used for cells that adhere to a cell-culture plate or to a tissue. Techniques such as laser capture microdissection can potentially damage or contaminate target cells.

Thus, there is a need to provide improved compositions, systems, and methods for selecting and isolating individual cells, particularly adherent cells. The present disclosure addresses this need and more.

SUMMARY

The present disclosure provides compositions, systems, and methods for optically marking and sorting cells.

In various aspects, the present disclosure provides a method of optically marking and sorting adherent cells, the method comprising: providing a plurality of adherent cells attached to a substrate, each adherent cell of the plurality of adherent cells comprising an optical marker in a first optical state, the optical marker being convertible from the first optical state to a second optical state upon application of light energy, wherein an emission intensity of the optical marker at a peak emission wavelength in the first optical state is at least 10-fold different than an emission intensity of the optical marker at the peak emission wavelength in the second optical state, and wherein the optical marker is capable of being stably maintained in the second optical state for at least 3 hours at 25° C.; selectively applying the light energy to a subset of the plurality of adherent cells while attached to the substrate, thereby selectively converting the optical markers of the subset from the first optical state to the second optical state; detaching the plurality of adherent cells from the substrate; and sorting the plurality of adherent cells based on the emission intensity of the optical marker at the peak emission wavelength.

In various aspects, the present disclosure provides a system for optically marking and sorting adherent cells, the system comprising: a plurality of adherent cells attached to a substrate, each adherent cell of the plurality of adherent cells comprising an optical marker in a first optical state, the optical marker being convertible from the first optical state to a second optical state upon application of light energy, wherein an emission intensity of the optical marker at a peak emission wavelength in the first optical state is at least 10-fold different than an emission intensity of the optical marker at the peak emission wavelength in the second optical state, and wherein the optical marker is capable of being stably maintained in the second optical state for at least 3 hours at 25° C.; a light source; one or more processors operably coupled to the light source and individually or collectively configured to cause the light source to selectively apply the light energy to a subset of the plurality of adherent cells while attached to the substrate, thereby selectively converting the optical markers of the subset from the first optical state to the second optical state; and a cell sorting device configured to sort the plurality of adherent cells when detached from the substrate based on the emission intensity of the optical marker at the peak emission wavelength.

In various aspects, the present disclosure provides a method of sorting adherent cells using optically detectable codes, the method comprising: providing a plurality of adherent cells attached to a substrate, each adherent cell of the plurality of adherent cells comprising an optical marker in a first optical state, the optical marker being convertible from the first optical state to a second optical state upon application of light energy, wherein the first optical state defines a first optically detectable code and the second optical state defines a second optically detectable code; selectively applying the light energy to a subset of the plurality of adherent cells while attached to the substrate, thereby selectively converting the optical markers of the subset from the first optical state to the second optical state; detaching the plurality of adherent cells from the substrate; and sorting the plurality of adherent cells based on whether the optical marker of each adherent cell is exhibiting the first optically detectable code or the second optically detectable code.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A illustrates the chemical structure of CN-PPV (poly[2-methoxy-5-(2-ethylhexyloxy)-1,4-(1-cyanovinylene-1,4-phenylene)]).

FIG. 2B illustrates the photochromic transition of BTE (1,2-bis(2,4-dimethyl-5-phenyl-3-thienyl)-3,3,4,4,5,5,-hexafluoro-1-cyclopentene) between the open-ring and closed-ring forms.

FIG. 2C is a schematic illustration of photoswitching of BTE-doped CN-PPV Pdots.

FIG. 9A illustrates a bright-field image of cells. FIGS. 9B through 9E illustrate fluorescence images showing the painting of all cells (FIG. 9D) or a single cell (FIG. 9E) within a population.

FIGS. 11A through 11J illustrate painting of multiple cells (FIGS. 11A through 11E) and a portion of cell (FIGS. 11F through 11J) by photoswitching.

FIG. 12A is a simple schematic illustrating the ensemble-decision aliquot ranking (eDAR) concept. The insets show the flow being switched to the collecting filter and then switched back shortly later. A food dye was added to visualize the streamline.

FIG. 12B illustrates a representative segment of the fluorescence traces recorded by the detection APD (green) and the confirmation APD (red).

FIGS. 12C and 12D illustrate bright-field and fluorescence images, respectively, of the collected cells in the filters with a 5-μm height and 5-μm width.

FIGS. 12E and 12F illustrate the recovery ratio of picking the ON-state MCF-7 cells by eDAR from a pure sample solution (FIG. 12E) and with a population of around 300 OFF-state MCF-7 cells (FIG. 12F).

FIGS. 18A through 18D illustrate the use of a spectral-intensity coding scheme to assign specific codes to a plurality of cells, thereby allowing the subsequent identification of cells or groups of cells based on their respective assigned codes.

DETAILED DESCRIPTION

Figure 1:
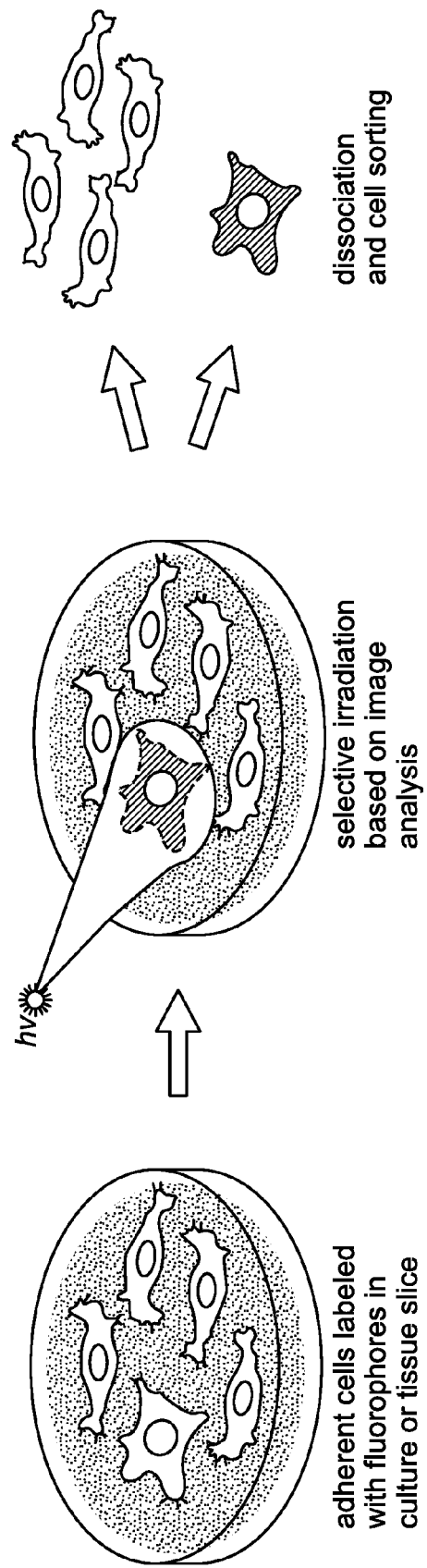
FIG. 1 is a schematic depiction of "painting" cells with light followed by the sorting and isolation of painted cells.

The present disclosure relates generally to compositions, systems, and methods for optically marking and sorting cells. In some aspects, cells are associated with an optical marker that can be converted from a first optical state to a second optical state upon the application of light energy. The first and second optical states are optically distinguishable from each other (e.g., have different optical properties), such that selective application of light energy can be used to optically mark or "paint" individual cells. In some aspects, the marked cells are subsequently differentiated and selected from unmarked cells based on the state of the optical marker, e.g., using cell sorting techniques. In various aspects, the characteristics of the optical marker are selected to ensure the marked cells can be isolated with high efficiency and recovery, e.g., the optical markers are bright, thermally stable, and offer high contrast between two optical states so the marked cells can be easily detected and distinguished from unmarked cells.

Moreover, the present disclosure enables cell isolation and selection techniques to be applied to a wider range of cell types and characteristics. Various methods can be used to select cells of interest according to their unique characteristics, such as morphology and/or biomarkers. These methods include fluorescence-activated cell sorting (FACS), limiting dilution, cloning ring, panning, column chromatography, and magnetic sorting. Among these methods, FACS, in which individual cells of interest are sorted based on the presence of fluorescent probes that target cell-specific biomarkers, is perhaps the most popular and powerful approach because it offers high-throughput and a lot of information with single-cell sensitivity. A key constraint of FACS, however, is that it can be applied only to cells suspended in solution, such as lymphocytes. In contrast, the majority of cells in the body are adherent cells that grow and function in close contact with other neighboring cells, such as in a tissue. Most cells used in biomedical research are adherent cells grown on a culture plate and attached to a surface. Adherent cells include prokaryotic or eukaryotic cells that are attached to or capable of being attached to a substrate, such as tissues (e.g., in vivo tissues, ex vivo or in vitro tissue samples), in vitro cell culture surfaces (e.g., plates, wells, flasks, scaffolds, particles), other cells (e.g., one or more cells of a tissue), or combinations thereof. In some aspects, adherent cells do not readily detach from the substrate without external intervention, such as the application of mechanical forces (e.g., scraping), chemical agents (e.g., chelating solutions such as ethylenediaminetetraacetic acid (EDTA)), enzymes (e.g., trypsin), or combinations thereof. For these cells, FACS cannot be used to select and sort them based on their morphology, location, or other features (e.g., cell-to-cell contacts, degree of crowding) when attached to a substrate. Yet, such information can be critical for the investigation of cell behaviors in their microenvironment. Accordingly, various aspects of the present disclosure provide simple and high-throughput approaches that enable individual adherent cells to be optically marked while in an adherent state (e.g., in situ within their native microenvironment), and then selected and isolated based on their optical markings.

Optical Markers for Adherent Cell Sorting

In some aspects of the present disclosure, the systems and methods provided herein utilize one or more optical markers (e.g., fluorescent markers) that are capable of being converted between two or more different optical states. In some aspects, the conversion of the optical marker is irreversible, while in other aspects, the conversion is reversible. In certain aspects, an optical marker can be converted between two or more different optical states, three or more different optical states, four or more different optical states, or five or more different optical states. Although various aspects herein are described in the context of optical markers having two different optical states, it shall be understood that the approaches presented herein are also applicable to optical markers that are convertible between more than two optical states.

In some aspects, the optical marker is controllably converted between the different optical states by application of energy, such as light energy or other types of electromagnetic radiation. In certain aspects, application of energy causes changes in the structure and/or composition of the optical marker that alters the optical characteristics of the optical marker so as to convert it to a different optical state. In certain aspects, the light energy is applied at a specific wavelength, intensity, and/or duration in order to trigger the conversion of the optical marker. Optionally, different types of light energy (e.g., light having different wavelengths, intensities, and/or durations) are applied to produce different conversions of the optical marker state. For instance, an optical marker can be converted from a first state to a second state using a first wavelength of light, from a second state to a third state using a second wavelength of light, and so on. As another example, an optical marker can be converted from a first state to a second state using a first wavelength of light, and converted from the second state back to the first state using a second wavelength of light. In alternative aspects, conversion is caused by mechanisms other than application of energy, e.g., thermal reversion.

In certain aspects, the optical marker exhibits different optical characteristics (e.g., emission spectrum, absorbance spectrum, peak emission wavelength(s), peak excitation wavelength(s), emission intensities, emission lifetimes, emission rates) when in different optical states. For instance, an optical marker may have a first emission spectrum when in one optical state and a second emission spectrum when in a different optical state. As another example, an optical marker can be converted from a first state to a second state using a first wavelength of light of one intensity, from a second state to a third state using the first wavelength of light of a different intensity. The use of different wavelengths of light and also different intensities of light can be used in combination to convert between multiple optical marker states. As yet another example, the emission intensity of an optical marker at a peak emission wavelength may vary depending on the current optical state, such that the emission intensity is relatively high in certain states and is relatively low in other states. Accordingly, the current optical state of the optical marker can be determined by measuring one or more optical characteristics of the marker (e.g., emission intensity at a peak emission wavelength). The optical state can thus serve as a basis for optically marking and differentiating individual cells.

FIG. 1 schematically illustrates a strategy for optically marking and sorting adherent cells using convertible optical markers, in accordance with various aspects of the present disclosure. A plurality of adherent cells are provided in an adherent state, e.g., attached to a substrate. Each adherent cell includes one or more optical markers configured to be converted from a first optical state (e.g., designated as the unmarked or "OFF" state) to a second optical state (e.g., designated as the marked or "ON" state) upon application of light energy. In some aspects, the optical markers of the plurality of adherent cells are all initially in the same optical state (e.g., the first optical state). In other aspects, the states of the optical markers are initially mixed, with some being in the first optical state and others being in the second optical state.

Optical marking is performed by selectively exposing a subset of the plurality of adherent cells (e.g., one or more cells of interest) to light energy (e.g., a focused laser beam) while attached to the substrate in order to convert their respective optical markers from the first optical state to the second optical state. For example, a selected subset of a plurality of unmarked or OFF cells can be converted to the marked or ON state. In alternative aspects where the first optical state represents the ON state, application of light energy can be used to "unmark" cells. Optionally, in aspects where the conversion of the optical marker is reversible, a second, different light energy can be applied to revert cells from the second optical state to the first optical state, e.g., to correct inadvertent marking of unwanted cells. In some aspects, the light energy is applied to a single cell of the subset at a time. In other aspects, the light energy is applied to multiple cells of the subset at a time, e.g., two or more cells, three or more cells, four or more cells, five or more cells, six or more cells, seven or more cells, eight or more cells, nine or more cells, ten or more cells, twenty or more cells, thirty or more cells, forty or more cells, fifty or more cells, sixty or more cells, seventy or more cells, eighty or more cells, ninety or more cells, 100 or more cells, 200 or more cells, or 500 or more cells at a time.

In certain aspects, the adherent cells are examined by optical imaging (e.g., microscopy) while attached to the substrate in order to visualize and select the subset to be optically marked, e.g., manually by a user and/or automatically using image analysis algorithms. In certain aspects, the subset is selected based on characteristics of the cells that are exhibited when in the adherent state, such as spatial features (e.g., location, position relative to other cells, cell-cell contacts) and/or morphological features (e.g., shape, size). Following the optically marking procedure, the adherent cells are detached from the substrate and sorted in order to separate selected cells from unmarked cells, e.g., via downstream FACS analysis and isolation. Thus, the present disclosure enables adherent cells to be marked and sorted based on characteristics exhibited when in their native environment.

Various aspects of the present disclosure provide optical markers having characteristics that are advantageous for efficient and accurate marking and sorting of adherent cells. Examples of such characteristics include but are not limited to: (1) high brightness so the optically marked cells can be easily detected and recovered; (2) high contrast between the first and second optical states so the marked cells can be accurately distinguished from unmarked cells; (3) high absorption cross-section so the labeled cells can be easily marked without requiring intense energy application; (4) good stability (e.g., thermostability) so the marked cells do not spontaneously decay back to the unmarked state, or vice-versa; (5) a rapid conversion rate so individual cells can be optically marked in a high-throughput fashion; (6) the capacity to be converted with red or near-infrared light to avoid cell damage and for increased penetration depth (e.g., for marking cells located deep in a tissue); (7) low photobleaching rate; and/or (8) good fatigue resistance for multiple switching cycles. In certain aspects, the optical markers described in the present disclosure include some or all of these characteristics.

For instance, the present disclosure provides in some aspects optical markers exhibiting a first emission intensity at a peak emission wavelength when in a first optical state, and a second, different emission intensity at the peak emission wavelength when in the second optical state. In certain aspects, the peak emission wavelength is within a range from about 200 nanometers to about 300 nanometers, about 250 nanometers to about 350 nanometers, about 300 nanometers to about 400 nanometers, about 350 nanometers to about 450 nanometers, about 400 nanometers to about 500 nanometers, about 450 nanometers to about 550 nanometers, about 500 nanometers to about 600 nanometers, about 550 nanometers to about 650 nanometers, about 600 nanometers to about 700 nanometers, about 650 nanometers to about 750 nanometers, about 700 nanometers to about 800 nanometers, about 750 nanometers to about 850 nanometers, about 800 nanometers to about 900 nanometers, about 850 nanometers to about 950 nanometers, about 900 nanometers to about 1000 nanometers, about 950 nanometers to about 1050 nanometers, about 1000 nanometers to about 1100 nanometers, about 1150 nanometers to about 1250 nanometers, or about 1200 nanometers to about 1300 nanometers.

In various aspects, the ratio of the emission intensity of the optical marker at the peak emission wavelength in the first optical state to the emission intensity of the optical marker at the peak emission wavelength in the second optical state, also referred to herein as the "contrast ratio," is sufficiently large so as to allow the two optical states to be accurately differentiated from each other. In certain aspects, the emission intensity of the optical marker at the peak emission wavelength in the first optical state is at least 2-fold, 3-fold, 4-fold, 5-fold, 6-fold, 7-fold, 8-fold, 9-fold, 10-fold, 20-fold, 50-fold, 75-fold, 100-fold, 150-fold, 200-fold, 300-fold, 400-fold, 500-fold, 600-fold, 700-fold, 800-fold, 900-fold, or 1000-fold different than the emission intensity of the optical marker at the peak emission wavelength in the second optical state. In certain aspects, the emission intensity of the optical marker at the peak emission wavelength in the first optical state is at least 2 times, 3 times, 4 times, 5 times, 6 times, 7 times, 8 times, 9 times, 10 times, 20 times, 50 times, 75 times, 100 times, 150 times, 200 times, 300 times, 400 times, 500 times, 600 times, 700 times, 800 times, 900 times, or 1000 times greater than the emission intensity of the optical marker at the peak emission wavelength in the second optical state. In other aspects, the emission intensity of the optical marker at the peak emission wavelength in the first optical state is at least 2 times, 3 times, 4 times, 5 times, 6 times, 7 times, 8 times, 9 times, 10 times, 20 times, 50 times, 75 times, 100 times, 150 times, 200 times, 300 times, 400 times, 500 times, 600 times, 700 times, 800 times, 900 times, or 1000 times less than the emission intensity of the optical marker at the peak emission wavelength in the second optical state. In various aspects, a relatively large contrast ratio reduces the risk of false positives or false negatives when differentiating marked cells from unmarked cells.

As another example, some aspects of the present disclosure provide optical markers exhibiting sufficient stability for cell sorting and analysis, e.g., are capable of being stably maintained in the first and/or second optical states for an extended period of time without reverting to another state (e.g., due to thermal reversion). In various aspects, stability of the optical marker is advantageous in ensuring that marked and unmarked cells remain distinguishable throughout the cell sorting procedure. In some aspects, a population of optical markers is considered to be "stable" or "stably maintained" in an optical state if at least 90%, at least 95%, at least 99%, at least 99.5% or at least 99.95% of the cells in the population are maintained in the optical state for the specified time period. In some aspects, an optical marker is considered to be stable or stably maintained in an optical state if the time constant (e.g., time to decay to 1/e of the initial value) of the reversion rate is at least about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 24 hours, about 36 hours, about 48 hours, about 60 hours, about 72 hours, about 84 hours, about 96 hours, or more. In some aspects, at the time of analysis (e.g., sorting), at least 90%, at least 95%, at least 99%, at least 99.5% or at least 99.95% of the optical markers associated with the cell is stable or stably maintained in the desired optical state.

In some aspects, the optical marker is capable of being stably maintained in the first optical state for at least about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 24 hours, about 30 hours, about 36 hours, about 40 hours, about 48 hours, about 50 hours, about 60 hours, about 72 hours, about 84 hours, about 96 hours, about 100 hours, about 150 hours, about 200 hours, about 250 hours, about 300 hours, about 400 hours, or about 500 hours at a specified temperature. In some aspects, the optical marker is capable of being stably maintained in the second optical state for at least about 3 hours, about 4 hours, about 5 hours, about 6 hours, about 7 hours, about 8 hours, about 9 hours, about 10 hours, about 20 hours, about 30 hours, about 40 hours, about 50 hours, about 100 hours, about 150 hours, about 200 hours, about 250 hours, about 300 hours, about 400 hours, or about 500 hours at a specified temperature. In various aspects, the specified temperature is about 4° C., about 5° C., about 10° C., about 15° C., about 25° C., about 30° C., about 35° C., about 37° C., about 40° C., about 45° C., or about 50° C. In other aspects, the specified temperature is within a range from about 4° C. to about 25° C., or from about 25° C. to about 40° C.

In some aspects of the present disclosure, the optical marker is selected or designed to exhibit narrow band emission properties at the peak emission wavelength so as to reduce or minimize overlap with other markers or labels. For example, in certain aspects, the optical marker has a peak emission bandwidth (e.g., full width at half maximum (FWHM) of the emission peak) of no more than about 5 nanometers, about 10 nanometers, about 15 nanometers, about 20 nanometers, about 25 nanometers, about 30 nanometers, about 35 nanometers, about 40 nanometers, about 45 nanometers, about 50 nanometers, about 60 nanometers, about 70 nanometers, about 80 nanometers, about 90 nanometers, or about 100 nanometers.

In some aspects of the present disclosure, the optical marker is reversibly converted or convertible from the first optical state to the second optical state, while in other aspects, the optical marker is irreversibly converted or convertible from the first optical state to the second optical state. In certain aspects where the optical marker is reversibly convertible, different types of light energy (e.g., two different wavelengths of light) are used to convert the marker from the first state to the second state and vice-versa. In certain aspects, reversibly convertible optical markers exhibit relatively high fatigue resistance, e.g., are capable of being converted between the two optical states multiples times while exhibiting minimal or no photobleaching, photodegradation, etc. Various aspects of the present disclosure provide optical markers that are capable of being converted between two optical states at least 3 times, 5 times, 10 times, 20 times, 50 times, or more.

In some aspects, the optical marker is selected or designed to be converted from the first optical state to the second optical state following exposure to one or more wavelengths of light energy, e.g., ultraviolet light, infrared light, near-infrared light, visible light, or combinations thereof. In certain aspects, the light energy has a wavelength within a range from about 200 nanometers to about 300 nanometers, about 250 nanometers to about 350 nanometers, about 300 nanometers to about 400 nanometers, about 350 nanometers to about 450 nanometers, about 400 nanometers to about 500 nanometers, about 450 nanometers to about 550 nanometers, about 500 nanometers to about 600 nanometers, about 550 nanometers to about 650 nanometers, about 600 nanometers to about 700 nanometers, about 650 nanometers to about 750 nanometers, about 700 nanometers to about 800 nanometers, about 750 nanometers to about 850 nanometers, about 800 nanometers to about 900 nanometers, about 850 nanometers to about 950 nanometers, about 900 nanometers to about 1000 nanometers, about 950 nanometers to about 1050 nanometers, about 1000 nanometers to about 1100 nanometers, about 1150 nanometers to about 1250 nanometers, or about 1200 nanometers to about 1300 nanometers.

The wavelength of light energy used to convert the optical markers can be selected based on certain criteria. In some aspects, the wavelength of the light energy is selected to minimize or reduce damage to cells (e.g., has a longer wavelength than blue or ultraviolet light). In some aspects, the wavelength of the light energy is selected to be different from a peak excitation wavelength of the optical marker and/or other markers used to label the cells (e.g., is away from and/or does not overlap with excitation wavelengths for commonly used fluorophores). In some aspects, the wavelength of the light energy is selected to enhance penetration into tissue (e.g., red or infrared light wavelengths). Some examples of suitable wavelengths include: wavelengths greater than or equal to about 300 nm, about 350 nm, about 400 nm, about 450 nm, about 500 nm, about 550 nm, about 650 nm, about 700 nm, about 750 nm, about 800 nm, about 850 nm, about 900 nm, about 950 nm, about 1000 nm, about 1050 nm, or about 1100 nm.

In some aspects, it is desirable to minimize or reduce the power and/or duration of the light energy applied to convert the optical markers, e.g., to avoid stress or damage to cells, photobleaching of the markers, increase marking throughput and efficiency, etc. For instance, in certain aspects, the light energy is applied for no more than about 0.1 milliseconds, about 0.5 milliseconds, about 1 millisecond, about 5 milliseconds, about 10 milliseconds, about 50 milliseconds, 0.1 seconds, about 0.25 seconds, about 0.5 seconds, about 1 second, about 5 seconds, about 10 seconds, about 20 seconds, about 0.5 minutes, about 1 minutes, about 5 minutes, or about 10 minutes to convert the optical marker from the first optical state to the second optical state. In certain aspects, the light energy is applied with a power of no more than about 1 µW, about 10 µW, about 20 µW, about 40 µW, about 50 µW, about 75 µW, about 100 µW, about 200 µW, about 300 µW, about 400 µW, about 500 µW, about 750 µW, about 1 mW, or about 10 mW to convert the optical marker from the first optical state to the second optical state. In various aspects, the duration and power of light application are dependent on each other, e.g., low power is associated with longer durations, while high power is associated with shorter durations.

Some aspects of the present disclosure provide optical markers suitable for optical multiplexing and/or encoding. In certain aspects, each cell is labeled with a plurality of different types of the optical markers described herein, such as at least two, at least three, at least four, at least five, at least six, at least seven, at least eight, at least nine, at least 10, at least 20, at least 50, at least 100, at least 200, at least 300, at least 400, at least 500, or at least 1000 different types of optical markers. Each optical marker type has different optical properties, e.g., different emission spectra, peak emission wavelengths, peak excitation wavelengths, etc. In certain aspects, each optical marker type exhibits narrow band emission properties at its peak emission wavelength, so as to minimize overlap with the peak emission wavelengths of other optical markers. In certain aspects, encoding is achieved via spectral-intensity encoding, as described further herein.

In some aspects, each of the different optical marker types is convertible from a first respective optical state (e.g., OFF state) to a second respective optical state (e.g., ON state) upon application of light energy, as described herein. In certain aspects, different light energies (e.g., different wavelengths of light) are applied to convert different optical marker types, so as to enable certain optical markers to be selectively converted without influencing the state of other markers. In some aspects, the ON optical states of the various optical marker types are distinguishable from each other, e.g., have different peak emission wavelengths.

Optionally, the OFF optical states are also optically distinguishable from each other. Accordingly, this approach permits different subsets of cells to be optically marked with different combinations of ON and OFF markers, such that each unique combination can be used to represent a different optical encoding. In the case of spectral-intensity encoding, the ON and OFF markers also can have different intensity levels (accomplished, for example, by illuminating with light of different intensities or over different durations). Cells marked in this manner can be further analyzed and/or isolated based on their respective optical encodings, thus providing a multiplexed sorting scheme for adherent cells.

In some aspects of this multiplexed encoding, each cell can be marked with a unique optical code (e.g. spectral-intensity). Each cell can be dispensed into a microwell or a droplet (e.g. generated with droplet microfluidic technology) for subsequent optical identification and then single-cell analysis. Because each optical code marks the properties of the adherent cell in a tissue prior to dissociation into a suspension of cells, the result of single-cell analysis can be directly correlated with the properties of the cell in the tissue, including but not limited to spatial, and/or temporal, and/or morphology, and/or phenotypic, and/or appearance, and/or physiological properties of the cell.

Optical Marker Compositions

Various types of optical markers are suitable for use with the methods and systems of the present disclosure, including but not limited to dyes, stains, proteins, polymers, beads, particles, or combinations thereof. In some aspects, the optical marker includes one or more chromophores (e.g., fluorophores). The chromophores described herein can be used to produce optical state conversions according to various mechanisms. In some aspects, converting the optical marker from the first optical state to the second optical state comprises photobleaching one or more chromophores. In other aspects, converting the optical marker from the first optical state to the second optical state comprises Förster resonance energy transfer (FRET)-based quenching of one or more chromophores, or removal of FRET-based quenching of one or more chromophores. In certain aspects, the application of light energy triggers a compositional and/or structural change in an entity that interacts with the chromophore. For example, in some aspects, the optical marker includes at least one photochromic molecule that is converted (e.g., reversibly or irreversibly) to a different composition and/or structure upon exposure to light energy. Optionally, the photochromic molecule is a photochromic quencher that controllably quenches the fluorescence of the chromophore, depending on the conformation of the molecule, thereby producing a change in the optical state of the optical marker. Examples of photochromic molecules include but are not limited to azobenzenes, stilbenes, azostilbenes, diarylethenes, quinones, nitrones, fulgides, or derivatives or combinations thereof. 1,2-bis(2,4-dimethyl-5-phenyl-3-thienyl)-3,3,4,4,5,5,-hexafluoro-1-cyclopentene (BTE) is an example of a diarylethene suitable for use in accordance with various aspects presented herein. In some aspects, BTE exhibits improved photoswitching kinetics, thermal stability, and fatigue resistance compared to other types of photochromic molecules.

In some aspects, the chromophore itself undergoes a change in structure and/or composition when exposed to light energy which alters the optical properties of the chromophore. For example, in some aspects, an optical marker includes at least one photoactivatable chromophore that is irreversibly converted from a first optical state (e.g., exhibiting relatively low or no fluorescence) to a second optical state (e.g., exhibiting relatively high fluorescence) upon application of light energy. Examples of photoactivatable chromophores include but are not limited to photoactivatable green fluorescent protein (PA-GFP), PA-CFP2, PA-mRFP1, PA-mCherryl, Phamret, caged fluorescent dyes (e.g., 5-carboxymethoxy-2-nitrobenzyl (CMNB)-caged fluorescein, CMNB-caged carboxylfluorescein), or combinations or derivatives thereof. In some aspects, a photoactivatable fluorescent protein is capable of being genetically encoded and expressed in cells, as described further herein.

In some aspects, an optical marker includes at least one photoswitchable chromophore that is reversibly convertible between a first optical state (e.g., exhibiting relatively low or no fluorescence) and a second optical state (e.g., exhibiting relatively high fluorescence). In certain aspects, a photoswitchable chromophore is converted from a first optical state to a second optical state when exposed to a first light energy (e.g., a first wavelength of light), and from the second optical state to the first optical state when exposed to a second, different light energy (e.g., a second wavelength of light). Optionally, a photoswitchable chromophore is capable of being reversibly switched between the two optical states multiple times with minimal or no photobleaching, e.g., at least 3 times, 5 times, 10 times, 20 times, 50 times, or more. Examples of photo switchable chromophores include but are not limited to Dronpa, rsFastLime, Padron, bsDronpa, E2GFP, rsCherry, rsCherryRev, or combinations or derivatives thereof. In other aspects, an optical marker includes at least one photoswitchable chromophoric polymer particle, as described further herein.

In some aspects, an optical marker includes at least one photoconvertible chromophore that is reversibly or irreversibly convertible between a first state exhibiting a first peak emission wavelength and a second state exhibiting a second, different peak emission wavelength. In certain aspects, the first and second peak emission wavelengths differ by at least 5 nanometers, by at least 10 nanometers, by at least 20 nanometers, by at least 30 nanometers, by at least 40 nanometers, by at least 50 nanometers, by at least 60 nanometers, by at least 70 nanometers, by at least 80 nanometers, by at least 90 nanometers, by at least 100 nanometers, by at least 200 nanometers, by at least 300 nanometers, by at least 400 nanometers, or by at least 500 nanometers. Examples of photoswitchable chromophores include but are not limited to Kaede, wtKikGR, mKikGR, wtEosFP, dEos, tdEos, mEos2, Dendra2, or combinations or derivatives thereof. Optionally, certain aspects of the chromophores described herein are both photoconvertible and photo switchable, such as IrisFP.

Chromophoric Polymer Particles as Optical Markers

In some aspects, an optical marker includes at least one chromophoric polymer particle (also known as "polymer dot" or "Pdot") comprising one or more polymers (e.g., semiconducting polymers, non-semiconducting polymers, or a combination thereof) that have been collapsed into a stable sub-micron-sized particle. Chromophoric polymer particles are advantageous in certain aspects compared to other types of chromophores for several reasons: (1) they are extremely bright, up to 30 times brighter than quantum dots, and exceptionally photostable; (2) they have fast photo-emission rates, often with sub-nanosecond lifetimes so they are well-suited for flow-based applications such as FACS; (3) they possess good biocompatibility and are not composed of cytotoxic heavy metals like quantum dots; (4) they exhibit amplified energy transfer so their fluorescence emission can be well-modulated, e.g., by photochromic molecules via energy transfer.

Various structures and compositions of chromophoric polymer particles are applicable to the aspects presented herein. The chromophoric polymer particles provided herein are made up of a single polymer or, alternatively, comprise blends of polymers. In certain aspects, the one or more polymers are collapsed, precipitated, and/or condensed to form a polymer matrix. In some aspects, the properties of the chromophoric polymer particle are dependent on the structure and/or properties of the constituent polymer(s). Therefore, the polymer backbone (main chain), side chains, terminal units, and substituted groups are varied in certain aspects to obtain specific properties. In some aspects, the optical properties of the chromophoric polymer particle are tuned by varying the structures of the polymer backbone (main chain).

In some aspects, the chromophoric polymer particles provided herein include one or more chromophores, also referred to herein as chromophoric units. In certain aspects, a chromophore absorbs certain wavelengths of light, e.g., from the UV region to the near infrared region, and may be or may not be emissive. In some aspects, a chromophoric unit includes, but is not limited to, a unit of structures with delocalized pi-electrons, a unit of small organic dye molecules, and/or a unit of metal complexes. In various aspects, the chromophore is part of the polymer matrix or is incorporated into the polymer matrix, e.g., by blending, cross-linking, and the like.

In certain aspects, the chromophoric polymer particles of the present disclosure include one or more chromophoric polymers. In some aspects, a chromophoric polymer includes at least a portion which absorbs certain wavelengths of light, e.g., ranging from UV to near infrared spectra. Chromophoric polymers according to the present disclosure may be or may not be emissive. In some aspects, a chromophoric polymer includes one or more chromophoric units. Examples of chromophoric polymers include but are not limited to polymers comprising units of structures with delocalized pi-electrons (e.g., semiconducting polymers), polymers comprising units of small organic dye molecules, polymers comprising units of metal complexes, and polymers comprising units of any combinations thereof. In some aspects, the chromophoric unit is incorporated into the polymer backbone. In some aspects, the chromophoric unit is covalently attached to the side chain, or the terminal unit of the polymer. Chromophoric polymers are made using standard synthesis methods generally well known in the art, in certain aspects.

Various types of chromophoric polymer particles are suitable for use as a platform for the optical marking approaches of the present disclosure. Chromophoric polymer particles can adopt a variety of configurations, including but not limited to a monolithic polymer particle having a uniform, homogenous composition or a polymer particle having a distinct core and cap structure. The chromophoric polymer particles provided herein can be formed by any method known in the art, including, without limitation, methods relying on precipitation, methods relying on the formation of emulsions (e.g., mini or micro emulsion), and methods relying on condensation. Examples of chromophoric polymer particles suitable for use with the techniques described herein can be found in, for example, PCT application numbers PCT/US2010/056079, PCT/US2012/071767, PCT/US2011/056768, PCT/US2013/024300, and PCT/US2013/063917 and in U.S. Patent Publication No. 2013/0266957, each of which is incorporated herein by reference.

In some aspects, the chromophoric polymer particle is a nanoparticle. In some aspects, the sizes of the nanoparticles provided herein are defined in terms of a "critical dimension," which refers to the smallest dimension of the nanoparticle. Some nanoparticles are roughly spherical in shape, which results in the critical dimension being the diameter of the spherical particle. In some aspects, certain nanoparticles, such as nanospheres and nanocubes, are completely nanoscopic in size. In some aspects, not every dimension of a nanoparticle is at the nanoscale. For example, a nanocylinder can have a diameter on the nano-scale but a length on the micro-scale. A wide variety of nanoparticle shapes are applicable to the aspects described herein, including but not limited to a sphere, a cylinder, an ellipsoid, a polyhedron, a prism, a rod, a wire, or combinations thereof. The shape of the nanoparticle contributes to the optical properties in certain aspects, as will be appreciated by those of skill in the art (e.g., nano-rods may have different optical properties than nano-spheres).

In some aspects, the typical size of a chromophoric polymer particle is fewer than 100 nanometers. In certain aspects, a colloidal polymer nanoparticle is composed of a lyophobic polymer interior. Optionally, polyelectrolytes can also be formed into nanoparticles. In certain aspects, the chromophoric polymer particle comprises at least one chromophoric polymer that has been formed into a stable particle. The particle size can vary from 5 nanometers to 500 nanometers. In some aspects, the critical dimension (e.g., diameter) of the particle is less than 500 nanometers, less than 400 nanometers, less than 300 nanometers, less than 200 nanometers, less than 100 nanometers, less than 50 nanometers, less than 40 nanometers. In some aspects, the critical dimension of the particle is less than 30 nanometers, less than 20 nanometers, or less than 10 nanometers.

In some aspects, the chromophoric polymer particles described herein include a polymer matrix formed from one or more chromophoric polymers. Any suitable number and combination of chromophoric polymer types can be incorporated in the chromophoric polymer particles described herein, such as one or more chromophoric polymers, two or more chromophoric polymers, three or more chromophoric polymers, four or more chromophoric polymers, five or more chromophoric polymers, six or more chromophoric polymers, seven or more chromophoric polymers, eight or more chromophoric polymers, nine or more chromophoric polymers, ten or more chromophoric polymers, fifty or more chromophoric polymers, or one hundred or more chromophoric polymers. The mass concentration of the chromophoric polymers relative to the entire chromophoric polymer particle mass can be varied from 1% to 99%, 10% and 99%, 20% and 99%, 30% and 99%, 40% and 99%, or 50% and 99%.

Various types and compositions of chromophoric polymers are applicable for use in accordance with aspects of the present disclosure. The chromophoric polymer can be a homopolymer or a heteropolymer. In various aspects, the chromophoric polymer is a semiconducting polymer, a non-semiconducting polymer, or a combination thereof. For example, a number of semiconducting polymers are suitable for use in chromophoric polymer particles according to the present disclosure. Examples of semiconducting polymers include but are not limited to: polyfluorene polymers, including but not limited to poly(9,9-dihexylfluorenyl-2,7-diyl) (PDHF) and poly(9,9-dioctylfluorenyl-2,7-diyl) (PFO); fluorene-based copolymers, including but not limited to, poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4-benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), and poly[(9,9-dioctylfluorenyl-2,7-diyl)-co-(4,7-Di-2-thienyl-2,1,3-benzothiadiazole)] (PF-0.1TBT); phenylene vinylene polymers, including but not limited to, poly[2-methoxy-5-(2-ethylhexyloxy)-1,4-phenylenevinylene] (MEH-PPV) and poly[2-methoxy-5-(2-ethylhexyloxy)-1,4-(1-cyanovinylene-1,4-phenylene)] (CN-PPV); phenylene ethynylene polymers, including but not limited to, poly(2,5-di(3',7'-dimethyloctyl)phenylene-1,4-ethynylene (PPE); or a combination thereof.

A wide variety of chromophoric polymer structures are suitable for use in accordance with various aspects of the present disclosure. In some aspects, the chromophoric polymer is a linear polymer. In other aspects, the chromophoric polymer is a branched polymer. In certain aspects, the chromophoric polymer is a dendrimer. In certain aspects, the chromophoric polymer is a brush polymer. In certain aspects, the chromophoric polymer is a star polymer.

In some aspects, the chromophoric polymer particles described herein contain a polystyrene-based, comb-like polymer. Non-limiting examples of polystyrene based comb-like polymers include polystyrene graft acrylic acid, polystyrene graft ethylene oxide, polystyrene graft butyl alcohol, and the like. In some aspects, chromophoric polymer particles described herein contain poly(methyl methacrylate) based comb-like polymers. Non-limiting examples of poly(methyl methacrylate) based comb-like polymers include, poly(methyl methacrylate) graft acrylic acid, poly(methyl methacrylate) graft ethylene oxide, and the like. In some aspects, chromophoric polymer particles described herein contain a comb-like polymer comprising carboxyl, amine, thiol, ester, succinimidyl ester, azide, alkyne, cyclooctyne, or phosphine groups.

In some aspects, the chromophoric polymer particles described herein contain a polymer functionalized on the terminal monomeric unit, for example with a carboxyl, amine, thiol, ester, succinimidyl ester, azide, alkyne, cyclooctyne, phosphine, or similar functional group. Examples of such polymers include but are not limited to poly(meth)acrylate polymers, polyacrylamide polymers, polyisobutylene, polydiene, polyphenylene, polyethylene, poly(ethylene glycol), polylactide, polystyrene, polysiloxane, poly(vinyl pyridine), poly(vinylpyrrolidone), polyurethane, a block copolymer thereof, a random or alternating copolymer thereof, and the like.

In some aspects, the chromophoric polymer particles described herein contain a copolymer having one or more functionalized monomeric units, for example an amphiphilic polymer, including but not limited to: poly((meth)acrylic acid)-based copolymers such as: poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid); polydiene-based copolymers such as: poly(butadiene(1,2 addition)-b-ethylene oxide), poly(butadiene(1,2 addition)-b-methylacrylic acid, poly(butadiene(1,4 addition)-b-acrylic acid), poly(butadiene(1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly(isoprene-b-ethylene oxide), and poly(isoprene-b-N-methyl 2-vinyl pyridinium iodide); poly(ethylene oxide)-based copolymers such as: poly(ethylene oxide-b-acrylic acid), poly(ethylene oxide-b-acrylamide), poly(ethylene oxide-b-butylene oxide), poly(ethylene oxide-b-c-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-b-t-butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline); polyisobutylene-based copolymers such as poly(isobutylene-b-acrylic acid), poly(isobutylene-b-ethylene oxide), poly(isobutylene-b-methacrylic acid); polystyrene based copolymers such as poly(styrene-b-acrylamide), poly(styrene-b-acrylic acid), poly(styrene-b-cesium acrylate), poly(styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly(styrene-b-sodium acrylate) poly(styrene-b-sodium methacrylate), polyp-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate); polysiloxane-based copolymers such as poly(dimethylsiloxane-b-acrylic acid), poly(dimethylsiloxane-b-ethylene oxide), poly(dimethylsiloxane-b-methacrylic acid); poly(ferrocenyldimethylsilane) based copolymers such as poly(ferrocenyldimethylsilane-b-ethylene oxide); poly(2-vinyl naphthalene)-based copolymers such as poly(2-vinyl naphthalene-b-acrylic acid), poly(vinyl pyridine and N-methyl vinyl pyridinium iodide)-based copolymers such as poly(2-vinyl pyridine-b-ethylene oxide), poly(-vinyl pyridine-b-methyl acrylic acid), poly(N-methyl 2-vinyl pyridinium iodide-b-ethylene oxide), poly(N-methyl 4-vinyl pyridinium iodide-b-methyl methacrylate), poly(4-vinyl pyridine-b-ethylene oxide) PEO end functional OH; and poly(vinyl pyrrolidone)-based copolymers such as poly(vinyl pyrrolidone-b-DIL-lactide); and the like.

In some aspects of the present disclosure, the chromophoric polymer particles provided herein include the polymer CN-PPV, also known as poly[2-methoxy-5-(2-ethylhexyloxy)-1,4-(1-cyanovinylene-1,4-phenylene)], which is a bright, compact, and orange-emitting semiconducting polymer particle. In certain aspects, CN-PPV has superior fluorescence properties, such as a large absorption cross-section, high quantum yield, and a fast emission rate. In some aspects, the chromophoric polymer particle comprises a polymer that consists essentially of CN-PPV. In some aspects, the particle includes CN-PPV and at least one other material. For example, the CN-PPV can be mixed with a copolymer or other material that provides an additional functionality.

In some aspects, the chromophoric polymer particles of the present disclosure include a semiconducting copolymer having at least two different chromophoric units. For example, a conjugated copolymer can contain both fluorene and benzothiazole chromophoric units present at a given ratio. Typical chromophoric units used to synthesize semiconducting copolymers include, but are not limited to fluorene unit, phenylene vinylene unit, phenylene unit, phenylene ethynylene unit, benzothiazole unit, thiophene unit, carbazole fluorene unit, boron-dipyrromethene unit, and derivatives thereof. The different chromophoric units can be segregated, as in a block copolymer, or intermingled. In some aspects, a chromophoric copolymer is represented by writing the identity of the major chromophoric species. For example, PFBT is a chromophoric polymer containing fluorene and benzothiazole units at a certain ratio. In some cases, a dash is used to indicate the percentage of the minor chromophoric species and then the identity of the minor chromophoric species. For example, PF-0.1 BT is a chromophoric copolymer containing 90% PF and 10% BT.

In certain aspects, the chromophoric polymer particle includes a blend of semiconducting polymers. The blends can include any combination of homopolymers, copolymers, and oligomers. Polymer blends used to form chromophoric polymer particles may be selected in order to tune the properties of the resulting polymer particles, for example, to achieve a desired excitation or emission spectra for the polymer particle.

In various aspects of the present disclosure, semiconducting chromophoric polymer particles offer improved detection sensitivity in part because they exhibit higher quantum yields than other fluorescent reporters. In some aspects, the quantum yield of the chromophoric polymer particle used is more than 5%, more than 10%, more than 20%, more than 30%, more than 40%, more than 50%, more than 60%, more than 70%, more than 80%, or more than 90%. In various aspects, semiconducting chromophoric polymer particles offer improved detection sensitivity in part because they exhibit large absorption cross sections. In various aspects, semiconducting chromophoric polymer particles offer improved detection sensitivity in part because they exhibit faster emission rates than other fluorescent reporters. In certain aspects, the emission rate of the chromophoric polymer particle used is between about 100 picoseconds and about 50 nanoseconds.

In some aspects, the chromophoric polymer particle herein include polymers bearing units of small organic dye molecules, metal complexes, photochromic dye, and any combinations thereof, for example, optically inactive polymers such as polystyrene covalently linked or grafted with small organic dye, metal complexes, photochromic dyes, or any combination thereof. In some aspects, the chromophoric polymer particles comprise semiconducting polymers covalently linked with small organic dye molecules, metal complexes, photochromic dyes, or any combinations thereof as emissive units. Such emissive units can tune the emission color, increase the quantum yield, and improve the photostability of the chromophoric polymer particle. In some aspects, the small organic dyes, or metal complexes have sensing functions, and therefore add additional functionalities to the chromophoric polymer particle, such as protein sensing capability.

In some aspects, the chromophoric polymer particle comprises a semiconducting polymer physically mixed or chemically cross-linked with other chromophoric polymers, such as optically inactive polymers covalently linked or grafted with small organic dye, metal complexes, photochromic dyes, or any combination thereof, to have additional functionalities such as protein sensing.

In some aspects, the chromophoric polymer particle includes semiconducting polymers physically mixed or chemically cross-linked with other components such as fluorescent dyes, inorganic luminescent materials, magnetic materials, metal materials, and the like in order to tune emission color, improve quantum yield and/or photo stability, and/or provide additional functionalities such as magnetic functions, plasmon resonance functions, and the like.

The optical properties, such as absorption wavelength, for a given chromophoric polymer particle can be tuned by modifying its composition and/or structure. Semiconducting polymers have been developed with absorption wavelengths ranging from UV to infrared, including the entire visible spectrum. In some aspects, chromophoric polymer particles having a peak absorption wavelength between about 200 nanometers and about 300 nanometers, about 250 nanometers and about 350 nanometers, about 300 nanometers and about 400 nanometers, about 350 nanometers and about 450 nanometers, between about 400 nanometers and about 500 nanometers, about 450 nanometers and about 550 nanometers, about 500 nanometers and about 600 nanometers, about 550 nanometers and about 650 nanometers, about 600 nanometers and about 700 nanometers, about 650 nanometers and about 750 nanometers, about 700 nanometers and about 800 nanometers, about 750 nanometers and about 850 nanometers, about 800 nanometers and about 900 nanometers, about 850 nanometers and about 950 nanometers, or about 900 nanometers and about 1000 nanometers, are used.

Semiconducting polymers have been developed with emission wavelengths ranging from UV to infrared, including the entire visible spectrum. In some aspects, chromophoric polymer particles having a peak emission wavelength between about 200 nanometers and about 300 nanometers, about 250 nanometers and about 350 nanometers, about 300 nanometers and about 400 nanometers, about 350 nanometers and about 450 nanometers, about 400 nanometers and about 500 nanometers, about 450 nanometers and about 550 nanometers, about 500 nanometers and about 600 nanometers, about 550 nanometers and about 650 nanometers, about 600 nanometers and about 700 nanometers, about 650 nanometers and about 750 nanometers, about 700 nanometers and about 800 nanometers, about 750 nanometers and about 850 nanometers, about 800 nanometers and about 900 nanometers, about 850 nanometers and about 950 nanometers, about 900 nanometers and about 1000 nanometers, about 950 nanometers and about 1050 nanometers, about 1000 nanometers and about 1100 nanometers, about 1150 nanometers and about 1250 nanometers, or about 1200 nanometers and about 1300 nanometers, are used.

In some aspects, the present disclosure provides chromophoric polymer particles with narrow-band emissions. Narrow-band emissions are advantageous for certain applications, including but not limited to multiplexing applications as described further herein. The emission wavelength of the polymer particles can vary from ultraviolet to near infrared region. In some aspects, the FWHM of the emission band is less than about 70 nanometers, about 65 nanometers, about 60 nanometers, about 55 nanometers, about 50 nanometers, about 45 nanometers, about 40 nanometers, about 35 nanometers, about 30 nanometers, about 25 nanometers, about 20 nanometers, or about 10 nanometers. In some aspects, the FWHM of the polymer particles described herein can range between about 5 nanometers to about 70 nanometers, from about 10 nanometers to about 60 nanometers, from about 20 nanometers to about 50 nanometers, or from about 30 nanometers to about 45 nanometers.

In some aspects, the variety of chromophoric polymer particles of the present disclosure include polymers that have a narrow band emissive unit (e.g., a narrow band monomer and/or a narrow band unit). For example, the present disclosure can include a homopolymer or heteropolymer including a narrow band monomer, such as BODIPY and/or BODIPY derivative monomer, a squaraine and/or squaraine derivative monomer, a metal complex and/or metal complex derivative monomer, a porphyrin and/or porphyrin derivative monomer, a metalloporphyrin and/or metalloporphyrin derivative monomer, a phthalocyanine and/or phthalocynanine derivative monomer, a lanthanide complex and/or lanthanide complex derivative monomer, a perylene and/or perylene derivative monomer, a cyanine and/or cyanine derivative monomer, a rhodamine and/or rhodamine derivative monomer, a coumarin and/or coumarin derivative monomer, and/or a xanthene and/or xanthene derivative monomer. In certain aspects, a narrow band unit is, e.g., a narrow band monomer or a fluorescent nanoparticle embedded in or attached to the polymer particle. The fluorescent nanoparticle can be, e.g., a quantum dot. Optionally, a narrow band unit includes a polymer or fluorescent dye molecule that gives a narrow emission in a polymer particle of the present disclosure.

In some aspects, the chromophoric polymer particles described herein are photoswitchable chromophoric polymer particles. Various approaches can be used to produce photoswitchable polymer particles. In some aspects, the particle includes one or more photoswitchable chromophores, e.g., a photoswitchable chromophoric polymer, a photoswitchable chromophore, or combinations thereof. For example, in certain aspects, a photoswitchable chromophoric polymer particle includes a chromophoric polymer having one or more photoswitchable chromophoric units. As another example, in certain aspects, a photoswitchable chromophoric polymer particle includes one or more photoswitchable chromophores embedded in the polymer matrix of the particle.

In some aspects, a photoswitchable chromophoric polymer particle includes one or more of the chromophoric polymers described herein and at least one entity that interacts with the chromophoric polymer(s) to produce photoswitching behavior between first and second optical states. For example, in certain aspects, a photoswitchable chromophoric polymer particle includes a polymer matrix comprising a chromophore, such as a chromophoric polymer, and a photochromic molecule. As described above, the photochromic molecule can be an azobenzene, stilbene, azostilbene, spiropyran, spirooxazine, diarylethene (e.g., BTE), quinone, nitrone, fulgide, napthopyran, silver halide, zinc halide, or derivatives or combinations thereof. In various aspects, the photochromic molecule has one or more absorbance bands or peaks that overlap substantially with one or more emission bands or peaks of the chromophoric polymer when in a first optical state. In certain aspects, in the first optical state, there is energy transfer (e.g., FRET) between the chromophoric polymer and the photochromic molecule, and in the second optical state, there is substantially no energy transfer between the chromophoric polymer and the photochromic molecule. Accordingly, in certain aspects, the photochromic molecule quenches fluorescence of the chromophoric polymer when in the first optical state, and there is substantially no fluorescence quenching of the chromophoric polymer by the photochromic molecule when in the second optical state. In other aspects, a photoswitchable chromophoric polymer particle includes a chromophore (e.g., coupled to and/or embedded in the polymer matrix), and a photochromic molecule that interacts with the chromophore to produce photoswitching behavior.

Although certain aspects herein are described in the context of photoswitchable chromophoric polymer particles, it shall be understood that such aspects can also be applied to photoactivatable or photoconvertible chromophoric polymer particles. For example, in some aspects, a photoactivatable chromophoric polymer particle includes at least one photoactivatable chromophoric polymer, at least one photoactivatable chromophore, and/or a photochromic molecule that interacts with a chromophore or chromophoric polymer to produce photoactivation. Similarly, in some aspects, a photoconvertible chromophoric polymer particle includes at least one photoconvertible chromophoric polymer, at least one photoconvertible chromophore, and/or a photochromic molecule that interacts with a chromophore or chromophoric polymer to produce photoconversion.

Optical Encoding Using Optical Markers

Certain aspects of the present disclosure provide optical markers suitable for use as an optical encoding platform. In some aspects, an optical marker is capable of being converted between two or more optical states upon application of energy (e.g., light energy), and each optical state defines a different optically detectable code for the optical marker. Such optical markers may be referred to herein as "encoded optical markers." In certain aspects, an optical marker is capable of being converted between a plurality of different optical states that each define a different optical code, such that the optical marker is capable of exhibiting at least two different optical codes, at least three different optical codes, at least four different optical codes, at least five different optical codes, at least six different optical codes, at least seven different optical codes, at least eight different optical codes, at least nine different optical codes, at least 10 different optical codes, at least 20 different optical codes, at least 30 different optical codes, at least 40 different optical codes, at least 50 different optical codes, at least 60 different optical codes, at least 70 different optical codes, at least 80 different optical codes, at least 90 different optical codes, at least 100 different optical codes, at least 200 different optical codes, at least 500 different optical codes, at least 1000 different optical codes, at least 10,000 different optical codes, or at least 100,000 different optical codes. In certain aspects, switching between different optical codes is achieved by applying different light energies to the optical marker. In various aspects, application of different light energies involves applying light having different wavelengths, light having different intensities, or combinations thereof. Alternatively or in combination, application of different light energies involves applying light energy to the optical marker for different amounts of time.

Figure 15:
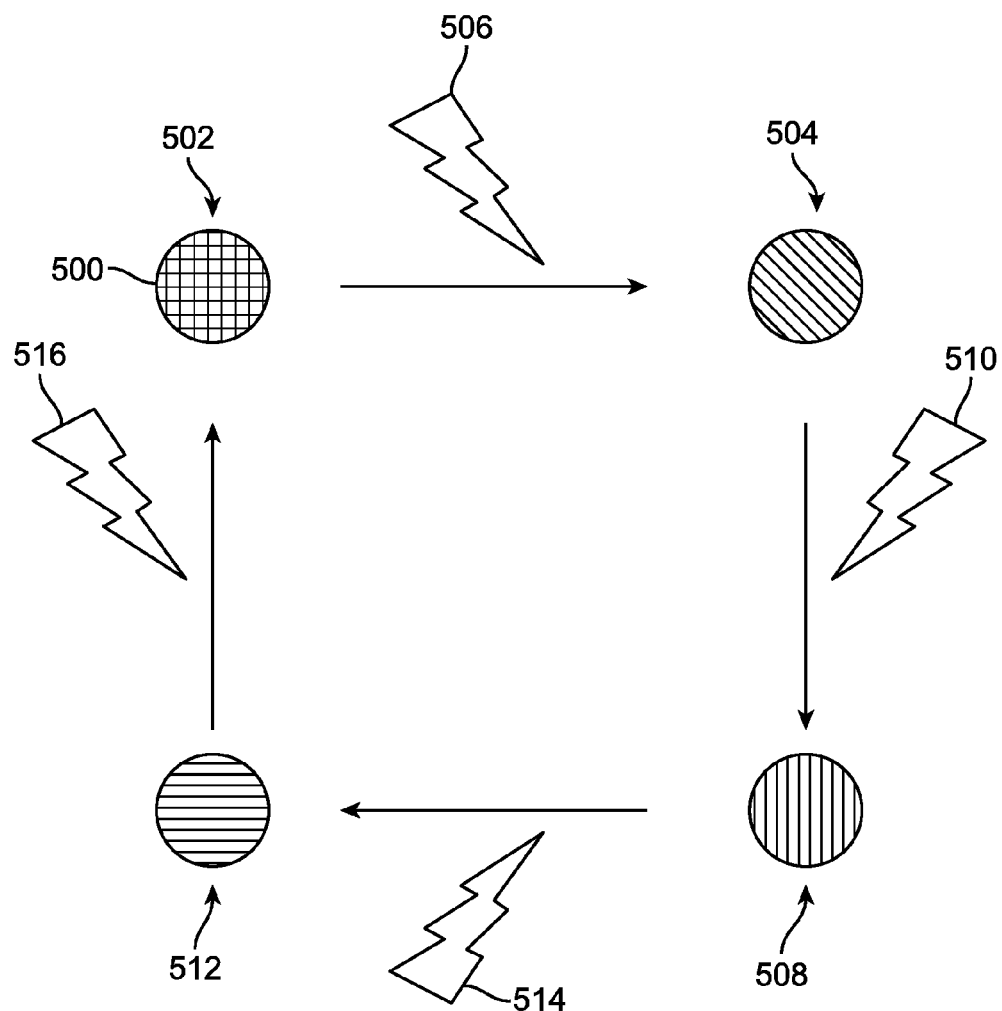
FIG. 15 illustrates a multi-color photoswitching scheme for optical encoding.

FIG. 15 illustrates a multi-color scheme for optical encoding using photoswitching optical markers. In the depicted embodiment, an optical marker 500 is converted from a first optical state 502 to a second optical state 504 by application of a first light energy 506, from the second optical state 504 to a third optical state 508 by application of a second light energy 510, from the third optical state 508 to a fourth optical state 512 by application of a third light energy 514, and from the fourth optical state 512 to the first optical state 502 by application of a fourth light energy 516. In some aspects, each optical state defines a different optically detectable code for the optical marker 500. For example, in certain aspects, the optical marker 500 exhibits a different color (e.g., peak emission wavelength) when in different optical states, with each color representing a different code.

In some aspects, adherent cells can be marked and sorted using the encoding schemes described herein by providing each cell with an optical marker that exhibits different optically detectable codes upon application of different light energies, as described herein. Light energy can be selectively applied to certain cells in order to mark the cells with a desired optically detectable code. The cells can then be collected and sorted based on the exhibited optically detectable code.

In some aspects, cells marked using the encoding scheme can be dispensed directly into single-cell compartments, where each compartment contains predominantly no more than one cell. An example of compartments can be microwells, in which each cell is dispensing into a microwell; if dispensing is random following Poisson statistics, then each well would most often contain one or no cell. Another example of compartments can be droplets created using droplet microfluidics, in which each cell is contained in a droplet; if cell encapsulation follows Poisson statistics, then each droplet can most frequently contain one cell or no cell. After single-cell compartments, a wide range of single-cell analysis maybe performed, including but not limited to single-cell PCR, single-cell RNA-seq, single-cell genotyping, single-cell sequencing, single-cell genetic analysis, single-cell digital ELISA, single-cell assays, single-cell imaging, single-cell functional studies, single-cell-omics analysis (e.g. metabolomics, genomics, lipidomics, proteomics), or single-cell culture. Regardless of the method of single-cell compartmentalization or single-cell analysis, each optical code marks the properties of the adherent cell in a tissue prior to dissociation of tissue into a suspension of cells, and thus the result of single-cell analysis can be directly correlated with the properties of the cell in the tissue via the optical code, including but not limited to spatial, and/or temporal, and/or morphology, and/or phenotypic, and/or appearance, and/or physiological properties of the cell. The optical code can be read out by a wide range of methods, including imaging (e.g. fluorescence imaging) or flow-based optical detection. This procedure allows the results of each holder's single-cell analysis to be correlated to a particularly-identified cell (or group of cells) of the original plurality of cells. Because cells marked with an optical code may be identified in such a manner, the dispensing of cells into single-cell holders, such as microwells or droplets, constitutes an implicit sorting of the cells. Accordingly, as used herein, sorting of cells includes single-cell dispensing of marked cells into holders, allowing them to be identified based on their markings.

As described herein, in some aspects, the optical marker exhibits different optical properties (e.g., emission spectrum, absorbance spectrum, peak emission wavelength(s), peak excitation wavelength(s), emission intensities, emission lifetimes, emission rates) when in different optical states. In certain aspects, an optically detectable code is defined by one or more optical properties of the optical marker when in a certain optical state. Accordingly, an encoded optical marker can be uniquely identified by detecting its optical state (e.g., by measuring its optical properties) in order to determine the corresponding code.

The optical properties used to define optically detectable codes are also referred to herein as "optical coding parameters" or "tunable optical coding parameters." An encoded optical marker can include any number and combination of tunable optical coding parameters used to define optical codes. In some aspects, a set of tunable optical coding parameters of an optical marker includes only a single tunable optical coding parameter. In other aspects, a set of tunable optical coding parameters includes at least two unique tunable optical coding parameters, at least three unique tunable optical coding parameters, at least four unique tunable optical coding parameters, at least five unique tunable optical coding parameters, at least six unique tunable optical coding parameters, at least seven unique tunable optical coding parameters, at least eight unique tunable optical coding parameters, at least nine unique tunable optical coding parameters, at least ten unique tunable optical coding parameters, at least twenty unique tunable optical coding parameters, at least fifty unique tunable optical coding parameters, or at least one hundred unique tunable optical coding parameters.

In certain aspects, at least some of the tunable optical coding parameters of an optical marker are independently or semi-independently tunable or modulatable by application of different light energies. In some aspects, "tuned independently" means that one tunable optical coding parameter is not affected by another tunable optical coding parameter (e.g., one set of emission peaks is not affected by another set of emission peaks). In some aspects, "tuned semi-independently" means that one tunable optical coding parameter can be affected by another tunable optical coding parameter (e.g., one set of emission peaks can be affected by another set of emission peaks). For example, in some aspects, two or more tunable optical coding parameters, three or more or more tunable optical coding parameters, four or more tunable optical coding parameters, five or more tunable optical coding parameters, six or more tunable optical coding parameters, seven or more tunable optical coding parameters, eight or more tunable optical coding parameters, nine or more tunable optical coding parameters, ten or more tunable optical coding parameters, twenty or more tunable optical coding parameters, fifty or more tunable optical coding parameters, or one hundred or more tunable optical coding parameters are independently or semi-independently tunable or modulatable.

The optically detectable code of an encoded optical marker can be defined based on any suitable number and combination of tunable optical coding parameters. In some aspects, the optically detectable code is defined according to a single tunable optical coding parameter (e.g., emission peak wavelength only ("wavelength encoding" or "spectral encoding"), emission peak intensity only ("intensity encoding"), emission lifetime only ("lifetime encoding"), etc.) In other aspects, the optically detectable code is defined according to two tunable optical coding parameters (e.g., emission peak wavelength and emission peak intensity ("wavelength-intensity encoding" or "spectral-intensity encoding"), emission peak wavelength and emission lifetime ("wavelength-lifetime encoding" or "spectral-lifetime encoding"), emission peak intensity and emission lifetime ("intensity-lifetime encoding"). In alternative aspects, the optically detectable code is defined according to three tunable optical coding parameters (e.g., emission peak wavelength, emission peak intensity, and emission lifetime ("wavelength-intensity-lifetime encoding" or "spectral-intensity-lifetime encoding"). In some aspects, the optically detectable code is defined according to four tunable optical coding parameters, five tunable optical coding parameters, six tunable optical coding parameters, seven tunable optical coding parameters, eight tunable optical coding parameters, nine tunable optical coding parameters, ten tunable optical coding parameters, or more than ten tunable optical coding parameters.

In certain aspects, an optically detectable code is defined based on the set of emission peaks of the encoded optical marker when in a certain optical state. In some aspects, the encoded optical marker comprises at least two distinct chromophores (e.g., at least two different types of chromophoric polymers) which produce at least two sets of emission peaks for the optical marker. In some aspects, the encoded optical markers have at least two sets, at least three sets, at least four sets, at least five sets, at least six sets, at least seven sets, at least eight sets, at least nine sets, or at least ten sets of emission peaks generated by a corresponding number of chromophores.

In some aspects, the optical marker can have multiple, e.g., 2-10, sets of well-resolved emission peaks, in which any two neighboring emission peaks do not have spectral overlap. The intensity levels of each emission peak can be tuned independently by application of different light energies. However, in certain aspects, the optical marker can have multiple emission peaks, and there may be some spectral overlap between two neighboring emission peaks. In some aspects, the overlapped area is less than 1% of the integrated area of any one of the two neighboring peaks. In some aspects, the overlapped area is less than 5% of the integrated area of any one of the two neighboring peaks. In some aspects, the overlapped area is less than 10% of the integrated area of any one of the two neighboring peaks. In some aspects, the overlapped area is less than 20% of the integrated area of any one of the two neighboring peaks. In some aspects, the overlapped area is less than 30% of the integrated area of any one of the two neighboring peaks. In some aspects, the overlapped area is less than 40% of the integrated area of any one of the two neighboring peaks.

In some aspects, the encoded optical marker can have multiple, e.g., 2-10, sets of emission peaks, and each peak originates from one chromophore (e.g., a fluorescent species) in the marker. In certain aspects, the intensity levels of each emission peak can be tuned independently, e.g., by application of light energy with different wavelengths, application of light energy with different wavelengths, application of light energy for different amounts of time, or combinations thereof. In certain aspects, the optical marker can have multiple emission peaks, but two or more than two emission peaks can originate from one chromophore species and the other emission peaks are from different species. The intensity levels of the emission peaks from one chromophore species can be correlated and tuned by application of different light energies.

In some aspects, the optical marker shows multiple, e.g., 2-10, sets of emission peaks under one-wavelength excitation. In some aspects, the optical marker shows multiple sets of emission peaks under two-wavelength excitation. In some aspects, the optical marker shows multiple sets of emission peaks under three-wavelength excitation. In some aspects, the optical marker shows multiple sets of emission peaks under four- or more-wavelength excitation. However, the emission intensity of each set of emission peaks can be independently or semi-independently tuned by applying different light energies, e.g., the relative intensity of one set of emission peak or peaks versus any of other peaks can be changed independently or semi-independently.

In certain aspects, the emission intensities and/or emission wavelengths of the set of emission peaks of an encoded optical marker can be modulated via exposure to light, thereby allowing for encoding based on peak wavelength and/or intensity. For example, in some aspects, a wavelength encoding scheme provides a plurality of optically detectable codes defined by varying the emission wavelength of the emission peaks of the encoded optical marker. The emission wavelength of the optical markers can vary from the UV region to the near infrared region. In some aspects, the emission wavelength of each set of emission peak or peaks of the optical marker is capable of being modulated independently or semi-independently. The emission intensity of each set of emission peak or peaks of the marker can be tuned and adjusted independently or semi-independently. In some aspects, the optical markers include two sets of emission peaks where their wavelengths can be independently or semi-independently tuned. In some aspects, the optical markers include three sets of emission peaks where their wavelengths can be independently or semi-independently tuned. In some aspects, the optical markers include four sets of emission peaks where their wavelengths can be independently or semi-independently tuned. In some aspects, the optical markers include five sets of emission peaks where their wavelengths can be independently or semi-independently tuned. In some aspects, the optical markers include six sets of emission peaks where their wavelengths can be independently or semi-independently tuned. In some aspects, the optical markers include more than six sets of emission peaks where their wavelengths can be independently or semi-independently tuned. In some aspects, the optical markers include up to ten sets of emission peaks where their wavelengths can be independently or semi-independently tuned. In some aspects, the optical markers include more than ten sets of emission peaks where their wavelengths can be independently or semi-independently tuned.

In some aspects, an intensity encoding scheme provides a plurality of optically detectable codes defined by varying the emission intensity levels of the emission peaks of the encoded optical marker via application of different light energies. In some aspects, the optical markers include two sets of emission peaks where their intensity levels can be independently or semi-independently tuned. In some aspects, the optical markers include three sets of emission peaks where their intensity levels can be independently or semi-independently tuned. In some aspects, the optical markers include four sets of emission peaks where their intensity levels can be independently or semi-independently tuned. In some aspects, the optical markers include five sets of emission peaks where their intensity levels can be independently or semi-independently tuned. In some aspects, the optical markers include six sets of emission peaks where their intensity levels can be independently or semi-independently tuned. In some aspects, the optical markers include more than six sets of emission peaks where their intensity levels can be independently or semi-independently tuned. In some aspects, the optical markers include up to ten sets of emission peaks where their intensity levels can be independently or semi-independently tuned. In some aspects, the optical markers include more than ten sets of emission peaks where their intensity levels can be independently or semi-independently tuned.

In some aspects, an intensity coded optical marker includes at least one emission peak having an intensity level that can be tuned by application of light energy for different amounts of time. In certain aspects, application of a light energy for increasing amounts of time results increases the intensity of the emission peak. In other aspects, application of a light energy for increasing amounts of time results decreases the intensity of the emission peak. In certain aspects, the intensity of the emission peak is monitored while the light energy is applied to ensure that the desired intensity level is achieved, e.g., using feedback control mechanisms. A feedback control mechanism can be used to detect the intensity of the emission peak detected from the optical marker (or a cell labeled with the optical marker) and control the amount of light energy (e.g., via different amounts of time and/or different power of light) delivered to the optical marker (or cell) in order to achieve the desired intensity for an optical code. Such mechanisms are particularly useful when attempting to achieve accurate desired intensity levels in situations where the desired intensity levels are relatively close to each other. For example, a feedback control mechanism can be used to apply light to an optical marker when the intensity levels for an optical code differ from each other by no more than about 100%, no more than about 50%, no more than about 25%, no more than about 20%, no more than about 15%, no more than about 10%, or no more than about 5%.

In some aspects, a wavelength-intensity encoding scheme provides a plurality of optically detectable codes by varying the emission wavelength and the emission intensity level of the emission peaks of the encoded optical marker via application of different light energies. The wavelength-intensity encoding scheme can be any suitable combination of the wavelength encoding schemes and intensity encoding schemes provided herein.

In some aspects, the present disclosure provides encoded optical markers that are capable of lifetime encoding, e.g., have optically detectable codes defined based on the emission lifetime of the optical marker. In some aspects, the fluorescence lifetime is defined as the average time the marker stays in its excited state before emitting a photon. Fluorescence lifetime can be experimentally determined from the time constant of a single exponential decay function or the average time constant of a multiexponential decay function of the fluorophore. In certain aspects, the encoded optical markers are capable of wavelength-intensity-lifetime encoding, also known as wavelength-intensity-lifetime multiplexing. As the color and intensity coding can be limited by spectral overlap and background interference, the lifetime coding provides an additional coding dimension. Distinguishable lifetime codes can be achieved by using optical markers having different lifetimes when converted to different optical states by light energy. For each single-color emission band, a large number of encoded optical markers can be generated and used as lifetime codes with distinct lifetimes ranging from 10 picoseconds to 1 millisecond.

In some aspects, the encoded optical markers have multiple, e.g., 2-10, sets of emission peaks, and each set of emission peak or peaks have a fluorescence or luminescence lifetime different from others. The lifetime can vary from 10 picoseconds to 1 millisecond. In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond.

In some aspects, an encoded optical marker comprises at least one chromophoric polymer particle that is convertible between different optical states upon application of different light energies, with the different optical states defining different optical codes. Chromophoric polymer particles capable of optical encoding and/or biomolecular encoding are also referred to herein as "encoded chromophoric polymer particles" or "encoded polymer particles."

In various aspects of the present disclosure, the optically detectable code is defined by the chromophores of the encoded chromophoric polymer particle. The encoded chromophoric polymer particle can include any suitable number and combination of the various chromophore compositions provided herein. For instance, exemplary chromophores suitable for use with the present disclosure include but are not limited to chromophoric polymers (e.g., one or more chromophoric polymers forming the polymer matrix of the particle, such as narrow-band chromophoric polymers), lanthanide chromophores (e.g., lanthanide ions, lanthanide complexes, lanthanide nanoparticles, or other lanthanide materials), or chromophoric dyes (e.g., fluorescent dyes, luminescent dyes). In some aspects, the chromophores are photoswitchable, photoactivatable, or photoconvertible chromophores as described herein.

In some aspects, because of the unique feature that chromophoric polymers are used as the polymer matrix, the present disclosure provides chromophoric particles for encoding where the entire particle is composed of chromophores (e.g., fluorescent and/or luminescent materials such as chromophoric polymers, lanthanide chromophores, or chromophoric dyes). In some aspects, up to 90% of the mass of each particle is composed of chromophores. In some aspects, up to 80% of the mass of each particle is composed of chromophores. In some aspects, up to 70% of the mass of each particle is composed of chromophores. In some aspects, up to 60% of the mass of each particle is composed of chromophores. In some aspects, up to 50% of the mass of each particle is composed of chromophores. In some aspects, up to 40% of the mass of each particle is composed of chromophores. In some aspects, up to 30% of the mass of each particle is composed of chromophores. In some aspects, up to 20% of the mass of each particle is composed of chromophores. In some aspects, up to 10% of the mass of each particle is composed of chromophores. In some aspects, the encoded chromophoric polymer particle includes a plurality of distinct chromophores and the combined mass of the plurality of distinct chromophores is between 1% and 99%, 10% and 99%, 20% and 99%, 30% and 99%, 40% and 99%, or 50% and 99% of the total mass of the polymer particle. In certain aspects, the chromophores can be chromophoric polymers alone. In other aspects, the chromophores can include chromophoric polymers physically blended or chemically cross-linked with other chromophore types, e.g., lanthanide materials such as lanthanide ions, lanthanide complexes, lanthanide nanoparticles, chromophoric dyes such as fluorescent dyes, or combinations thereof.

In some aspects, the encoded chromophoric polymer particle includes one or more distinct chromophores (e.g., chromophores having different structures, compositions, and/or properties) that are used to define the optically detectable code. The encoded chromophoric polymer particle can include any suitable number and combination of distinct chromophore types, such as only a single distinct chromophore, two or more distinct chromophores, three or more or more distinct chromophores, four or more distinct chromophores, five or more distinct chromophores, six or more distinct chromophores, seven or more distinct chromophores, eight or more distinct chromophores, nine or more distinct chromophores, ten or more distinct chromophores, twenty or more distinct chromophores, fifty or more distinct chromophores, or one hundred or more distinct chromophores. In some aspects, the encoded chromophoric polymer particle comprises a fixed mass ratio between any of the distinct chromophores in the plurality of distinct chromophores, such as a fixed mass ratio between two or more distinct chromophores, three or more or more distinct chromophores, four or more distinct chromophores, five or more distinct chromophores, six or more distinct chromophores, seven or more distinct chromophores, eight or more distinct chromophores, nine or more distinct chromophores, ten or more distinct chromophores, twenty or more distinct chromophores, fifty or more distinct chromophores, or one hundred or more distinct chromophores.

In certain aspects, distinct chromophores have one or more optical properties (e.g., emission spectra, emission intensities, emission wavelengths, emission lifetimes, emission rates, absorbance wavelengths, etc.) that are distinguishable from one another. For example, an encoded chromophoric polymer particle can include a polymer matrix (e.g., formed from at least one chromophoric polymer) and one or more chromophores (e.g., lanthanide chromophores) having optical properties that are distinguishable from the optical properties of the polymer matrix. In some aspects, an encoded chromophoric polymer particle includes two or more, three or more, four or more, five or more, six or more, seven or more, eight or more, nine or more, or ten or more distinct chromophores having emission spectra that are distinguishable from each other. In some aspects, the encoded chromophoric polymer particle includes two or more, three or more, four or more, five or more, six or more, seven or more, eight or more, nine or more, or ten or more distinct chromophores having emission intensities that are distinguishable from each other. In some aspects, the encoded chromophoric polymer particle includes two or more, three or more, four or more, five or more, six or more, seven or more, eight or more, nine or more, or ten or more distinct chromophores having emission wavelengths that are distinguishable from each other. In some aspects, the encoded chromophoric polymer particle includes two or more, three or more, four or more, five or more, six or more, seven or more, eight or more, nine or more, or ten or more distinct chromophores having emission lifetimes that are distinguishable from each other.

The present disclosure provides methods for multiplexed sorting of cells (e.g., adherent cells) using the encoded optical markers described herein. In some aspects, a multiplexed sorting method involves providing each cell of a plurality of cells (e.g., adherent cells) with one or more of the encoded optical markers described herein. For example, a cell can be provided with at least one, at least two, at least three, at least four, at least five, at least six, at least seven, at least eight, at least nine, at least ten, at least 20, at least 30, at least 40, at least 50, at least 60, at least 70, at least 80, at least 90, at least 100, at least 200, or at least 500 different types of encoded optical markers. In certain aspects, a multiplexed sorting scheme uses a single encoded optical marker that is convertible by application of light energy between a plurality of different optical states (e.g., two different optical states), with different optical states defining a different optically detectable codes. In other aspects, a multiplexed sorting scheme uses a plurality of encoded optical markers that are independently convertible by application of light energy between a plurality of different respective optical states, with the different combinations of optical states across the plurality of markers defining different optically detectable codes. In some aspects, selective application of different types of light energy is applied to convert the optical marker(s) of certain cells in order to mark those cells with a desired optically detectable code. Subsequently, cell sorting is performed based on the optically detectable code exhibited by each cell.

Methods for Providing Cells with Optical Markers

In some aspects of the present disclosure, the optical markers are endogenous markers that are expressed by the cells of interest, such that the target cells include one or more genes encoding the endogenous marker. This approach advantageously obviates the need for a separate cell labeling step. Various techniques can be used to genetically manipulate target cells in vitro or in vivo to express an optical marker, including but not limited to DNA or RNA transfection (e.g., via electroporation, sonoporation, gene gun, non-viral vectors such as polymer or liposomes, etc.) or transduction (e.g., via retroviruses, lentiviruses, adenoviruses, adeno-associated viruses, etc.). In certain aspects, the cells of interest are isolated from a transgenic organism (e.g., plant or animal) that has been genetically manipulated to express the endogenous marker. Methods for the production of such transgenic organisms are known to those of skill in the art.

In some aspects, an optical marker is genetically encoded and expressed in the cell, and undergoes a change in structure and/or composition when exposed to light energy which alters the optical properties of the optical marker. For example, in some aspects, a genetically encoded optical marker includes at least one photoactivatable or one photoswitchable fluorescent protein upon application of light energy. Examples of photoactivatable fluorescent proteins that can be genetically encoded and expressed in cells include but are not limited to PA-GFP, PA-CFP2, PA-mRFP1, PA-mCherry1, or Phamret.

In alternative aspects of the present disclosure, the optical markers are exogenous markers that are coupled to the cells. This approach permits labeling without requiring genetic manipulation of the target cells, which may not be desirable or feasible in certain aspects (e.g., biopsied samples). Various techniques can be used to produce exogenous markers suitable for cell labeling, such as functionalization of the markers for subsequent bioconjugation (e.g., to an entity that binds to the target cells). In some aspects, the present disclosure provides optical markers (e.g., photo switchable chromophores, photoactivatable chromophores, photoconvertible chromophores, photoswitchable chromophoric polymer particles, etc.) functionalized with one or more functional groups. In some aspects, a functional group is a chemical unit that can be attached, such as by any stable physical or chemical association, to the optical marker, thereby rendering the optical marker available for conjugation or bioconjugation. In some aspects, the functional group is a hydrophobic functional group. Examples of hydrophobic functional groups include but are not limited to alkyne, strained alkyne, azide, diene, alkene, cyclooctyne, or phosphine groups (e.g., for click chemistry). In other aspects, the functional group is a hydrophilic functional group. Examples of hydrophilic functional groups include but are not limited to carboxylic acid or salts thereof, amino, mercapto, azido, diazo, aldehyde, ester, hydroxyl, carbonyl, sulfate, sulfonate, phosphate, cyanate, succinimidyl ester groups, or substituted derivatives thereof. In some aspects, optical markers are functionalized using functional groups including, without limitation, any the following: an aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or combination thereof.

In some aspects where the optical marker includes a chromophoric polymer particle, a functional group is created with covalent bonding to the backbone, side chain, or terminating unit of the chromophoric polymer. Therefore, the resulting chromophoric polymer particles have one or more functional groups for bioconjugation. In some aspects, each chromophoric polymer particle has only one functional group. In some aspects, each chromophoric polymer particle has only two functional groups. The two functional groups can be the same or different. In some aspects, each chromophoric polymer particle has three or more functional groups. The three or more functional groups can be the same or different.

In some aspects, the present disclosure describes a bioconjugate of the optical markers provided herein. In certain aspects, a bioconjugate includes an optical marker associated with one or more biomolecules, e.g., a synthetic or naturally occurring protein, glycoprotein, peptide, amino acid, metabolite, drug, toxin, nucleic acid, nucleotide, carbohydrate, sugar, lipid, fatty acid, polypeptide, polynucleotide, antibody, avidin, biotin, or combinations thereof. In other aspects, the bioconjugate includes an optical marker associated with one or more biological particles such as viruses, bacteria, cells, biological or synthetic vesicles such as liposomes, or combinations thereof. In some aspects, biomolecular conjugation of a biomolecule or biological particle to the optical marker does not substantially change the optical properties (e.g., emissive properties) of the optical marker. For example, in some aspects, bioconjugation does not substantially change the emission spectra, quantum yield, photostability, optical states, etc. of the optical marker.

In some aspects, the bioconjugate is formed by the attachment of a biomolecule (or biological particle) to one or more functional groups of the optical marker. The attachment can be direct or indirect. Optionally, the biomolecule is attached to the functional group of the optical marker via a covalent bond. For example, if the functional group of the optical marker is a carboxyl group, a protein biomolecule can be directly attached to the optical marker by cross-linking the carboxyl group with an amine group of the protein molecule. In other aspects, the functional group of the optical marker is an avidin (e.g., streptavidin) that binds to a biotin-functionalized biomolecule (e.g., a biotinylated antibody). In various aspects of the present disclosure, cross-linking agents are utilized to facilitate bioconjugation of optical markers. In some aspects, a cross-linking agent is a compound or moiety that is capable of forming a chemical bond between molecular groups on similar or dissimilar molecules so as to covalently bond together the molecules.

In some aspects, labeling of a target cell population (e.g., adherent cells) is achieved using optical markers conjugated to biomolecules that specifically bind one or more intracellular and/or extracellular binding targets on the target cells. In certain aspects, the binding target is a polypeptide, such as a protein, and the biomolecule is a primary antibody that specifically binds to the target polypeptide.

In some aspects, labeling of a target cell population (e.g., adherent cells) is achieved using optical markers (e.g. chromophoric polymer particles) that are specifically endocytosed (e.g. via specific binding to a cell surface molecule) by the cell. In certain aspects, labeling of a target cell population (e.g., adherent cells) is achieved using optical markers (e.g. chromophoric polymer particles) that are non-specifically endocytosed (e.g. via non-specific binding to a cell) by the cell. In certain aspects, labeling of a target cell population (e.g., adherent cells) is achieved using optical markers conjugated with a cell penetrating or cell targeting molecule (e.g. a cell penetrating peptide).

Systems for Optically Marking and Sorting Cells

In some aspects of the present disclosure, a system for optically marking and sorting cells is provided. In certain aspects, the system includes a plurality of adherent cells attached to a substrate, a source of electromagnetic radiation (e.g., a light source), one or more processors operably coupled to the source, and a cell sorting device. (e.g., a FACS device). Each of the plurality of adherent cells includes at least one optical marker that is convertible from a first optical state to a second optical state, as discussed herein. Optionally, the optical markers of the plurality of cells are all initially in the first optical state. In various aspects, the one or more processors are configured to cause the source to selectively apply energy (e.g., light energy) to a subset of the plurality of adherent cells while attached to the substrate, thereby selectively converting the optical markers of the subset from the first optical state to the second optical state. In various aspects, the cell sorting device is configured to sort the plurality of adherent cells when detached from the substrate based on the optical state of the optical marker, e.g., to separate cells of the subset from cells not of the subset. For example, in some aspects, the cell sorting is performed based on the emission intensity of the optical marker of each cell at a peak emission wavelength.

In some aspects, the source of electromagnetic radiation includes a laser, a lamp (e.g., a mercury lamp, halogen lamp, metal halide lamp, or other suitable lamp), an LED, or a combination thereof. In some aspects, the peak wavelength emitted by the light source of is between about 200 nm and about 300 nm, about 250 nm and about 350 nm, about 300 nm and about 400 nm, about 350 nm and about 450 nm, about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some aspects, two or more light sources having distinct peak wavelengths can be used. In some aspects, light emitted by the light source is spectrally filtered by a light filtering apparatus. In some aspects, the light filtering apparatus includes a filter, e.g., a bandpass filter that only allows light wavelengths falling within a certain range to pass through it towards the cells. In some aspects, the light filtering apparatus includes a multichroic mirror that can separate light into distinct spectral components, such that it only allows light wavelengths falling within a certain range to be directed towards the cells. In some aspects, the longest wavelength that passes through a light filtering apparatus is less than 300 nm, less than 400 nm, less than 500 nm, less than 600 nm, less than 700 nm, less than 800 nm, less than 900 nm, or less than 1000 nm. In some aspects, the shortest wavelength that passes through a light filtering apparatus is more than 200 nm, more than 300 nm, more than 400 nm, more than 500 nm, more than 600 nm, more than 700 nm, more than 800 nm, or more than 900 nm.

In some aspects of the present disclosure, the system also includes an imaging device, such as a microscope (e.g., a confocal microscope, spinning disk microscope, multi-photon microscope, planar illumination microscope, Bessel beam microscope, differential interference contrast microscope, phase contrast microscope, epifluorescent microscope, or a combination thereof). Optionally, the source of electromagnetic radiation is a component of the imaging device, e.g., provides illumination for imaging. In certain aspects, the imaging device is used to obtain image data of the plurality of cells, e.g., when attached to the substrate. Optionally, the image data is used as a basis for selecting the subset of cells to be optically marked. In some aspects, this process occurs manually, e.g., a user views the image data and input instructions to select and optically mark the subset. In other aspects, this process occurs automatically, e.g., the one or more processors analyze the image data, such as by using computer vision or image analysis algorithms, and select the cells to be marked without requiring user input. In alternative aspects, the selection and marking procedure is semi-automated, e.g., involving some user input and some automatic processing.

In some aspects, a system configured for optical encoding and sorting of adherent cells is provided. In certain aspects, the system includes a plurality of adherent cells attached to a substrate, a source of electromagnetic radiation (e.g., a light source), one or more processors operably coupled to the source, and a cell sorting device (e.g., a FACS device). Each of the plurality of adherent cells includes a first optical marker that is convertible from a first optical state to a second optical state upon application of a first light energy, and a second optical marker that is convertible from a third optical state to a fourth optical state upon application of a second light energy. In various aspects, the second light energy is different from the first light energy (e.g., has a different wavelength). In various aspects, the second light energy has the same wavelength as the first light energy but has a different light intensity. In various aspects, the first optical marker has different optical properties than the second optical marker (e.g., different emission spectra). In some aspects, the one or more processors are configured to cause the source to selectively apply the first light energy to a first subset of the cells and the second light energy to a second subset of the cells. In certain aspects, the first and second subsets are different from each other, so as to produce cells with differing combinations of optical states that, for example, represent different optical encodings. Optionally, the cell sorting device can be used to sort the cells according to the different optical encodings.

In some aspects, a system configured for optical encoding and single-cell dispensing of adherent cells is provided. In certain aspects, the system includes a plurality of adherent cells attached to a substrate, a source of electromagnetic radiation (e.g., a light source), one or more processors operably coupled to the source, and a single-cell dispensing system (e.g. into holders such as microwells or droplets). Each of the plurality of adherent cells includes a first optical marker that is convertible from a first optical state to a second optical state upon application of a first light energy, and a second optical marker that is convertible from a third optical state to a fourth optical state upon application of a second light energy. In various aspects, the second light energy is different from the first light energy (e.g., has a different wavelength). In various aspects, the second light energy has the same wavelength as the first light energy but has a different light intensity. Different light intensity can be achieved via either adjusting the power of the light source or adjusting the duration of illumination with a given power of the light source or a combination of the two. In various aspects, the first optical marker has different optical properties than the second optical marker (e.g., different emission spectra). In some aspects, the one or more processors are configured to cause the source to selectively apply the first light energy to a first subset of the cells and the second light energy to a second subset of the cells. In certain aspects, the first and second subsets are different from each other, so as to produce cells with differing combinations of optical states that, for example, represent different optical encodings. The single-cell dispensing device can be used to dispense individual cells, and the identity or characteristics of each cell is decoded optically (e.g. by fluorescence imaging or flow-based optical interrogation) according to the different optical encodings after dispensing. The single-cell dispensing device can dispense cells into microwells or into droplets. After single-cell dispensing and optical decoding to uncover the original characteristics of the cells, the cells can then be lyzed for single-cell analysis. The original characteristics of the single cell can relate to the spatial location of the cell in the tissue, the temporal characteristics of the cell, the appearance of the cell in tissue, the morphology of the cell in tissue, the phenotypic properties of the cell in tissue, or the physiology of the cell observed in tissue, or a combination of these characteristics. Single-cell analysis can include single-cell imaging, single-cell PCR, single-cell RNA-seq, single-cell genotyping, single-cell sequencing, single-cell genetic analysis, single-cell digital ELISA, single-cell assays, single-cell functional studies, single-cell-omics analysis (e.g. metabolomics, genomics, lipidomics, proteomics), or single-cell culture.

In some aspects, a plurality of populations of cells is marked using the encoding scheme described herein, such that each code corresponds to a single population. Such an encoding scheme can include use of photoactivatable markers, for example, adherent chromophoric polymer dots or genetically encoded fluorescent proteins. Examples of photoactivatable fluorescent proteins that can be genetically encoded and expressed in cells include but are not limited to PA-GFP, PA-CFP2, PA-mRFP1, PA-mCherry1, or Phamret. In some cases, 96 or fewer populations, or 384 or fewer populations may be so marked. The cell populations may then be sorted into appropriate well plates, such as a 96-well plate or a 384-well plate, according to their markings, such that each well contains cells most or all of which have a single marking. In some cases, one or more, or even all of the populations comprise a single-cell population.

In some aspects, a system for optically marking cells includes a feedback control mechanism for controlling one or more parameters of the light energy applied to the subset of cells by the light source. In certain aspects, the feedback control mechanism adjusts the power and/or duration of the light energy applied to the subset of cells in order to achieve a targeted emission intensity level for the optical markers of the subset, e.g., for an intensity-based encoding scheme. In certain aspects, the feedback control mechanism includes a detector that detects one or more characteristics of an optical marker, such as an emission intensity level of the optical marker, and generates a signal indicative thereof. In some aspects, the detector includes a microscope, such as a confocal microscope, spinning disk microscope, multi-photon microscope, planar illumination microscope, Bessel beam microscope, differential interference contrast microscope, phase contrast microscope, epifluorescent microscope, or a combination thereof. In some aspects, the detector includes a camera, such as a charge-coupled device camera, that can integrate the signal into an image on a digital chip. In some aspects, the detector includes a photomultiplier tube. In certain aspects, the system includes one or more processors that receive the signal from the detector, and modify the light energy applied to the optical marker in response so as to achieve a targeted emission intensity level for the optical marker (e.g., an intensity level associated with an optical code). The applied light energy can be modified by varying a power of the light energy, a duration of the light energy, or combinations thereof.

In some aspects, the systems described herein include a computer comprising one or more processors and a memory device with executable instructions stored thereon. In some aspects, the computer is used to perform the methods described herein. In various aspects, a computer can be used to implement any of the systems or methods illustrated and described above. In some aspect, a computer includes a processor that communicates with a number of peripheral subsystems via a bus subsystem. These peripheral subsystems can include a storage subsystem, comprising a memory subsystem and a file storage subsystem, user interface input devices, user interface output devices, and a network interface subsystem.

In some aspects, a bus subsystem provides a mechanism for enabling the various components and subsystems of the computer to communicate with each other as intended. The bus subsystem can include a single bus or multiple busses.

In some aspects, a network interface subsystem provides an interface to other computers and networks. The network interface subsystem can serve as an interface for receiving data from and transmitting data to other systems from a computer. For example, a network interface subsystem can enable a computer to connect to the Internet and facilitate communications using the Internet.

In some aspect, the computer includes user interface input devices such as a keyboard, pointing devices such as a mouse, trackball, touchpad, or graphics tablet, a scanner, a barcode scanner, a touch screen incorporated into the display, audio input devices such as voice recognition systems, microphones, and other types of input devices. In general, use of the term "input device" is intended to include all possible types of devices and mechanisms for inputting information to a computer.

In some aspect, the computer includes user interface output devices such as a display subsystem, a printer, a fax machine, or non-visual displays such as audio output devices, etc. The display subsystem can be a cathode ray tube (CRT), a flat-panel device such as a liquid crystal display (LCD), or a projection device. In general, use of the term "output device" is intended to include all possible types of devices and mechanisms for outputting information from a computer.

In some aspects, the computer includes a storage subsystem that provides a computer-readable storage medium for storing the basic programming and data constructs. In some aspects, the storage subsystem stores software (programs, code modules, instructions) that when executed by a processor provides the functionality of the methods and systems described herein. These software modules or instructions can be executed by one or more processors. A storage subsystem can also provide a repository for storing data used in accordance with the present disclosure. The storage subsystem can include a memory subsystem and a file/disk storage subsystem.

In some aspects, the computer includes a memory subsystem that can include a number of memories including a main random access memory (RAM) for storage of instructions and data during program execution and a read only memory (ROM) in which fixed instructions are stored. A file storage subsystem provides a non-transitory persistent (non-volatile) storage for program and data files, and can include a hard disk drive, a floppy disk drive along with associated removable media, a Compact Disk Read Only Memory (CD-ROM) drive, an optical drive, removable media cartridges, and other like storage media.

The computer can be of various types including a personal computer, a portable computer, a workstation, a network computer, a mainframe, a kiosk, a server or any other data processing system. Due to the ever-changing nature of computers and networks, the description of computer contained herein is intended only as a specific example for purposes of illustrating the aspect of the computer. Many other configurations having more or fewer components than the system described herein are possible.

The specific dimensions of any of the apparatuses, devices, systems, and components thereof, of the present disclosure can be readily varied depending upon the intended application, as will be apparent to those of skill in the art in view of the disclosure herein. Moreover, it is understood that the examples and aspects described herein are for illustrative purposes only and that various modifications or changes in light thereof may be suggested to persons skilled in the art and are included within the spirit and purview of this application and scope of the appended claims. Numerous different combinations of aspects described herein are possible, and such combinations are considered part of the present disclosure.

As used herein A and/or B encompasses one or more of A or B, and combinations thereof such as A and B.

All features discussed in connection with any aspect or aspect herein can be readily adapted for use in other aspects and aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

Unless otherwise specified, the presently described methods and processes can be performed in any order. For example, a method describing steps (a), (b), and (c) can be performed with step (a) first, followed by step (b), and then step (c). Or, the method can be performed in a different order such as, for example, with step (b) first followed by step (c) and then step (a). Furthermore, those steps can be performed simultaneously or separately unless otherwise specified with particularity.

The particulars shown herein are by way of example and for purposes of illustrative discussion of the preferred aspects of the present disclosure only and are presented in the cause of providing what is believed to be the most useful and readily understood description of the principles and conceptual aspects of various aspects of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

While preferred aspects of the present disclosure have been shown and described herein, it is to be understood that the disclosure is not limited to the particular aspects of the disclosure described, as variations of the particular aspects can be made and still fall within the scope of the appended claims. It is also to be understood that the terminology employed is for the purpose of describing particular aspects of the disclosure, and is not intended to be limiting. Instead, the scope of the present disclosure is established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the disclosure provided herein.

All features discussed in connection with an aspect or aspect herein can be readily adapted for use in other aspects and aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

EXAMPLES

The following examples are included to further describe some aspects of the present disclosure, and should not be used to limit the scope of the invention.

Example 1

Synthesis of photoswitchable chromophoric polymer particles

This example describes the synthesis of chromophoric polymer particles (also referred to herein as "Pdots") with photoswitching capabilities. The Pdots included a chromophoric polymer and a photochromic quencher. The photochromic quencher acts as an energy acceptor and quenches the polymer's fluorescence via Förster resonance energy transfer (FRET). The photo-induced conversion of the photochromic quencher controls the absence or presence of FRET, resulting in the ON-OFF switching of the polymer fluorescence All of the chemicals and solvents were purchased from Sigma-Aldrich (St. Louis, Mo.) unless indicated otherwise. The fluorescent semiconducting polymer poly[2-methoxy-5-2-ethylhexyloxy]-1,4-(1-cyanovinylene-1,4-phenylene)] (CN-PPV, MW 15,000, polydispersity 5.9) was purchased from ADS Dyes, Inc. (Quebec, Canada). The photochromic quencher 1,2-bis(2,4-dimethyl-5-phenyl-3-thienyl)-3,3,4,4,5,5,-hexafluoro-1-cyclopentene (BTE) was purchased from TCI (Portland, Oreg.). A comb-like polymer-polystyrene grafted with ethylene oxide functionalized with carboxyl groups (PS-PEG-COOH, main chain MW 8500, graft chain MW 1200, total chain MW 21700, polydispersity 1.25)— was purchased from Polymer Source Inc. (Quebec, Canada). HEPES, EDC (1-ethyl-3[3-dimethylaminopropyl]carbodiimide hydrochloride), and streptavidin were purchased from Invitrogen (Eugene, Oreg.). All chemicals were used as received without further purification. High purity of MilliQ water (18.2 Ma cm) was used throughout the experiment.

The photoswitchable Pdots were prepared by using a modified nanoprecipitation method. Typically, CN-PPV, BTE, and PS-PEG-COOH were separately dissolved in THF (anhydrous, ≥99.9%, inhibitor-free) to make three 1-mg/mL stock solutions. PS-PEG-COOH was blended with Pdots to functionalize the carboxyl groups for bioconjugation. Suitable amounts of CN-PPV, BTE, and PS-PEG-COOH stock solution were taken to get the desired concentrations and doping ratios. Typically, 0.1 mL CN-PPV (1 mg/mL), 0.3 mL BTE (1 mg/mL), and 0.02 mL PS-PEG-COOH (1 mg/mL) were mixed. The mixture was sonicated to form a homogeneous solution and then quickly injected to 10-mL Milli-Q pure water in a bath sonicator for 30 sec. Then the THF was removed by nitrogen stripping and heating at 90° C. Finally, the residue solution was passed through a 0.2-μm filter from VWR (Radnor, Pa.) to remove the aggregation particles and precipitations, such as the undoped BTE. The synthesized CN-PPV-BTE Pdots were well dispersed in water and stable for months without aggregation.

UV/vis absorption spectra of the Pdots solution were recorded with a DU 720 scanning spectrophotometer from Beckman Coulter, Inc. (Brea, Calif.). Fluorescence spectra were acquired in a commercial Fluorolog-3 fluorometer from HORIBA Jobin Yvon Inc. (Edison, N.J.). The particle sizes of Pdots in bulk solution were measured by the dynamic light scattering (NanoS Zetasizer) from Malvern (Westborough, Mass.). For the electron micrograph measurements, 2-3 drops of the Pdots solution (-20 ppm) were placed on a carbon-coated copper grid (200 mesh) provided from TED PELLA, Inc. (Redding, Calif.) and then dried under ambient conditions. The dried Pdots' sizes were measured with a transmission electron microscope (Tecnai F20) from FEI (Hillsboro, Oreg.).

Bioconjugation was carried out by coupling carboxylate-functionalized Pdots and the amine-containing streptavidin purchased from Invitrogen (Eugene, Oreg.) via EDC-catalyzed coupling. Typically, for a 4-mL Pdot solution with the concentration of 50 ppm, 80-μL polyethylene glycol (5% w/v PEG, MW 3350) and 80-μL HEPES buffer (1 M, pH 7.3) were mixed. Then 240-μL streptavidin (1 mg/mL in 20 mM HEPES buffer) was added to the Pdots solution and mixed on a vortex. Finally, 80 μL of freshly prepared EDC (10 mg/mL in MilliQ water) was added to the Pdots solution. The mixture was stirred for 4 hr at room temperature. After bioconjugation, 80-μL BSA (10 wt %) was added to the Pdots solution, and the reaction was continued for another 20 min to eliminate the aggregation of Pdots. An 80-μL aliquot of Triton X-100 (2.5 wt % in MilliQ water) was added to the Pdots solution to make the Pdots more stable. The mixture then was transferred to a centrifuge ultrafiltration tube (Amicon® Ultra-4, MWCO: 100 kDa, from EMD Millipore, Billerica, Mass.) and then concentrated to 0.5 mL by centrifugation. Finally, the mixture was purified by gel filtration via Sephacryl HR-300 gel media to obtain streptavidin-functionalized Pdots for cellular labeling. Aliquots of 50-μL BSA (10 wt %) and 5-μL sodium azide were added to the purified Pdots solution for long-term storage.

FIGS. 2A through 2C show a schematic illustration of the FRET mechanism between CN-PPV Pdots and the BTE. CN-PPV Pdots emit orange fluorescence with peak at 590 nm, which overlaps well with the absorption of the quencher-form of the photochromic molecule BTE (1,2-bis(2,4-dimethyl-5-phenyl-3-thienyl)-3,3,4,4,5,5,-hexafluoro-1-cyclopentene). BTE, a diarylethene, has good photoswitching kinetics, exceptional thermal stability, and suitable fatigue resistance. BTE has no quenching effect on Pdots in its initial open-ring state. However, after UV-induced photocyclization, the open-ring BTE transforms to the closed-ring isomer. The closed-ring isomer exhibits strong absorption bands in the visible range and can efficiently quench the fluorescence emitted from most fluorophores. The closed-ring isomer is readily converted back to the open-ring form with red-light illumination, which turns on the fluorescence of the CN-PPV Pdot because its fluorescence is no longer quenched by the closed-ring form of BTE.

As depicted in FIGS. 2A through 2C, the fluorescence emitted from CN-PPV Pdots was not affected by the open-ring BTE (ON state). The Pdots' fluorescence was quenched by the closed-ring BTE (OFF state), which formed upon UV irradiation. When the BTE-doped CN-PPV Pdots (CN-PPV-BTE Pdots) were irradiated by red light, the closed-ring BTE returned to its open-ring state, thereby turning on again the fluorescence from CN-PPV Pdots.

Figure 3A:
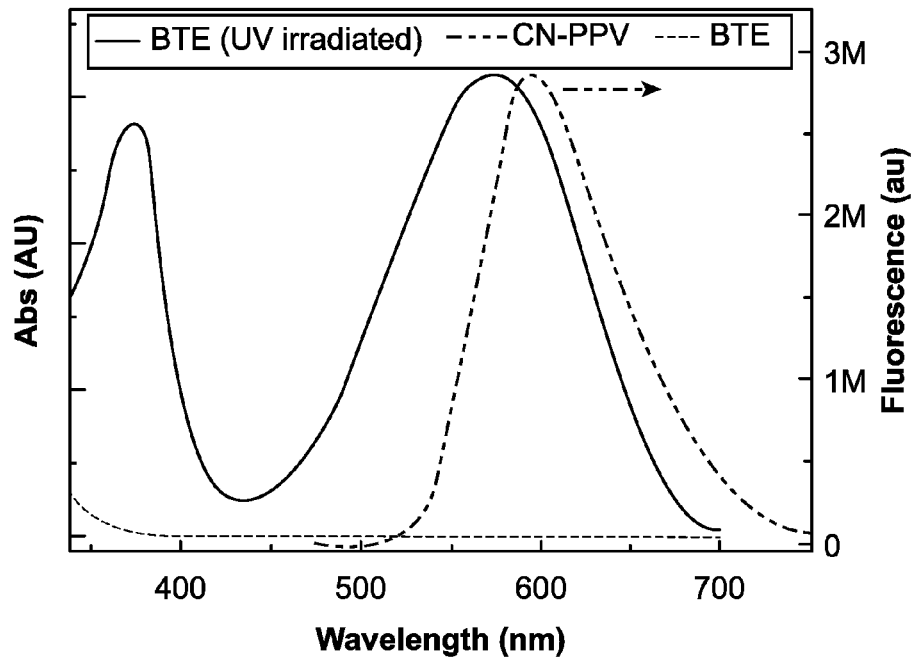
FIG. 3A illustrates the UV-vis spectra of BTE with open-ring (dark solid line) and closed-ring (UV-irradiated, light solid line) states in THF and the fluorescence spectrum of CN-PPV Pdots in $H_2O$ (dashed line, Ex. 450 nm).

FIG. 3A shows the optical properties of BTE before and after UV irradiation. The open-ring BTE dissolved in tetrahydrofuran (THF) was transparent and had no absorption band in the visible wavelength region. After irradiation with UV light, the solution turned into a dark-blue color and had two absorption bands centered at 375 nm and 580 nm. The absorption spectrum of the UV-irradiated BTE (closed-ring) overlapped substantially with the emission spectrum of the CN-PPV Pdot centered at 590 nm (FIG. 3A), ensuring an efficient energy transfer from CN-PPV to the closed-ring BTE. Thus, the fluorescence emitted from CN-PPV can be quenched very efficiently by the closed-ring BTE via FRET.

Figure 3B:
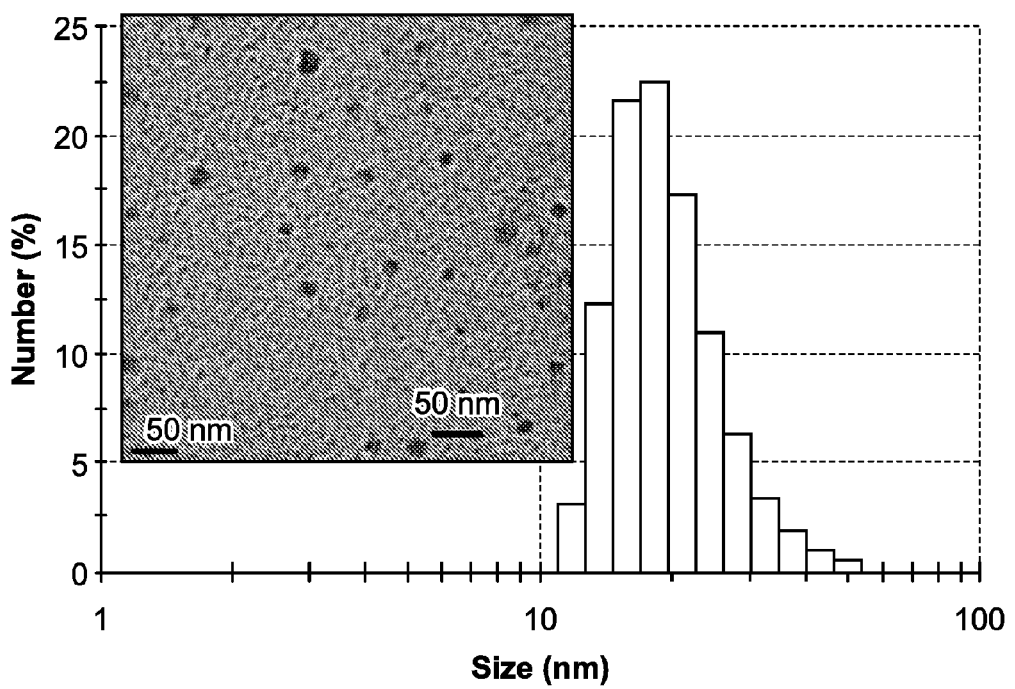
FIG. 3B illustrates the size distribution of CN-PPV-BTE Pdots measured by the dynamic light scattering. The inset shows the transmission electron micrograph of Pdots.

FIG. 3B illustrates sizes of CN-PPV-BTE Pdots. The CN-PPV-BTE Pdots were prepared using a modified nanoprecipitation method. BTE, CN-PPV, and an amphiphilic polystyrene (PS-PEG-COOH) were mixed and dissolved in THF and then injected into water under sonication. PS-PEG-COOH was used to functionalize Pdots with carboxyl groups for facile bioconjugation with streptavidin, which allows for specific cellular targeting via biotinylated primary antibodies. The size of the prepared Pdots was approximately 20 nm in diameter as measured by the dynamic light scattering and transmission electron microscopy.

FIGS. 4A through 4D illustrate the detailed performances of photoswitching of CN-PPV-BTE Pdots. The optical characteristics and photoswitching performances of the CN-PPV-BTE Pdots were examined in bulk solution. Two absorption peaks at 270 nm and 450 nm from the CN-PPV-BTE Pdots (FIG. 4B) were attributed to BTE and CN-PPV (FIG. 4A), respectively. The optimized ratio by weight of BTE:CN-PPV:PS-PEG-COOH was 3:1:0.2. The corresponding doping ratio of BTE to CN-PPV monomer in Pdots was estimated to be 3:4 based on the molar extinction coefficients.

Figure 4A:
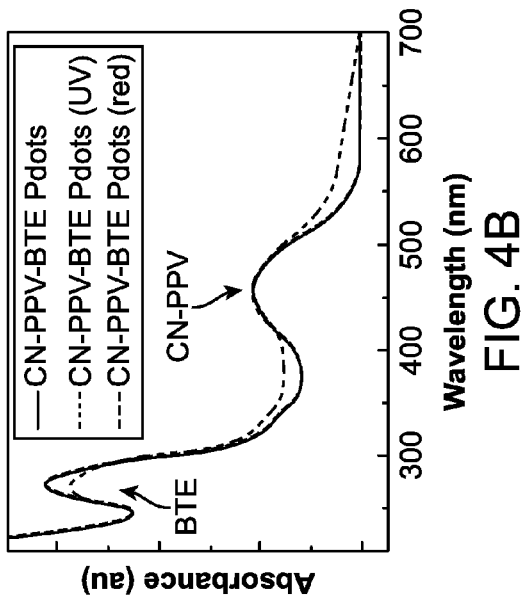
FIG. 4A illustrates the UV/vis absorption spectra of CN-PPV and BTE both at 10 ppm dissolved in either THF or $H_2O$. "BTE in THF (UV)" is the absorption spectrum of BTE after it had been exposed to UV illumination.
Figure 4B:
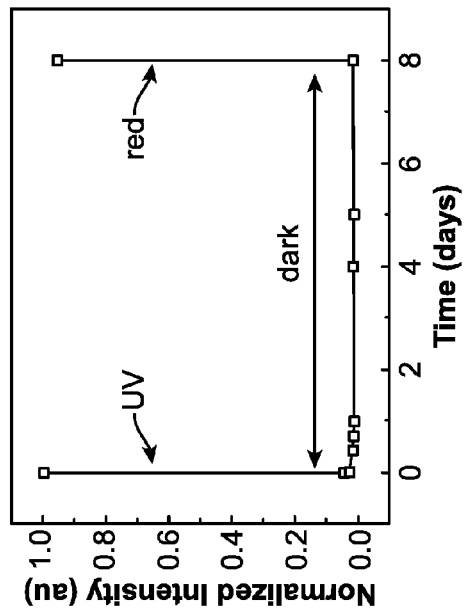
FIG. 4B illustrates the UV/vis absorption spectra of CN-PPV-BTE Pdots before and after photoswitching. CN-PPV-BTE denotes before any light irradiation. CN-PPV-BTE (UV) denotes after illumination with UV light. CNN-PPV-BTE (red) denotes after subsequent illumination with UV and red lights.

When the Pdots solution was irradiated with 254-nm light, the absorbance at 270 nm decreased and two small shoulders at around 375 nm and 580 nm simultaneously appeared (FIG. 4B). This change indicated the conversion of doped BTE from the open-ring to the closed-ring form. After irradiation of the bulk sample with red light (625 nm), the two shoulders (375 nm and 580 nm) diminished, and the absorbance at 270 nm was recovered. This indicated the regeneration of the open-ring BTE.

Figure 3C:
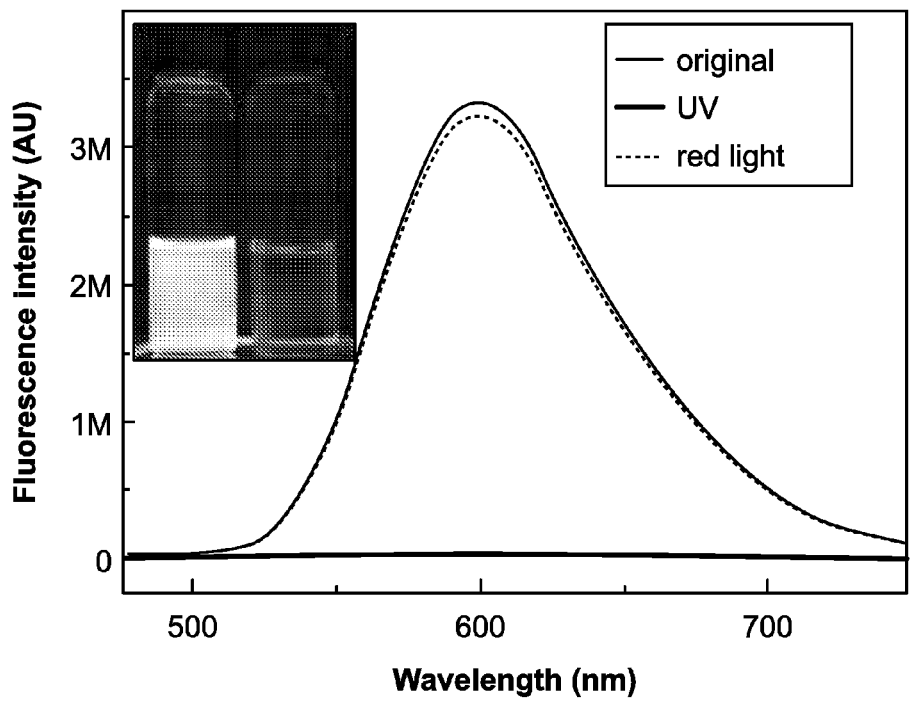
FIG. 3C illustrates the emission spectra (excitation at 450 nm) of the CN-PPV-BTE Pdots solution (thin line, ON state), subsequently obtained after UV (thick line, OFF state) and red light treatments (dashed line, ON state). The inset shows the photograph of Pdots solution at ON and OFF states.

FIG. 3C shows the reversible photoswitching of CN-PPV-BTE Pdots in a single cycle of illumination with UV and red lights. The fluorescence of Pdots significantly decreased (OFF state) upon irradiation with UV light and recovered (ON state) after illumination with red light. The fluorescence intensity ratio of Pdots at 590 nm between the ON state and the OFF state, i.e. ON/OFF ratio, was 150. Compared to alternative photoswitchable Pdots composed by poly[(9,9-dioctylfluorenyl-2,7-diyl)-co-(1,4-benzo-{2,1',3}-thiadiazole)] (PFBT) and spiropyran molecules, the ON/OFF contrast ratio was improved 20 times. The fluorescence quantum yield of Pdots in the ON state was measured to be ~51% and decreased to ~0.4% in the OFF state.

Figure 4C:
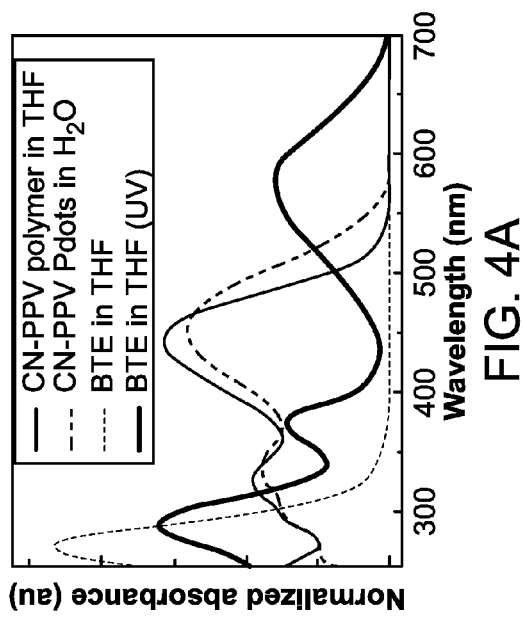
FIG. 4C illustrates photo switching kinetics of CN-PPV and CN-PPV-BTE Pdots in a bulk sample as reported by monitoring the fluorescence at 590 nm (excitation at 450 nm).

After repeated cycles of photoswitching, a slight decay of fluorescence from Pdots was observed, which may be caused by photobleaching. To investigate this, CN-PPV Pdots without doped BTE and CN-PPV-BTE Pdots were examined under the same UV illumination conditions (FIG. 4C). Under these conditions, the fluorescence of the CN-PPV Pdots decreased to 95% of its original value after ~20 sec of exposure to UV light. In contrast, the fluorescence of CN-PPV-BTE Pdots dramatically decayed to ~1% within 20 sec of UV irradiation because of FRET. The fluorescence of CN-PPV-BTE Pdots was recovered with red-light irradiation. From these results, it was confirmed that the dramatic decay of CN-PPV-BTE Pdots' fluorescence after UV irradiation was dominated by FRET and was not caused by photobleaching.

Figure 5:
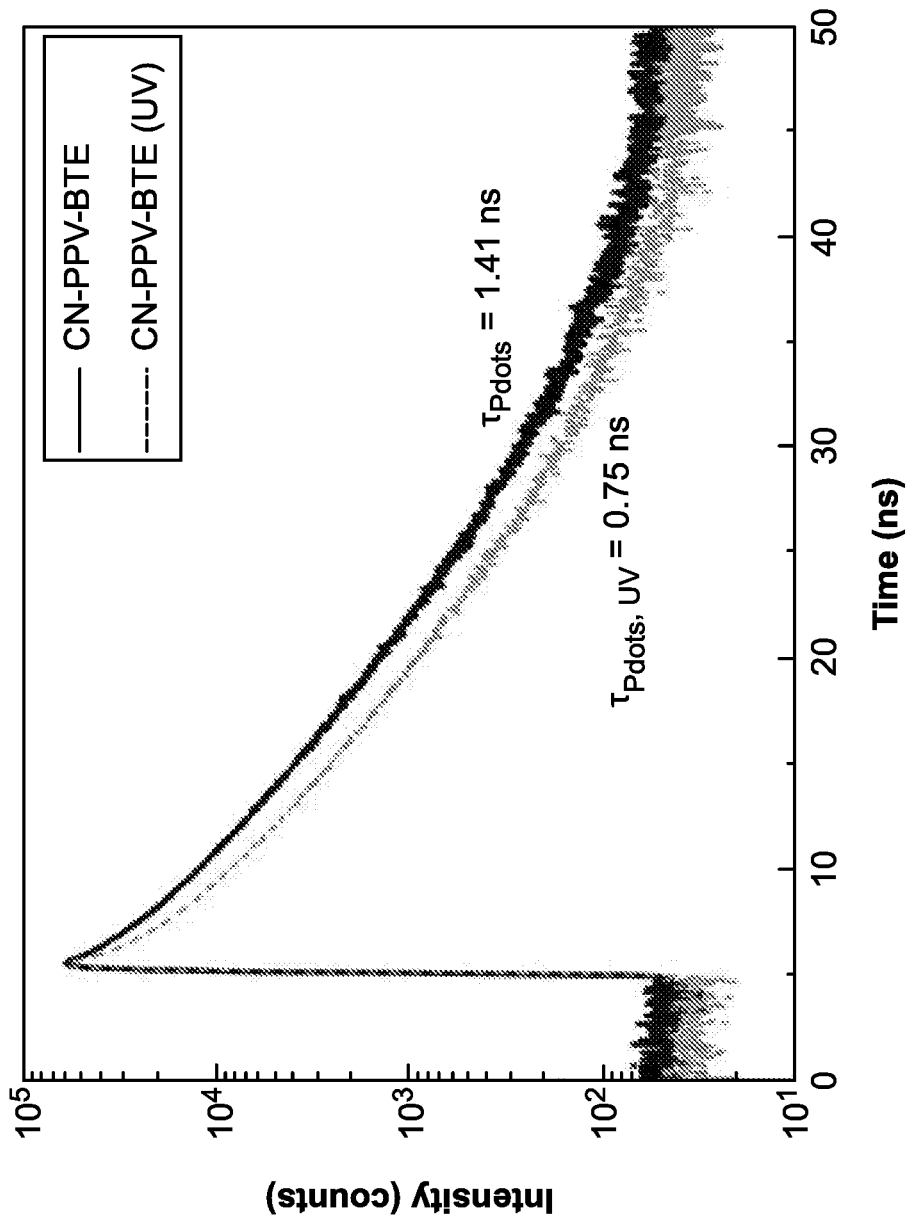
FIG. 5 illustrates the fluorescence lifetime of CN-PPV-BTE Pdots.

FIG. 5 illustrates the time-resolved fluorescence decay of CN-PPV-BTE Pdots before and after irradiation with UV light. The lifetime $\tau$ was obtained by fitting the decay curve with the equation of $I=I_0\exp(-\tau/t)$. I and $I_0$ are the fluorescence intensity at the time "t" and at the initial condition, respectively. The signal was collected above 490 nm upon excitation at 470 nm. The decrease of fluorescence lifetime of CN-PPV-BTE from 1.14 ns to 0.75 ns after irradiation with UV light (FIG. 5) also verified the presence of FRET. Twenty seconds appear sufficient to fully convert the open-ring to the closed-ring form of BTE, and 20 sec was chosen as the period of UV irradiation in all experiments to minimize any potential for photobleaching. Red-light illumination did not cause any photobleaching of the Pdots (FIG. 4C) so the duration of red light irradiation could be extended to several minutes until the fluorescence signal stopped to increase with time (i.e. completely recovered).

Figure 3D:
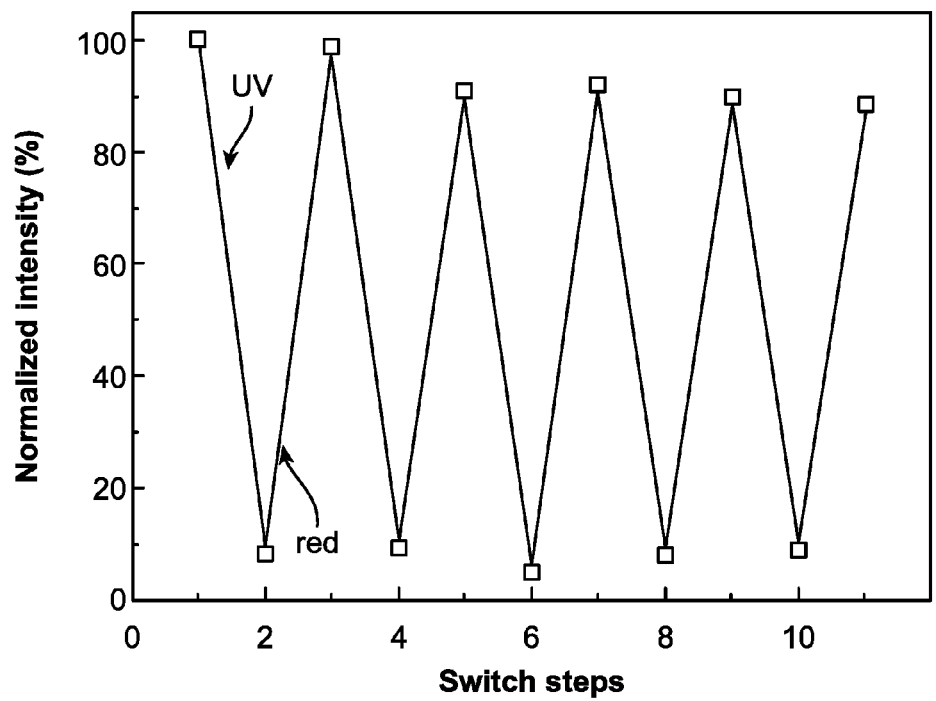
FIG. 3D illustrates the cyclic photoconversion of CN-PPV-BTE Pdots. "UV" and "red" indicate the exposure of samples under UV and red light.

FIG. 3D illustrates the reversibility and reproducibility of photoswitching of CN-PPV-BTE Pdots assessed using repeated cycles of UV and red-light irradiations. The UV and red light irradiations were achieved with a common hand-held UV lamp (254 nm, 310 µW cm$^{-2}$) and a red LED lamp (625 nm, 1.5 mW cm$^{-2}$) for 20 sec and 3 min, respectively. The intensity of fluorescence was recorded at 590 nm. The Pdots were switched reversibly between OFF and ON states for five cycles, which exhibited excellent fatigue resistance and indicated that the BTE molecules in the Pdots were stable throughout the photo switching cycles. After repeated cycles of photo switching, a slight decay of fluorescence from the Pdots was observed, which was caused by photobleaching.

Figure 4D:
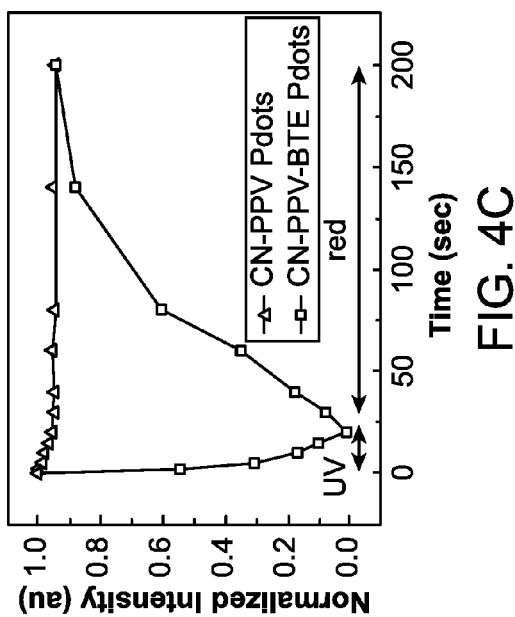
FIG. 4D illustrates thermal stability of CN-PPV-BTE Pdots. Normalized intensity was based on monitoring the fluorescence at 590 nm (excitation at 450 nm).

FIG. 4D shows the excellent thermal and colloidal stability of the photoswitchable Pdots. The OFF state persisted at room temperature for more than one week before the Pdots were returned to the ON state with red-light irradiation.

Figure 6:
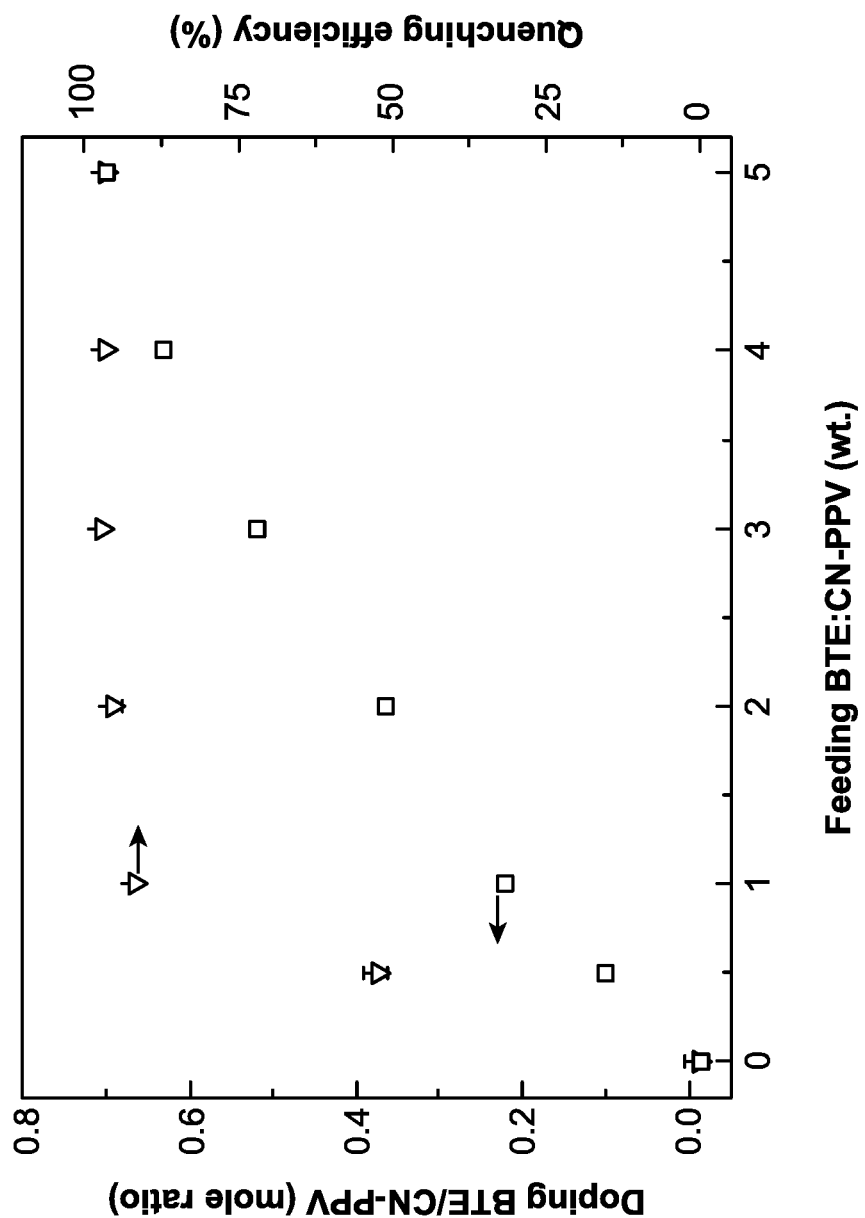
FIG. 6 illustrates the doped ratio (molar) and fluorescence quenching efficiency of CN-PPV-BTE Pdots as a function of feeding ratio (by weight) of BTE to CN-PPV.

FIG. 6 illustrates the doped ratio (molar) (squares) and fluorescence quenching efficiency (triangles) of CN-PPV-BTE Pdots as a function of feeding ratio (by weight) of BTE to CN-PPV. To investigate the dependence of the photoswitching efficiency on the amount of BTE, the fluorescence quenching efficiency (defined as 1-(OFF/ON ratio)) and the doping ratio (molar ratio of BTE to CN-PPV monomer, determined from the molar extinction coefficients) was recorded as a function of the feeding ratio of BTE to CN-PPV (by weight). The OFF state was achieved by illumination of the CN-PPV-BTE Pdots with a common hand-held UV lamp (254 nm, 310 µW cm$^{-2}$) for 20 sec. There was a positive correlation between the feeding ratio and the quenching efficiency as well as the doping ratio (FIG. 6). The doped ratio increased with the feeding ratio until 0.75 (BTE/CN-PPV, by mole). The quenching efficiency, increased with the increasing feeding ratio and achieved the maximum at a feeding ratio of 3 (BTE/CN-PPV, by weight). However, when the feeding ratio was over 3:1 (BTE: CN-PPV), the quenching efficiency started to slightly decrease even when the doping ratio continued to increase slightly. The decrease in the quenching efficiency may be caused by the aggregation of BTE that began to occur within the Pdot. To optimize the doped ratio and the quenching efficiency, the feeding ratio of 3 was used for all experiments.

Figure 7:
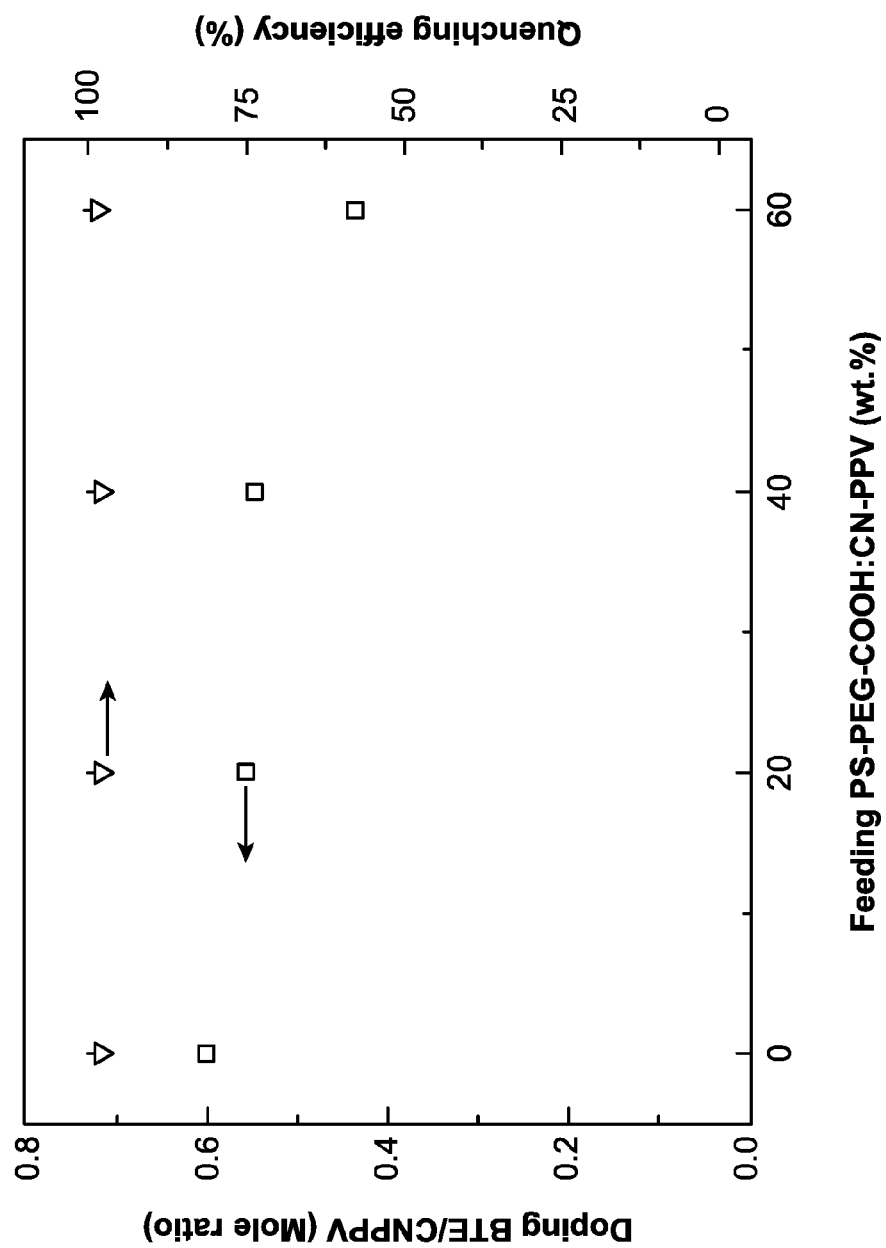
FIG. 7 illustrates the doped ratio (molar) and fluorescence quenching efficiency of CN-PPV-BTE Pdots as a function of feeding ratio (by percent weight) of PS-PEG-COOH to CN-PPV.

FIG. 7 illustrates the doped ratio (molar) (squares) and fluorescence quenching efficiency (triangles) of CN-PPV-BTE Pdots as a function of feeding ratio (by percent weight) of PS-PEG-COOH to CN-PPV. The feeding ratio had no effect on the quenching efficiency. The PS-PEG-COOH:CN-PPV feeding ratio of 20% by weight was used for all the bioconjugation experiments. The OFF state was achieved by illumination of the CN-PPV-BTE Pdots with a common hand-held UV lamp (254 nm, 310 μW cm$^{-2}$) for 20 sec. The amounts of PS-PEG-COOH blended in Pdots were shown to have no effect on the photoswitching efficiency (FIG. 7). A blending ratio of 20% (by weight) PS-PEG-COOH to CN-PPV was used.

Example 2

Photoswitching performance of cells labeled with photoswitchable chromophoric polymer particles This example describes characterization of the photo switching performance of cells labeled with CN-PPV-BTE Pdots produced as described in Example 1 above. To turn cells "ON" and make them fluorescent with 633-nm irradiation, the surfaces of MCF-7 cells were labeled with CN-PPV-BTE-streptavidin (CN-PPV-BTE-SA) Pdots using a biotinylated primary antibody against EpCAM. EpCAM is the epithelial cell surface marker used for the isolation of tumor cells that exhibit epithelial characteristics. Flow cytometry was used to quantify the photoswitching performance of Pdot-labeled cells.

The breast cancer cell line MCF-7 cell and cell culture medium were purchased from American Type Culture Collection (Manassas, Va.). The MCF-7 cells were cultured at 37° C. with 5% $CO_2$ in Eagle's minimum essential medium (EMEM) (with L-glutamine) supplemented with 10% fetal bovine serum and 1% penicillin (50 U/mL)-streptomycin (5 μg/mL) solution. The cells were pre-cultured in culture flasks until ~80% confluency was reached. To harvest the cells, the adherent cells were quickly rinsed with media and then incubated in 5-mL trypsin-ethylenediaminetetraacetic (EDTA) solution (0.25 w/v % trypsin, 2.5 g/L EDTA) at 37° C. for 5-10 min to suspend the cells. The detached cells were collected in a tube and then centrifuged at 6000 rpm for 10 min to precipitate them to the bottom of the tube. After removing the upper media, the cells were rinsed and resuspended in 5-mL culture media. The cell concentration was determined under the microscope with a hemocytometer.

For cellular labeling experiments, ~10$^6$ cells were transferred to 100-μL labeling buffer (1×PBS, 2-mM EDTA, 1% BSA) and incubated with 0.6 μL of 0.5 mg/mL primary biotinylated anti-human CD326 (EpCAM) antibody purchased from BioLegend (San Diego, Calif.) on a rotary shaker in the dark and at room temperature for 30 min. This was followed by a washing step using labeling buffer to remove the excess antibody. For the conjugation of cells and Pdots, the antibody-functionalized cells were incubated with ~5.0 nM streptavidin-functionalized Pdots in 0.2-mL Block-Aid buffer purchased from Invitrogen (Eugene, Oreg.) for 30 min on a rotary shaker in the dark and at room temperature, followed by two washing steps with labeling buffer to remove the excess Pdots. The streptavidin-functionalized Pdots solution was sonicated for 3 min to disperse any potential aggregation. Negative controls were obtained by incubating cells with streptavidin-functionalized Pdots in the absence of the primary biotinylated antibody. Cell fixation was performed by immersing the cells in 500-μL fixing buffer (lx PBS, 2-mM EDTA, 1% BSA, 1% paraformaldehyde) for at least 15 min. Finally the fixed cells were extracted by centrifugation and then redispersed in 500-μL labeling buffer.

The flow cytometry measurements were performed on samples with ~10$^6$ fixed cells in 500-μL labeling buffer. The FACS Cantoll (BD Bioscience, San Jose, Calif.) was used. Cells flowing into the detection chamber were irradiated with a 488-nm beam. The side- and forward-scattered light and excited fluorescence were collected by photomultiplier arrays. The fluorescence signal was collected in the PE channel where the fluorescence was filtered by a 556-nm long-pass and a 585/42 nm band-pass filter. Representative populations of cells were chosen by selection of an appropriate gate. Detection of cell fluorescence was continued until 10$^4$ events had been collected in the active gate. Data analysis was carried out by FlowJo Software (Tree Star, Inc., Ashland, Oreg.).

Figure 8A:
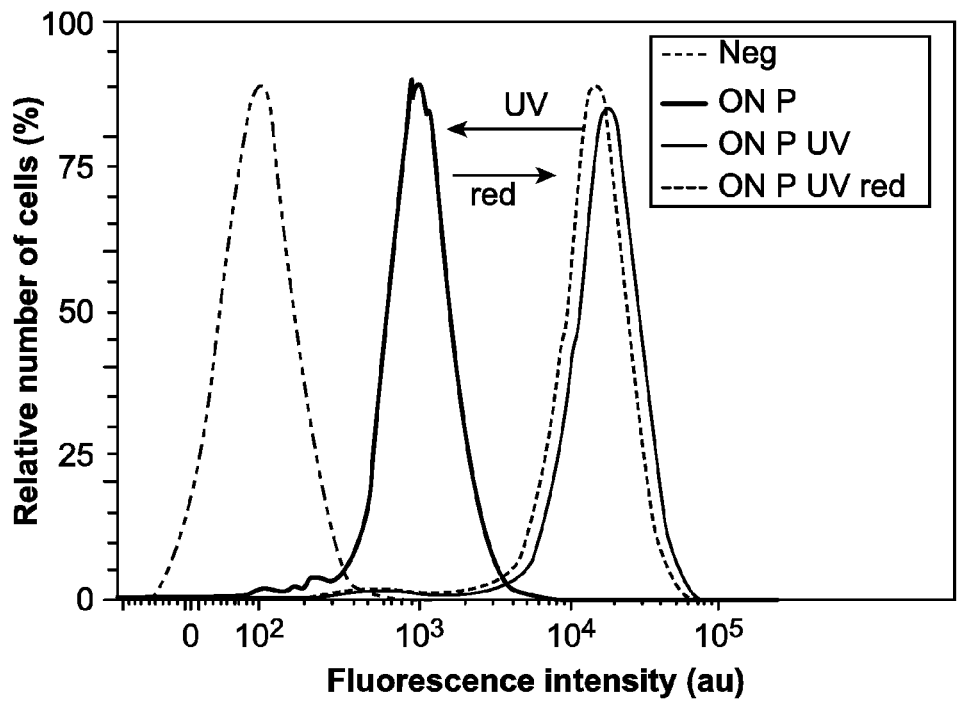
FIGS. 8A and 8B illustrate reversible photoswitching of cells in bulk inside a flow cytometer.
Figure 8B:
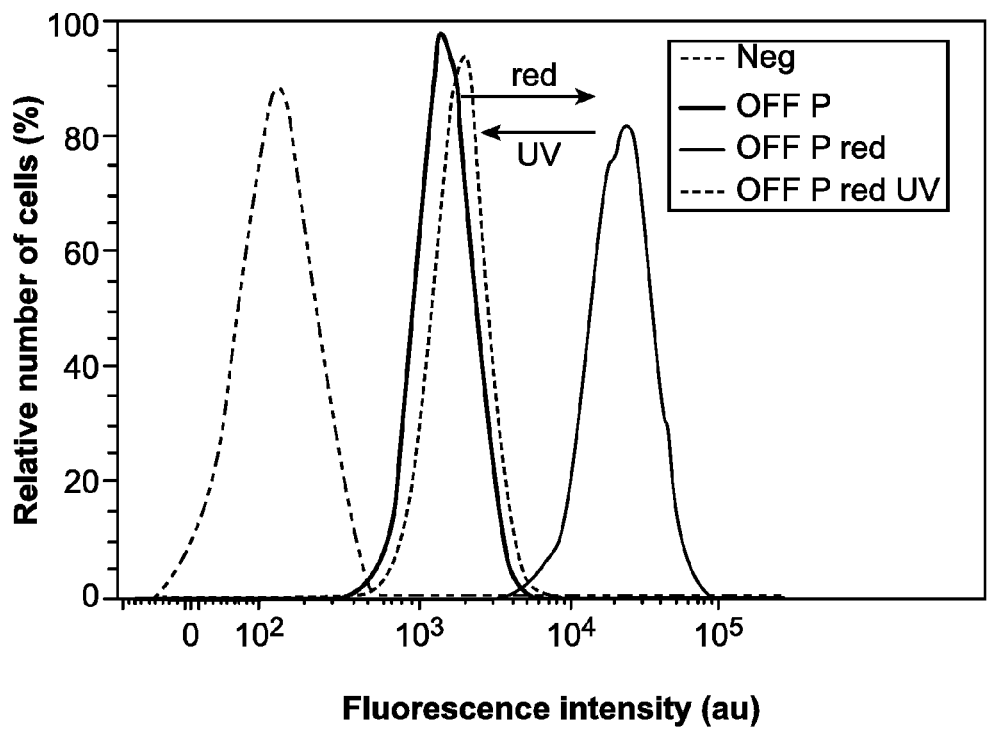

FIGS. 8A and 8B illustrate reversible photoswitching of cells in bulk inside a flow cytometer. The UV treatment was carried out by a handheld UV light (254 nm, 310 μW cm$^{-2}$) for 20 sec; the red-light treatment was done with a red LED (625 nm, 1.5 mW cm$^{-2}$) for 3 min. The fluorescence signal from the flow cytometer was collected in the PE channel (i.e. with 556 nm long-pass and a 585/42 nm band-pass) upon excitation at 488 nm. Whether the MCF-7 cells were initially labeled with CN-PPV-BTE Pdots at "ON" state (FIG. 8A) or "OFF" state (FIG. 8B), the fluorescence intensity distributions of Pdot-labeled cells reversibly changed upon irradiation of UV and red light.

The negative control set of cells (Neg) that were not labeled with Pdots showed the lowest fluorescence intensity. For the negative control (Neg), cells were incubated with CN-PPV-BTE-SA Pdots but without biotinylated primary antibodies. The very low fluorescence of these negative control cells indicated an extremely low nonspecific binding of the Pdots to the cells. The fluorescence intensity distributions of negative control, OFF-state, and ON-state cells were well-resolved from each other. Specifically, the fluorescence peak of the ON-state cells was around 20 times brighter than that of the OFF-state cells inside the flow cytometer, which is more than sufficient for reliable FACS isolation of the ON cells. To prevent potential cell damage by UV irradiation during the photoswitching process, all Pdots were first turned to the OFF state prior to labeling the cells. The Pdot-labeled cells were then turned "ON" via irradiation with the more cell-friendly red light.

Example 3

Optical painting of individual adherent cells labeled with photoswitchable chromophoric polymer particles This example describes optical painting of individual cells labeled with the Pdots described in Examples 1 and 2. To demonstrate the optical painting approach (see FIG. 1), MCF-7 cells grown on a Petri dish were labeled with photoswitchable CN-PPV-BTE-SA Pdots bound to biotinylated anti-EpCAM antibodies. From a practical perspective, cells were labeled with OFF-state Pdots, which were generated by the irradiation of a bulk Pdot sample with UV light prior to cellular labeling. This way, cells were not affected by the UV irradiation needed to turn off Pdots during the painting process. Next, individual cells that were imaged and selected under a microscope were turned on.

Cellular imaging was performed by an in-house fluorescence microscope with a 488-nm laser source under ambient conditions. A 633-nm laser was focused to a spot size of 10 µm in diameter for single-cell painting. A red LED (1000 mA) purchased from Thorlabs (Newton, N.J.) was used for wide-field illumination and cell painting. A plan-Apochromat 63×/1.40 oil DIC objective lens was used for cellular surface imaging.

Figure 9A:
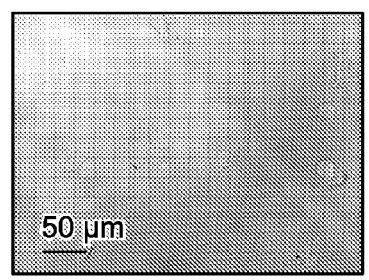
FIGS. 9A through 9E illustrate selective painting of individual MCF-7 cells with a 633-nm laser beam.
Figure 9B:
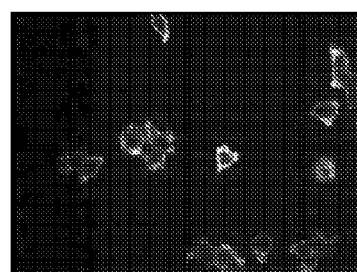
Figure 9C:
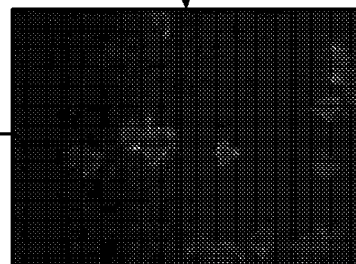

FIGS. 9A through 9E illustrate selective painting of individual MCF-7 cells with a 633-nm laser beam. Cells labeled with ON-state Pdots were used to demonstrate a complete photoswitching cycle. The ON cells appeared orange because of the 590-nm emission from CN-PPV (FIG. 9B). The UV treatment was carried out by a handheld UV lamp (254 nm, 310 µW cm$^{-2}$) for 20 sec. The single-cell painting was achieved by a focused 633-nm laser (about 70 µW or 90 W cm$^{-2}$) for 10 sec; the turning ON of all cells was accomplished by wide-area illumination using a red LED light (625 nm, 1.5 mW cm$^{-2}$) for 3 min. The fluorescence signal was collected above 500 nm upon excitation at 488 nm.

Figure 9D:
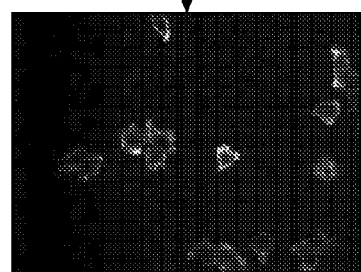
Figure 9E:
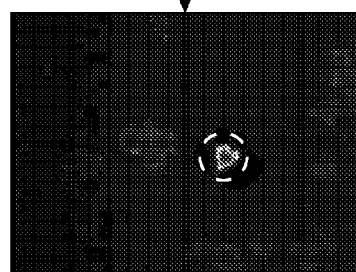

Consistent with the results of flow cytometry discussed above with respect to Example 2 (FIG. 8), the CN-PPV-BTE-SA Pdot-labeled cells became non-fluorescent after illumination with UV light (FIG. 9C); after red LED irradiation, they recovered their orange fluorescence (FIG. 9D). To achieve high-precision and high-throughput single-cell painting under a microscope, a focused 633-nm laser spot of 10 µm in diameter was used to match the dimension of a cell. FIG. 9E shows the exposed cell changed from dark to bright (dashed circle); the other cells that were not illuminated by the focused 633-nm light remained dark.

Figure 10:
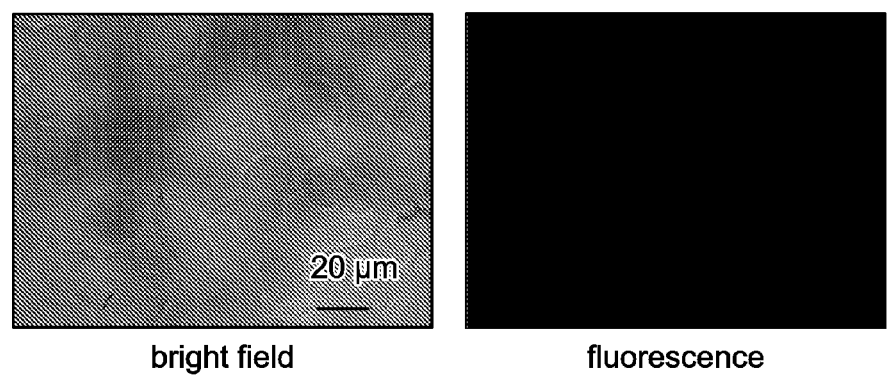
FIG. 10 illustrates bright-field and fluorescence images of negative control set of MCF-7 cells.

FIG. 10 illustrates bright-field and fluorescence images of negative control set of MCF-7 cells. MCF-7 cells were incubated with CN-PPV-BTE-SA Pdots but in the absence of biotinylated primary antibodies. Fluorescence was not observed from these cells, again indicating the absence of nonspecific binding. The fluorescence signal was collected above 500 nm upon excitation at 488 nm.

FIGS. 11A through 11J illustrate painting of multiple cells and a portion of cell by photoswitching. The cell-painting process optically marked two cells (FIGS. 11A through 11E) and a portion of a single cell (FIGS. 11F through 11J) within multiple cells. All cells were in the dark (OFF) state when irradiated with UV light. Next, the selected cells or a portion of one cell underwent photoswitching and turned bright (ON state, indicated by a dashed circle) by the irradiation with a focused 633-nm laser. The UV treatment was carried out by a handheld UV lamp (254 nm, 310 µW cm$^{-2}$) for 20 sec. The red-light irradiation were performed with a focused 633-nm laser spot of a confocal microscope (about 70 µW or 90 W cm$^{-2}$) for 10 sec or by a red LED light (625 nm, 1.5 mW cm$^{-2}$) for 3 min. The fluorescence signal was collected above 500 nm with a long-pass filter upon excitation at 488 nm By tuning the scanning range or the spot size of the focused 633-nm laser beam, the painting of multiple cells and even a portion of a single cell (FIG. 11) was carried out. These results show the versatility of the optical painting method for a range of potential applications.

Example 4

Sorting of optically painted cells

This example describes the sorting of optically painted cells prepared according to the methods illustrated in Examples 1-3 above. A home-built platform called eDAR (ensemble-decision aliquot ranking) was used to collect the painted cells by FACS. eDAR was designed and demonstrated to have high recovery efficiency (95%) for the isolation of rare cells from whole blood. It offers high sensitivity and high throughput: the method can process 1 mL of whole blood containing ~5 billion red and white blood cells within 20 mins. Compared to a commercial FACS instrument, which often requires large amounts of sample cells entering it ($10^6$-$10^7$), eDAR is more flexible in that it can process both large sample volumes (several milliliters of whole blood) with a large number of cells ($10^9$-$10^{11}$) and small sample volumes (few microliters) with limited cell numbers (10-$10^3$).

The sorting process occurred in a microfluidic chip which included a sorting area and a filtration unit. The sorting area contained a sample inlet channel with a section area of 150 µm×50 µm. There were four other channels with 50 µm×200 µm for injecting buffer and passing cells. The filtration unit was constructed with a 5 µm×5 µm slit-filter to capture cells (e.g., MCF-7 with a diameter ~25 µm). The microfluidic chip was fabricated by one-step replica molding into polydimethylsiloxane under a patterned silicon master and then sealed to a glass substrate via plasma oxidation. The Pdot-labeled MCF-7 cells in 1× phosphate buffered saline (PBS) with 10% wt. BSA were injected into the microfluidic chip by a syringe pump. Isoton from Beckman Coulter Inc (Chino, Calif.) was used as the buffer. The fluorescence signal of cells excited by a 488-nm laser beam was collected by fiber-coupled avalanche photodiodes from Excelitas Technologies (Waltham, Mass.) with a filter of 570/20 nm. The sorting process of eDAR was automatically controlled by an in-house LabVIEW (National Instruments, Austin, Tex.) script and a field-programmable-gate-array device built in-house. The sorting threshold was set based on the signal discrepancy between ON-state and OFF-state cells. The hydrodynamic sorting was controlled by a solenoid (INKA1226212H) purchased from the Lee Co. (Westbrook, CT).

FIGS. 12A through 12F illustrate the collection of painted MCF-7 cells by eDAR. FIG. 12A is a schematic of the eDAR microfluidic chip in which the fluorescence of cells was excited by line-confocal laser excitation and the resulting fluorescence signal was detected by an avalanche photodiode detector (APD). When the detected fluorescence of a cell was above a set threshold, the solenoid valve was triggered to open and deflect the main-channel flow from the default waste channel into the cell-collection channel (FIG. 12A, insets). Located in the collection channel and immediately after the sorting junction was a second line-confocal detection region, which confirmed successful cell sorting in real time (FIG. 12B). The sorted cells exhibited fluorescence peaks in both channels. An integrated on-chip filter was located at the end of the cell-collection channel to retain the sorted cell for downstream imaging and analysis (FIGS. 12C and 12D). Non-fluorescent cells that did not trigger sorting just flowed through to the waste channel by default and were not collected. Using the eDAR system, the recovery efficiency of the ON-state cells was investigated and determined to be 92% (FIG. 12E).

Figure 13A:
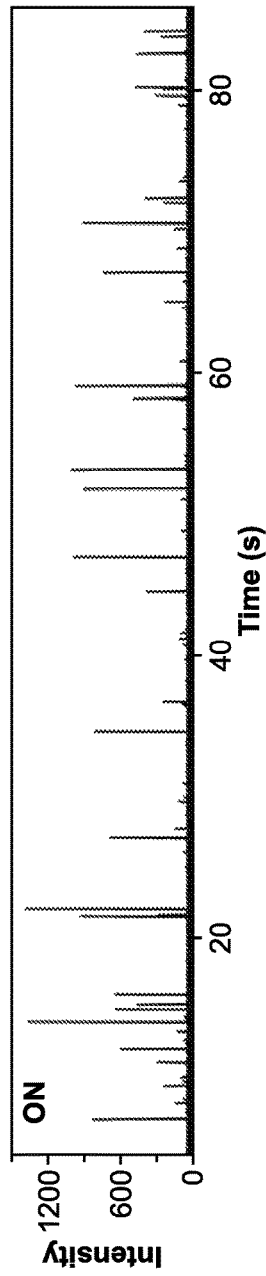
FIGS. 13A through 13C illustrate the fluorescence signal of OFF-state and ON-state cells obtained by eDAR.
Figure 13B:
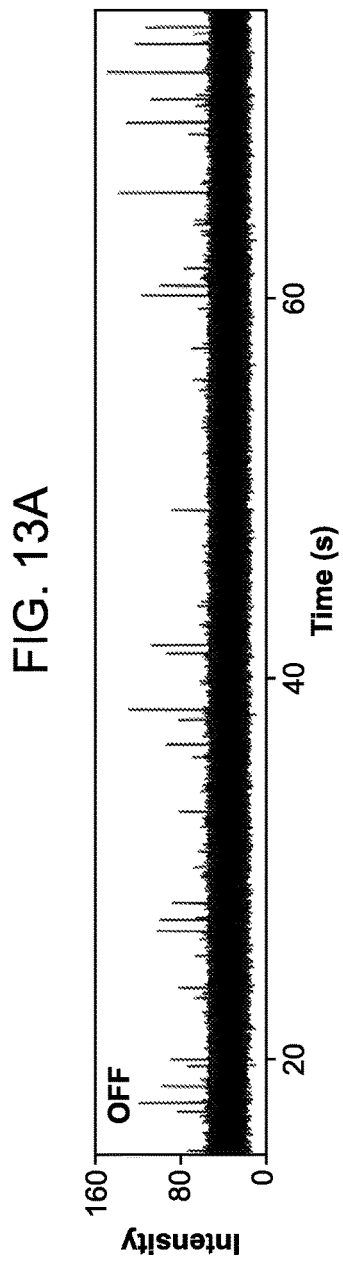

FIGS. 13A and 13B illustrate representative fluorescence intensity time traces obtained from ON-state (FIG. 13A) and OFF-state (FIG. 13B) MCF-7 cells recorded by the avalanche photodiode detector of the eDAR instrument. To ensure eDAR could distinguish the ON-state from the OFF-state cells, these two types of cells were introduced through the eDAR device separately and their respective fluorescence spike intensities analyzed. On average, the signal intensity of ON-state cells was 10 times higher than OFF-state ones.

Figure 13C:
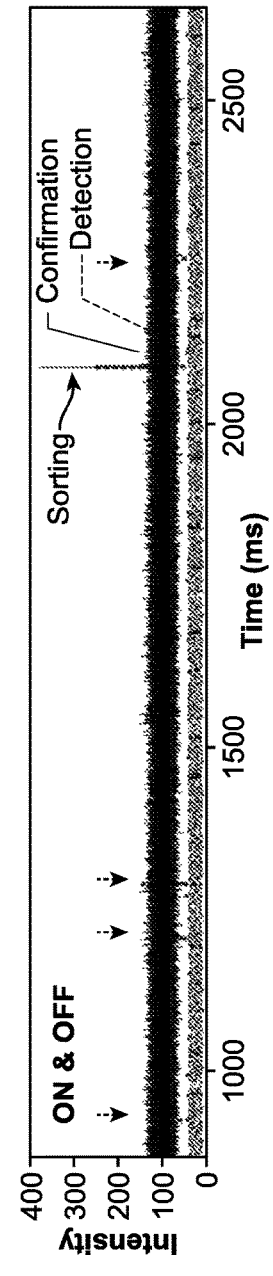

FIG. 13C illustrates the segment of the detection and corresponding confirmation traces obtained from a sample in which ON-state cells were mixed with the OFF-state ones. These two types of cells were mixed together and introduced into the eDAR system to investigate the recovery efficiency of the ON-state cells in a background of OFF-state cells. In the mixed ON-state and OFF-state cell sample, the recovery efficiency was 90% (see FIG. 12F). The peak with the highest signal presented in both traces, indicating a successful sorting of the ON-state cells. Other small peaks (dashed arrows), which were from the OFF-state cells, could not trigger the sorting process so there was no corresponding peak appearing in the confirmation trace. The detection trace was recorded by a detector placed prior to the sorting junction, and the confirmation trace was by another detector placed at the collection channel after the sorting junction. The intensity threshold set for triggering the sorting system was 150 for detection trace.

FIG. 13C shows a representative portion of the recorded fluorescence intensity trace where 5 peaks were detected in the trace. However, 4 of the 5 peaks had a low fluorescence intensity and were below the threshold for sorting; these peaks were from OFF-state cells. Only one peak had a high fluorescence intensity above the sorting threshold; this peak was from an ON-state cell.

Based on the flow cytometry analysis previously described herein with respect to Example 2 (FIG. 8), there may be a small overlap in the fluorescence distribution between ON-state and OFF-state cells, which potentially may result in false positives, that is, the sorting and collection of an OFF-state cell. This false positive would not reduce the recovery efficiency but decrease the purity of the collected ON-state cells. To avoid this potential accidental collection of OFF-state cells, OFF-state cells were labeled with Alexa 647 so they could be identified and distinguished from the ON-state cells after sorting and cell collection.

Figure 14:
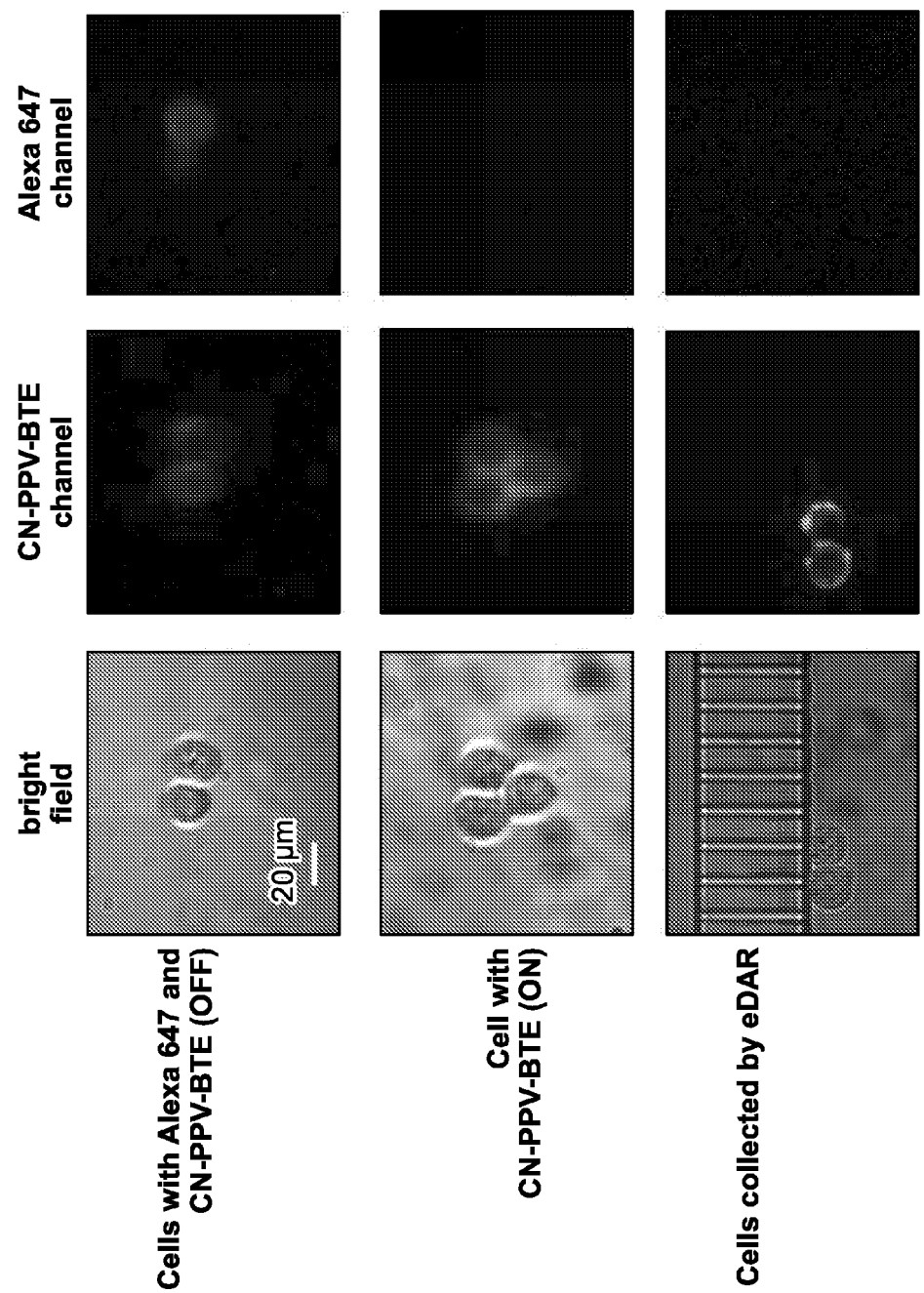
FIG. 14 illustrates a false positive test of eDAR.

FIG. 14 illustrates investigation of potential false positives. To mark OFF-state cells, they were further labeled with a dark-red dye (Alexa 647) so that the cells exhibited the fluorescence of Alexa 647 in addition to CN-PPV-BTE in the OFF state; the ON-state cells only exhibited the fluorescence of CN-PPV-BTE in the ON state without Alexa 647. CN-PPV-BTE and Alexa 647 were excited by green and red lights from a Xe lamp and their fluorescence were separately collected with a 570/20-nm and 675/30-nm bandpass filter, respectively. The cell images of the upper two rows were obtained when cells were extracted in a capillary tube used in cell spiking. After the mixed cells were sorted and collected by eDAR, all collected cells exhibited only the fluorescence of CN-PPV-BTE with no red fluorescence from Alexa 647. This indicates that the collected cells were all in the ON state and there was no accidental sorting of OFF-state cells. No OFF-state cells were found within the population of collected cells, thus indicating a near zero false positive rate and a high purity in the collection of painted cells.

This study demonstrates a new concept for sorting adherent cells. Individual cells of interest are optically "painted" during imaging so that these cells with their fluorescence turned on can be analyzed with flow cytometry or isolated by FACS. This approach is inherently compatible with imaging and offers high throughput because of FACS' fast cell sorting speed. To implement this concept, photoswitchable Pdots were developed that were exceptionally bright; provided high brightness contrast; were reversible with good photoswitching fatigue resistance; had fast photoswitching kinetics; were thermally stable and did not spontaneously revert back to the dark state or vice versa. Additionally, these photoswitchable Pdots were turned on with red light which exerts less cell stress than UV or blue light. Finally, the painted cells were recovered with high efficiency and excellent purity. This method extends the power of FACS to adherent cells and allows single adherent cells to be sorted and isolated based on their morphology and spatial location in a cellular network. This capability will enhance the study of single cells within tissues and should be useful for both basic biological studies and clinical research.

Example 5

Multi-color photoswitching of encoded chromophoric polymer particles

This example describes a multi-color encoding scheme using photoswitchable chromophoric polymer particles ("Pdots"). In this example, coded Pdots having two emission peaks at 520 nm and 680 nm are used, where these two emission peaks can be individually turned ON and OFF, thus resulting in four photoswitchable codes.

Figure 16A:
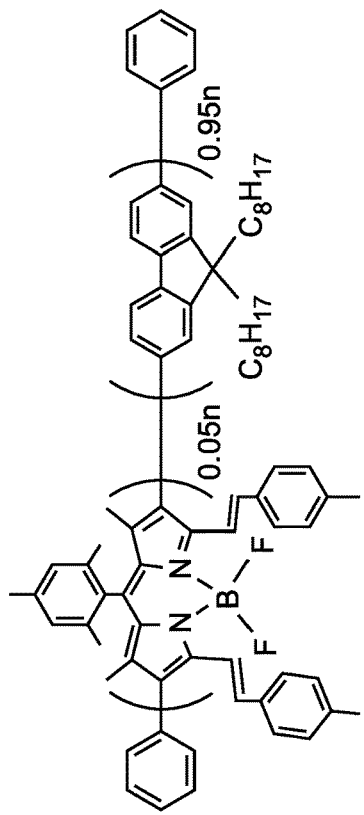
FIGS. 16A through 16E illustrate multi-color photoswitching of encoded chromophoric polymer particles.
Figure 16B:
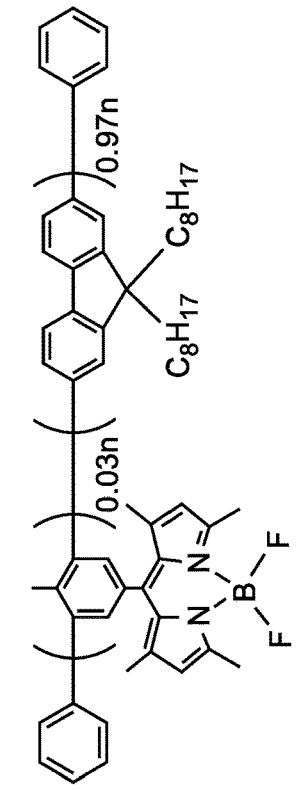
Figure 16C:
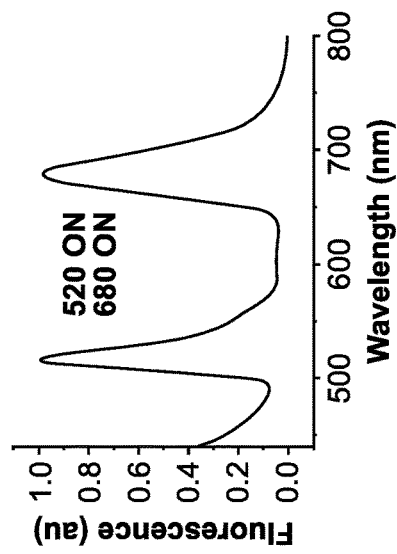
Figure 16D:
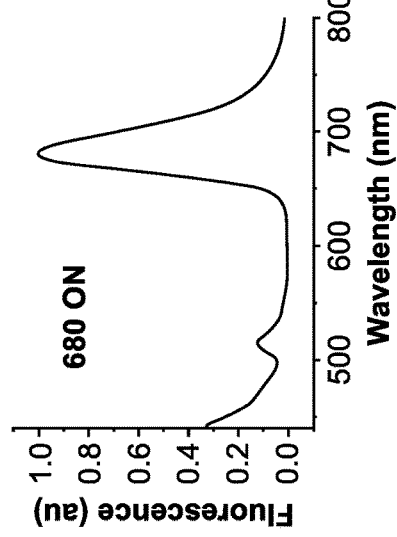
Figure 16E:
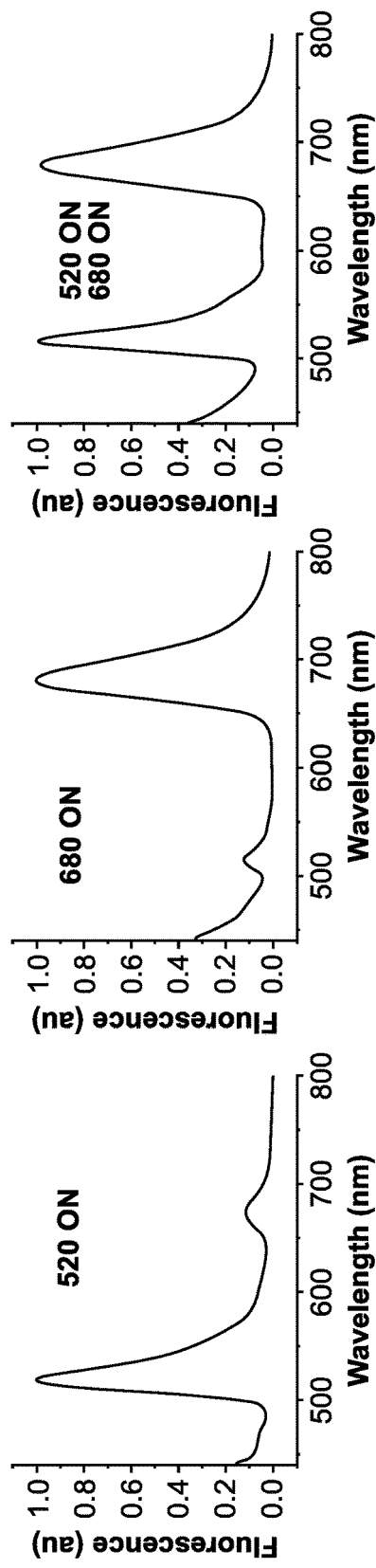

FIG. 16A illustrates a BODIPY 520 chromophoric polymer that exhibits a 520 nm emission peak. FIG. 16B illustrates a BODIPY 680 chromophoric polymer that exhibits a 680 emission peak. Coded Pdots are formed using the BODIPY 520 polymer, BODIPY 680 polymer, and two different photochromic quenchers that are switched by different wavelengths of light. One photochromic quencher is used to quench the fluorescence of BODIPY 520, while the other photochromic quencher is used to quench the fluorescence of BODIPY 680. Since each of the polymers can be switched ON or OFF independently by irradiation with the appropriate light wavelength, four different optical codes can be produced. FIG. 16E illustrates a first optical code in which both the 520 nm peak and the 680 nm peak are ON. FIG. 16C illustrates a second optical code in which only the 520 nm peak is ON. FIG. 16D illustrates a third optical code in which only the 680 nm peak is ON. A fourth optical code can be produced by having both the 520 nm peak and 680 nm peak be OFF (not shown). By using intensity in addition to wavelength, such as that described in Example 6 below, more optical codes can be created.

Example 6

Photoswitching with spectral-intensity coded chromophoric polymer particles

This example describes a spectral-intensity encoding scheme using photoswitchable chromophoric polymer particles ("Pdots"). In this example, coded Pdots having two emission peaks at 520 nm and 680 nm are used, where the fluorescence intensity of each emission peak can be individually tuned to multiple different intensity levels. Accordingly, encoding can be performed based on spectral wavelength as well as fluorescence intensity, thus enabling a large number of different codes.

Figure 17A:
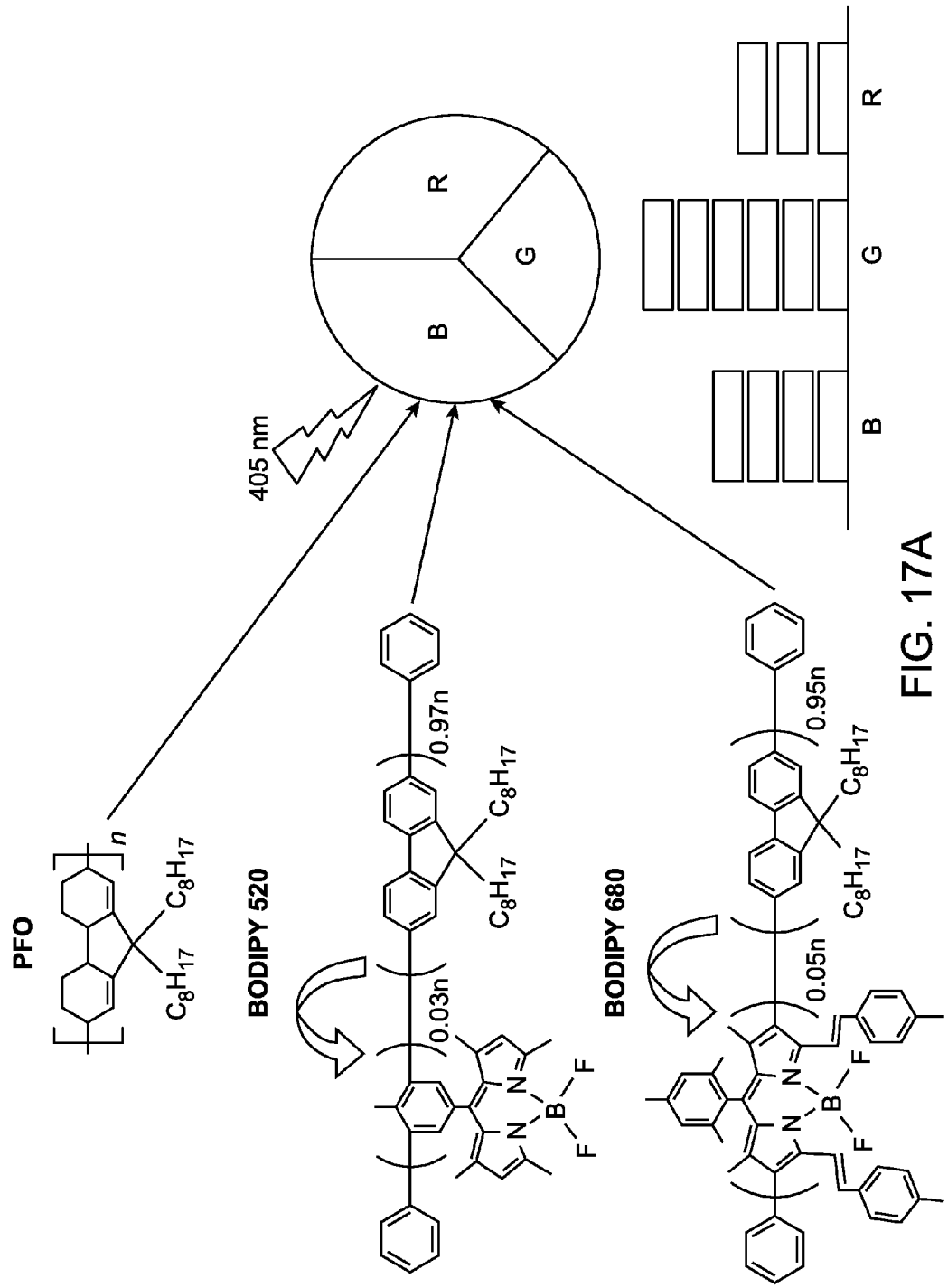
FIGS. 17A through 17C illustrate a spectral-intensity encoding scheme using photoswitchable chromophoric polymer particles.
Figure 17C:
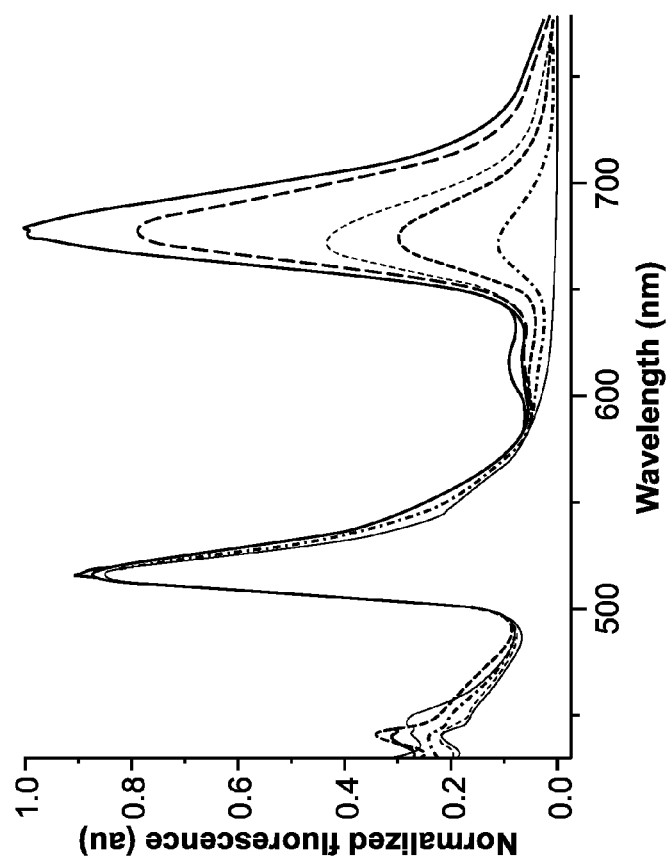
Figure 17B:
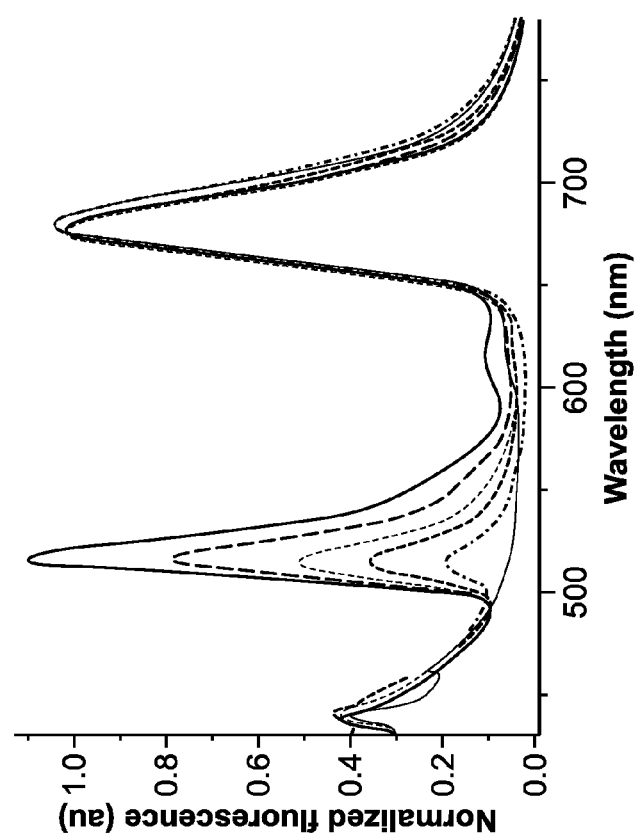

FIG. 17A is a schematic illustration of a spectral wavelength and intensity coded Pdot. The Pdot is formed using three different chromophoric polymers: polyfluorene (PFO), BODIPY 520 and BODIPY 680. The Pdot can include two different photochromic quenchers that are switched by different light wavelengths to independently quench the fluorescence of BODIPY 520, and BODIPY 680, respectively. Here, PFO is used as an internal standard or reference. Accordingly, a wavelength-based encoding can be produced. Additionally, the extent of quenching can be controlled based on the duration of irradiation in order to produce different fluorescence intensity levels for an intensity-based encoding. FIG. 17B illustrates fluorescence emission spectra of Pdots showing six intensity levels from the 520 nm emission band produced by BODIPY 520. FIG. 17C illustrates fluorescence emission spectra of Pdots showing six different intensity levels from the 680 nm emission band produced by BODIPY 680.

Example 7

Spectral-intensity coded chromophoric polymer particles using multiple colors

This example describes a spectral-intensity encoding scheme using photoswitchable chromophoric polymer particles ("Pdots"). In this example, coded Pdots having three emission peaks at 450 nm, 520 nm, and 680 nm are used. The fluorescence intensity of each emission peak can be individually tuned to multiple different intensity levels. Accordingly, encoding can be performed based on spectral wavelength as well as fluorescence intensity, thus enabling a large number of different codes.

Figure 18A:
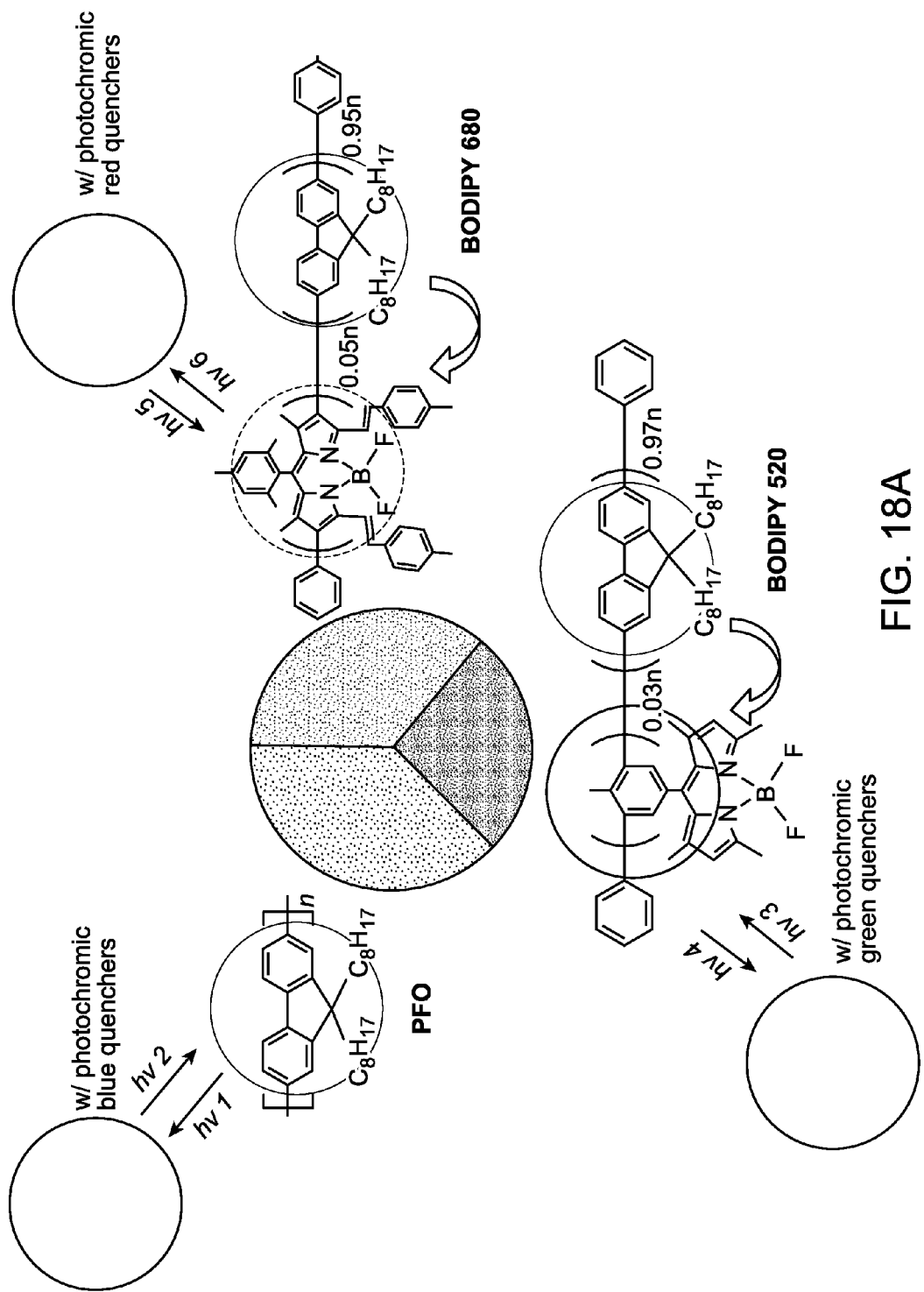

FIG. 18A is a schematic illustration of a spectral wavelength and intensity coded Pdot. The Pdot is formed using three different chromophoric polymers: polyfluorene (PFO), BODIPY 520 and BODIPY 680. The Pdot can include three different photochromic quenchers that are switched by different light wavelengths to independently quench the fluorescence of PFO, BODIPY 520, and BODIPY 680, respectively. The six different frequencies are illustrated as $v_1$ through $v_6$, and can be used to respectively increase or decrease fluorescence of their respective chromophoric polymer. Accordingly, a wavelength-based encoding can be produced. Additionally, the extent of quenching can be controlled based on the duration of irradiation in order to produce different fluorescence intensity levels for an intensity-based encoding. Thus, an RGB encoding is provided, with intensities of each color independently tunable. This permits encodings of many different states: given $n_b$ blue states, $n_g$ green states, and $n_r$ red states, a total of $n_b*n_g*n_r$ independent coding states may be produced. It will be evident that additional colors may be added to further increase the number of available coding states in a similar manner; e.g. 4, 5, 6, 10, or more colors may be used. Preferably, each color used should be spectrally distinguishable from each other color used. The colors chosen are exemplary, but may be substituted as needed. For example, in some cases other emission peaks, including infrared or ultraviolet peaks, may be provided by selection of appropriate chromophoric polymers.

FIG. 18B illustrates fluorescence emission coding of Pdots showing eleven intensity levels, from 0 (none) to 10 (max), available for each chromophoric polymer. The specific encoding illustrated has each of red, green and blue at a level of 5, giving an overall white color of medium intensity. FIG. 18C illustrates a collection of cells each independently encoded with a particular level for red, green, and blue. The respective cells are labeled in a format RXBYGZ, where X, Y, and Z correspond to the red, blue, and green fluorescence intensity levels, respectively. Accordingly, the cells have overall colors of white (upper left and lower right), red (upper right), blue (bottom center) and green (left center). Each cell shown has been prepared with respective fluorescence intensities of 5 (or 0) for each color, but they remain distinguishable by color due to their different encodings.

FIG. 18D illustrates labeling of many distinct cells with encodings using all three colors, such that they may be differentiated by both color and intensity. Each cell is encoded with red, green, or blue at an intensity varying from 0 to 10. After encoding, the cells may be tracked, identified, and isolated based on their unique codes. In this example, the label RX refers to a cell with red fluorescence level X and other fluorescence levels at 0. BY and GZ illustrate similar encodings for blue and green, mutatis mutandi. It will be further evident, based on FIGS. 18B and 18C, that the encodings of FIG. 18D may be further supplemented by mixing R, G, and B levels at independently chosen intensities. With a total of 11 independent intensities available for each of three colors, this provides up to 1331 distinguishable codes (including the R0B0G0 code, which can correspond to an unlabeled cell).

Example 8

Viability of cells labeled with coded chromophoric particles

Figure 19:
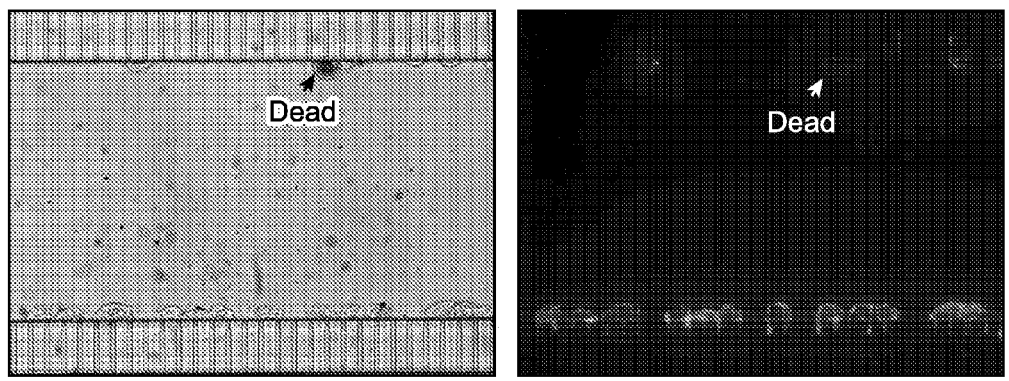
FIG. 19 illustrates the results of an experiment confirming the viability of live cells labeled, tracked, and collected using the techniques disclosed herein.

Experiments have been performed to confirm that the methods and systems described herein are applicable to live cells. FIG. 19 illustrates a measurement of cell viability after the Pdot labeling, optical painting and sorting. MCF-7 cells were labeled with OFF-form CN-PPV-BTE Pdots, painted by red light, then detached and dissociated by trypsinization, after which the painted cells were sorted and recovered by eDAR. These sorted and recovered cells were then checked for viability using the trypan blue assay, where dead cells would appear as dark blue in bright-field microscopy (pointed to by arrow in the left image) and live cells would remain clear. The viability, determined in triplicate experiments, was 90±5% after the entire process of Pdot labeling, photo-painting, trypsinization and cell detachment, and eDAR sorting and recovery. The fluorescence image in the right panel shows all the recovered cells labeled with CN-PPV-BTE Pdots. The fluorescence image was obtained by excitation via a green light from a Xe lamp and by collecting the fluorescence with a 570/20-nm band-pass filter.

Example 9

Nucleotide sequencing for cells labeled with chromophoric polymer particles

To confirm that the encoding scheme described herein is compatible with downstream analysis, encoded cells were subjected to either DNA sequencing (Sanger sequencing) or mRNA analysis. Information obtained from DNA sequencing or mRNA expression can indicate patient prognosis and inform treatment decisions. Typical genetic analysis methods require thousands to millions of cells for sufficient nucleic acid to be isolated for downstream analysis. Because of either tumor heterogeneity or the presence of healthy tissue in a biopsy, these samples can include a minority population of the cells of interest. The presence of the cells of interest in low concentrations can result in the minority molecular feature to be below the limit of detection via many techniques. Using the encoding scheme presented here, cells identified to be of interest can be obtained in high purity for genetic analysis.

As an example downstream analysis following this painting and sorting method, a portion of the PIK3CA oncogene was sequenced. This gene is commonly mutated in breast and colorectal cancers and can confer increased cell survival, proliferation, and migration. The MCF-7 cell line is known to carry a heterozygous mutation c.1633 G>A in the PIK3CA gene. Sequencing reads for exon 9 of the PIK3CA gene were performed. A sequence variant c.1633 G>A was detectable from PCR products generated from MCF-7 cells not labeled with Pdots, after Pdot-labeling and cell painting, and after eDAR-sorting of the painted and Pdot-labeled cells. The wild-type sequence reads only G at PIK3CA c.1633. This confirms, as expected, that this mutation was present in both native and Pdot-labeled MCF-7 cells (after optical painting) as well as MCF-7 cells that underwent labeling, painting, detachment, and eDAR sorting, whereas the wild-type sequence reads only G at PIK3CA c.1633. This result shows that both the painting and sorting process did not affect the interpretation of mutant status and genetic information of the cells, and that the optical painting and sorting method is compatible with downstream analysis.

Figure 20:
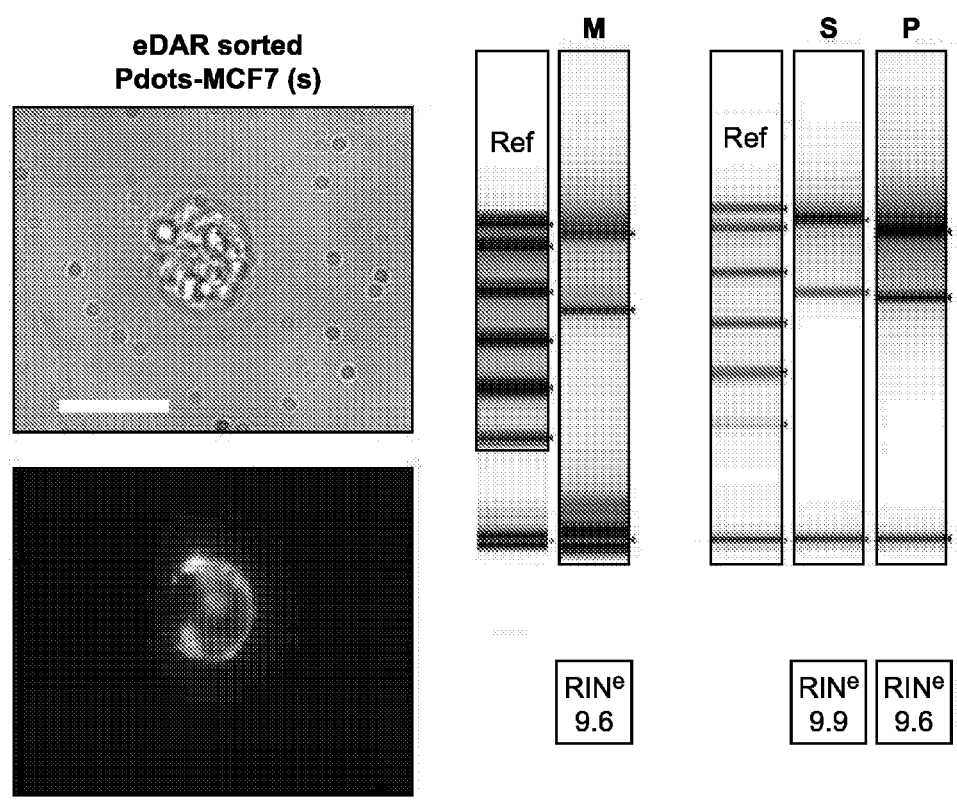
FIG. 20 illustrates results of an mRNA analysis of cells labeled, tracked, and collected using the techniques disclosed herein.

To determine the impact of the optical painting/sorting procedures on mRNA quantity and quality, an mRNA integrity experiment was performed, as illustrated in FIG. 20. For this experiment, MCF-7 cells went through the process of Pdot labeling, optical painting, and eDAR sorting. The sorted cells were flowed into an exit channel/tubing placed after the sorting junction of the eDAR chip, and then collected in an Eppendorf tube for the subsequent mRNA extraction. Control sets including untreated and Pdot-labeled MCF-7 cells were examined in parallel to investigate the effect of Pdot labeling on mRNA recovery. The quantity of recovered RNA per cell relative to untreated cells was found to be 93.8% and 90.1% for the Pdot-labeled cells and painted then eDAR-sorted cells, respectively. Additionally, the isolated RNA was of high quality for all samples, with an RNA Integrity Number (RINe) of 9.6, 9.6, and 9.9 for untreated cells, Pdot labeled cells, and Pdot-labeled then painted and eDAR sorted cells, respectively (RINe is reported on a 1-10 scale, with 10 indicating the highest quality). The results show that there is no significant mRNA damage caused by the Pdot labeling process nor by the optical painting and eDAR sorting steps, thereby indicating the high compatibility of the optical painting method with downstream analysis involving gene sequencing and mRNA expression measurements.

Example 10

Application of coded chromophoric particles to tissue cells

Figure 21:
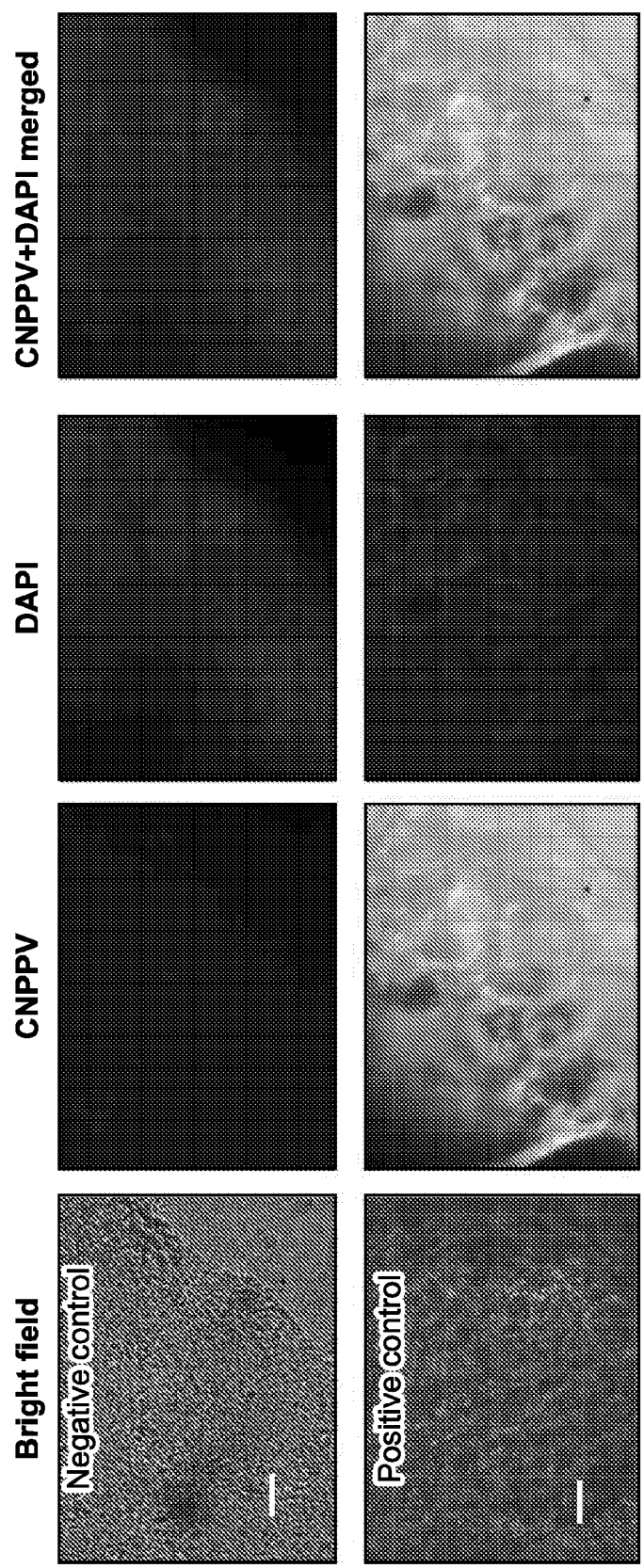
FIG. 21 illustrates the use of the techniques as disclosed herein to label biological tissue, as demonstrated using murine pancreatic tissue.

To demonstrate the relevance and potential applications of the optical painting technique in the context of tissues, these techniques were applied to murine pancreas tumors using a well-established genetically engineered mouse model of pancreatic ductal adenocarcinoma (PDA). PDA is among the most lethal of human malignancies and much effort has been spent on developing methods for early detection and on exploring mechanisms of pathogenesis in this cancer. In the experiment, a ~50 μm thick tissue slice from a mouse pancreas tumor was incubated with biotinylated anti-mouse-EpCAM antibody, followed by CN-PPV-BTE-streptavidin (CN-PPV-BTE-SA) Pdots. As illustrated in FIG. 21, Pancreas tumor slices were incubated with CN-PPV-BTE-SA Pdots in the absence (negative control) or presence (positive control) of biotinylated primary antibodies. The CN-PPV and DAPI fluorescence signals were collected through 570/20-nm band-pass and 460/30-nm band-pass filters, respectively, upon excitation with a Xe lamp. The scale bar shown corresponds to 50 μm. The Pdot-labeled tissue showed bright orange fluorescence under a microscope but dim fluorescence from the negative control, which was incubated with CN-PPV-BTE-SA Pdots but in the absence of biotinylated primary antibodies. This result indicates the efficient labeling of the tissue by Pdots and the presence of minimal non-specific binding.

Example 11

Sorting of cell populations labeled with chromophoric polymer particles

This example illustrates the use of chromophoric polymer labeling in the sorting of populations of cells. A plurality of populations of cells are marked using the encoding scheme described in Examples 1-3, such that each code corresponds to a single population. A well plate of suitable size is chosen to receive the populations. The well plate is chosen to accommodate each of the populations in a separate well. In one case, a 96-well plate is chosen to receive the populations. In a separate case, a 384-well plate is chosen to accommodate a set of populations too large to be received by the 96-well plate. The cell populations are sorted into the chosen well plate according to their codings, such that each well in which cells are deposited contains a population of cells having a particular marking. The sorting thus separates each population into a corresponding well, in a manner that allows subsequent identification and analysis of said populations.

Example 12

Sorting of cells using single-cell dispensing

In this example, a plurality of adherent cells are marked with a respective set of optical markers, as described in detail in Examples 1-3. Different subsets of the cells are illuminated with different optical radiation, so as to mark each subset with a unique code. This code provides identifying information such that the original characteristics of a single cell can be retrieved upon future analysis. By uniquely identifying subsets of cells by their initial marking, information about their initial state is preserved for later retrieval; for example, the spatial location of the cell in the tissue, the temporal characteristics of the cell, the appearance of the cell in tissue, the morphology of the cell in tissue, the phenotypic properties of the cell in tissue, or the physiology of the cell observed in tissue, or a combination of these characteristics can be determined based on the encoding procedure and subsequent measurements.

A single-cell dispensing device is used to dispense individual cells into microwells. In a separate example, the cells are instead dispensed into droplets. Thereafter, in each example, the identity of each cell is decoded optically according to the different optical encodings. After single-cell dispensing and optical decoding to uncover the original characteristics of the cells, the cells are lyzed for single-cell analysis. This procedure allows the results of each holder's single-cell analysis to be correlated to a particularly-identified subset of cells.

While preferred aspects of the present invention have been shown and described herein, it will be obvious to those skilled in the art that such aspects are provided by way of example only. Numerous variations, changes, and substitutions will now occur to those skilled in the art without departing from the invention. It should be understood that various alternatives to the aspects of the invention described herein can be employed in practicing the invention. It is intended that the following claims define the scope of the invention and that methods and structures within the scope of these claims and their equivalents be covered thereby.

What is claimed is:

1. A method of optically marking and sorting adherent cells, the method comprising:
    providing a plurality of adherent cells attached to a substrate, each adherent cell of the plurality of adherent cells comprising an optical marker comprising a chromophoric polymer particle in a first optical state, the optical marker being convertible from the first optical state to a second optical state upon application of light energy, wherein an emission intensity of the optical marker at a peak emission wavelength in the first optical state is at least 10-fold different than an emission intensity of the optical marker at the peak emission wavelength in the second optical state, and wherein the optical marker has a time constant of reversion rate of at least 3 hours at 25° C.;
    selectively applying the light energy to a subset of the plurality of adherent cells while attached to the substrate, thereby selectively converting the optical markers of the subset from the first optical state to the second optical state;
    detaching the plurality of adherent cells from the substrate; and
    sorting the plurality of adherent cells based on the emission intensity of the optical marker.

2. The method of claim 1, wherein the optical marker comprises a photoswitchable chromophore.

3. The method of claim 1, wherein the optical marker comprises a photoactivatable chromophore.

4. The method of claim 1, wherein the chromophoric polymer particle comprises a polymer matrix comprising a chromophoric polymer, and a photochromic molecule.

5. The method of claim 1, wherein the subset of the plurality of adherent cells is selected based on spatial features of the subset when attached to the substrate.

6. The method of claim 1, wherein the subset of the plurality of adherent cells is selected based on morphological features of the subset when attached to the substrate.

7. The method of claim 1, wherein each adherent cell comprises a second optical marker in a third optical state, and wherein the method further comprises:
    selectively applying a second light energy to a second subset of the plurality of adherent cells while attached to the substrate, thereby converting the second optical markers of the second subset from the third optical state to a fourth optical state.

8. The method of claim 1, further comprising obtaining image data of the plurality of adherent cells using an imaging device and selecting the subset of the plurality of adherent cells based on the image data.

9. The method of claim 1, wherein the chromophoric polymer particle is a photoswitchable chromophoric polymer particle, the photoswitchable chromophoric polymer particle comprising a polymer matrix comprising a chromophoric polymer and a photochromic molecule.

10. The method of claim 9, wherein the chromophoric polymer comprises poly(9,9-dihexylfluorenyl-2,7-diyl) (PDHF), poly(9,9-dioctylfluorenyl-2,7-diyl)(PFO), poly[{9,9-dioctyl-2,7-divinylene-fluorenylene}-alt-co-{2-methoxy-5-(2-ethylhexyloxy)-1,4-phenylene}](PFPV), poly[(9,9-dioctylfluorenyl-2,7-diyl)-co-(1,4-benzo-{2, 1 ,3}-thiadiazole)](PFBT), poly[(9,9-dioctylfluorenyl-2,7-diyl)-co-(4,7-Di-2-thienyl-2,1,3-benzothiadiazole)](PFTBT), poly[2-methoxy-5-(2-ethylhexyloxy)-1,4-phenylenevinylene](MEH-PPV), poly[2-methoxy-5-(2-ethylhexyloxy)-1,4-(1-cyanovinylene-1,4-phenylene)](CN-PPV), poly(2,5-di(3',7'-dimethyloctyl)phenylene-1,4-ethynylene (PPE), or a combination thereof.

11. A system for optically marking and sorting adherent cells, the system comprising:
    a plurality of adherent cells attached to a substrate, each adherent cell of the plurality of adherent cells comprising an optical marker comprising a chromophoric polymer particle in a first optical state, the optical marker being convertible from the first optical state to a second optical state upon application of light energy, wherein an emission intensity of the optical marker at a peak emission wavelength in the first optical state is at least 10-fold different than an emission intensity of the optical marker at the peak emission wavelength in the second optical state, and wherein the optical marker has a time constant of reversion rate of at least 3 hours at 25° C.;
    a light source;
    one or more processors operably coupled to the light source and individually or collectively configured to cause the light source to selectively apply the light energy to a subset of the plurality of adherent cells while attached to the substrate, thereby selectively converting the optical markers of the subset from the first optical state to the second optical state; and
    a cell sorting device configured to sort the plurality of adherent cells when detached from the substrate based on the emission intensity of the optical marker.

12. The system of claim 11, wherein the optical marker comprises a photoswitchable chromophore.

13. The system of claim 11, wherein the optical marker comprises a photoactivatable chromophore.

14. The system of claim 11, wherein the chromophoric polymer particle comprises a polymer matrix comprising a chromophoric polymer, and a photochromic molecule.

15. The system of claim 11, further comprising a detector, wherein the one or more processors are configured to receive a signal from the detector indicative of emission intensity levels of the optical markers of the subset, and modify the light energy applied by the light source in response to the received signal.

16. The system of claim 11, wherein the subset of the plurality of adherent cells is selected based on spatial features of the subset when attached to the substrate.

17. The system of claim 11, wherein the subset of the plurality of adherent cells is selected based on morphological features of the subset when attached to the substrate.

18. The system of claim 11, wherein each adherent cell comprises a second optical marker in a third optical state, and wherein the one or more processors are further configured to cause the light source to selectively apply a second light energy to a second subset of the plurality of adherent cells while attached to the substrate, thereby converting the second optical markers of the second subset from the third optical state to a fourth optical state.

19. The system of claim 11, further comprising an imaging device configured to obtain image data of the plurality of adherent cells, wherein the one or more processors are configured to select the subset of the plurality of adherent cells based on the image data.

20. A method of sorting adherent cells using optically detectable codes, the method comprising:
   providing a plurality of adherent cells attached to a substrate, each adherent cell of the plurality of adherent cells comprising an optical marker comprising a chromophoric polymer particle in a first optical state, the optical marker being convertible from the first optical state to a second optical state upon application of light energy, wherein the first optical state defines a first optically detectable code and the second optical state defines a second optically detectable code, and wherein the optical marker has a time constant of reversion rate of at least 3 hours at 25° C.;
   selectively applying the light energy to a subset of the plurality of adherent cells while attached to the substrate, thereby selectively converting the optical markers of the subset from the first optical state to the second optical state;
   detaching the plurality of adherent cells from the substrate; and
   sorting the plurality of adherent cells based on whether the optical marker of each adherent cell is exhibiting the first optically detectable code or the second optically detectable code.

\* \* \* \* \*